United States Patent
Gnamm et al.

(10) Patent No.: US 9,290,459 B1
(45) Date of Patent: Mar. 22, 2016

(54) SUBSTITUTED BICYCLIC DIHYDROPYRIMIDINONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Christian Gnamm, Biberach an der Riss (DE); Thorsten Oost, Biberach an der Riss (DE); Stefan Peters, Biberach an der Riss (DE); Holger Hoesch, Biberach an der Riss (DE); Uwe Joerg Ries, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/935,915

(22) Filed: Nov. 9, 2015

Related U.S. Application Data

(63) Continuation of application No. 14/166,146, filed on Jan. 28, 2014, now abandoned.

(30) Foreign Application Priority Data

Feb. 6, 2013 (EP) .................... 13154256

(51) Int. Cl.
| | |
|---|---|
| *C07D 239/70* | (2006.01) |
| *C07D 403/12* | (2006.01) |
| *C07D 401/12* | (2006.01) |
| *A61K 31/517* | (2006.01) |
| *A61P 9/12* | (2006.01) |

(52) U.S. Cl.
CPC ............ *C07D 239/70* (2013.01); *A61K 31/517* (2013.01); *C07D 401/12* (2013.01); *C07D 403/12* (2013.01)

(58) Field of Classification Search
CPC .. C07D 239/70; C07D 403/12; C07D 401/12; A61K 31/517; A61K 45/06
USPC ........................................ 544/253; 514/258.1
See application file for complete search history.

(56) References Cited

U.S. PATENT DOCUMENTS 9,115,093 B2   8/2015   Gnamm et al.

FOREIGN PATENT DOCUMENTS

WO   2007129060 A1   11/2007

OTHER PUBLICATIONS

Bartoli et al., Biological markers in induced sputum of patients with different phenotypes of chronic airway obstruction, Respiration, 2009, 77(3), 265-72.

Bizeto et al., Interrelationship between serum and sputum inflammatory mediators in chronic obstructive pulmonary disease, Braz J Med Biol Res., Mar. 2008, 41(3), 193-8.

Carter et al., Aa-Va1360:a marker of neutrophil elastase and COPD disease activity, Eur Respir J, 2013, 41, 31-38.

Carter et al., The firbinogen cleavage product Aa-Val360, a specific marker of neutrophil elastase activity in vivo, orax, 2011, 66, 686-691.

Chapman et al., Augmentation Therapy Is Disease Modifying in Alpha-1 Antitrypsin Deficiency (aatd), Interim Analysis of the Rapid Extension Study, Am J Respir Crit Care Med, 189, 2014, A5788.

Crooks et al., Bronchial inflammation in acute bacterial exacerbations of chronic bronchitis: the role of leukotriene B4, Eur. Respir J., Feb. 2000, 15(2), 274-80.

Demkow et al., Role of elastases in the pathogenesis of chronic obstructive pulmonary disease: implications for treatment, Eur J Med Res., Nov. 4, 2010,15 Suppl 2, 27-35.

Gehrig et al., Lack of neutrophil elastase reduces inflammation, mucus hypersecretion, and emphysema, but not mucus obstruction, in mice with cystic fibrosis-like lung disease, Am J Respir Crit Care Med, May 1, 2014, 189(9), 1082-92.

Groutas et al., Neutrophil Elastase Inhibitors, Expert Opinion Ther Pat, 2011 , 21 (3), pp. 339-354.

International Search Report, form PCT/ISA/210, for corresponding application PCT/EP2014/052217, date of mailing Apr. 3, 2014.

Janoff et al., Cigarette smoke inhalation decreases alpha 1-antitrypsin activity in rat lung, Science, Dec. 14, 1979, 206(4424), 1313-4.

Needham et al., Alpha 1-antitrypsin deficiency 3: Clinical manifestations and natural history, Thorax, May 2004; 59 (5):441-5.

(Continued)

*Primary Examiner* — Venkataraman Balasubramanian

(74) *Attorney, Agent, or Firm* — Michael P. Morris; Philip I. Datlow

(57) ABSTRACT

This invention relates to substituted bicyclic dihydropyrimidinones of formula 1

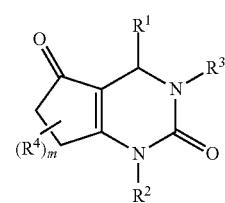

and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other autoimmune and allergic disorders, allograft rejection, and oncological diseases.

43 Claims, No Drawings

(56) References Cited

OTHER PUBLICATIONS

Piccioni et al., Proteinase/proteinase inhibitor imbalance in sputum sol phases from patients with chronic obstructive pulmonary disease. Suggestions for a key role played by antileukoprotease, Chest, Nov. 1992, 102(5), 1470-6.

Shapiro et al., Neutrophil elastase contributes to cigarette smoke-induced emphysema in mice, Am J Pathol, Dec. 2003, 163(6), 2329-35.

Snyder et al., Common bacteria whose susceptibility to antimicrobials is no longer predictable, J Med Liban, 48 (4), 2000, pp. 208-214.

Stevens et al., AZD9668: pharmacological characterization of a novel oral inhibitor of neutrophil elastase, J Pharmacol Exp Ther, Oct. 2011, 339(1), 313-20.

Sugar et al., Comparison of Three Methods of Antifungal Susceptibility Testing with the proposed NCCLS Standards Broth MAcrodilution Assay: Lack of Effect of Phenol Red, Diagno Microbiol. Infect. Dis., 1995, vol. 21, pp. 129-133.

Turner et al., Recent Advances in the Medicinal Chemistry of Antifungal Agents, Current Pharmaceutical Design, 1996, vol. 2, pp. 209-224.

SUBSTITUTED BICYCLIC DIHYDROPYRIMIDINONES AND THEIR USE AS INHIBITORS OF NEUTROPHIL ELASTASE ACTIVITY

This invention relates to substituted bicyclic dihydropyrimidinones of formula 1

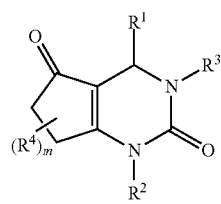

1 and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other autoimmune and allergic disorders, allograft rejection, and oncological diseases.

BACKGROUND INFORMATION

The following references describe neutrophil elastase inhibitors with a monocyclic dihydro-pyrimidinone core: GB2392910, WO04024700, WO05082864, WO05082863, DE102006031314, U.S. Ser. No. 10/001,0024, WO10115548, WO09080199, DE102007061766, WO06136857, WO06082412, WO12002502.

The following references describe neutrophil elastase inhibitors with a bicyclic tetrahydropyrrolopyrimidinedione core: WO07129060, WO08135537, U.S. Ser. No. 09/009,3477, WO09013444, WO09060206, WO09060203, WO09060158, U.S. Ser. No. 11/003,4433.

The following references describe neutrophil elastase inhibitors with core structures other than those herein before mentioned: WO04020412, WO04020410, WO03053930, WO10078953, WO09135599, DE102009004197, WO11110858, WO11110859, WO09060158, WO09037413, WO04024701, U.S. Ser. No. 13/006,5913, WO13018804, WO12002502.

For a review on various inhibitors of neutrophil elastase see: P. Sjö (*Future Med. Chem.* 2012, 4, 651-660).

BRIEF SUMMARY OF THE INVENTION

Neutrophil elastase (NE) is a 29 kDa serine protease. It is expressed in bone marrow precursor cells, stored in the granula of peripheral blood granulocytes at high concentrations and it is released upon cellular activation. To the substrates of NE belong major elements of the extracellular matrix: elastin, fibronectin, laminin, collagen and proteoglycans. Neutrophil elastase activity leads to ECM degradation, increases migration and chemotaxis of monocytes and vascular smooth muscle cells and directly affects components of the coagulation and fibrinolytic pathways (PAI-1 and TFPI). Increased activity of neutrophil elastase is associated with chronic inflammatory and fibrotic diseases of several organs Inhibitors of neutrophil elastase will therefore have an important role for the treatment of different diseases like COPD, idiopathic pulmonary fibrosis and other fibrotic diseases, cancer, acute lung injury, acute respiratory distress syndrome, bronchiectasis, cystic fibrosis, alpha1-antitrypsin deficiency and others.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, are additionally effective as inhibitors of neutrophil serin protease proteinase 3 and exhibit favourable inhibitory potency, as determined by the half maximal inhibitory concentration ($IC_{50}$), in an enzymatic inhibition assay. This inhibitory activity on a second neutrophil serin protease may be beneficial for pharmacological efficacy.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al. (*J. Pharm. Exp. Ther.* 2011, 339, 313-320).

Some compounds according to the present invention, including the physiologically acceptable salts, exhibit favourable in vivo potency, as determined, for example, by the half maximal effective dose ($ED_{50}$), in models of human neutrophil elastase-induced lung injury in mice, rat or hamster, for instance as described in Tremblay et al. (*Chest* 2002, 121, 582-588) or T. Stevens et al. (*J. Pharm. Exp. Ther.* 2011, 339, 313-320).

Some compounds according to the present invention, including the physiologically acceptable salts, exhibit favourable in vivo potency, as determined, for example, by the half maximal effective dose ($ED_{50}$), in a model of LPS/FMLP-induced lung injury in hamster, for instance as described in Mitsuhashi et al. (*Br. J. Pharmacol.* 1999, 126, 1147-1152).

Some compounds according to the present invention, including the physiologically acceptable salts, exhibit favourable metabolic stability in an in vitro microsomal assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

Some compounds according to the present invention, including the physiologically acceptable salts, exhibit favourable metabolic stability in an in vitro hepatocytes assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}=Dose/AUC$ ($F_{oral}$: oral bioavailability, AUC: area under the curve), a reduced in vivo clearance is expected to lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di (*Drug-like properties: concepts, structure design and methods: from ADME to toxicity optimization*, Elsevier, 1$^{st}$ ed, 2008), chapter 26 and references therein. For an oral drug, improved permeability is expected to translate into a higher fraction of the drug absorbed in the intestinal tract, thus, resulting in higher dose-normalized systemic exposure (AUC).

Some compounds according to the present invention, including the physiologically a) acceptable salts, exhibit a favourable, that is low efflux ratio (permeability in the efflux direction divided by the permeability in the influx direction) in an in vitro Caco-2 or MDCK cell layer method as described in E. Kerns & L. Di (*Drug-like properties: concepts, structure design and methods: from ADME to toxicity optimization*, Elsevier, 1$^{st}$ ed, 2008), chapter 26 and 27 and references therein. For an oral drug, an improved, that is reduced efflux ratio is expected to translate into a higher fraction of the drug absorbed in the intestinal tract, thus, resulting in higher dose-normalized systemic exposure (AUC).

Some compounds according to the present invention, including the physiologically acceptable salts, exhibit favourable aqueous solubility in a kinetic or thermodynamic solubility method as described in E. Kerns & L. Di (*Drug-like properties: concepts, 15 structure design and methods: from ADME to toxicity optimization*, Elsevier, 1$^{st}$ ed, 2008), chapter 25 and references therein. For an oral drug, improved aqueous solubility is expected to translate into a higher fraction of the drug absorbed in the intestinal tract resulting in higher dose-normalized systemic exposure (AUC).

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or prolonged duration of action of the drug when the same dose is applied.

Some compounds according to the present invention, including the physiologically acceptable salts, exhibit favourable metabolic stability, favourable permeability, favourable efflux ratio and favourable aqueous solubility. Accordingly, some compounds of the present invention are expected to exhibit favourable pharmacokinetic (PK) properties after oral dosing, in particular favourable systemic exposure (area under the curve, AUC), thus, leading to favourable efficacy in vivo.

Some compounds according to the present invention, including the physiologically acceptable salts, exhibit favourable pharmacokinetic (PK) properties. The PK properties can be determined in pre-clinical animal species, for example mouse, rat, hamster, dog, guinea pig, mini pig, cynomolgus monkey, rhesus monkey. The PK properties of a compound can be described, for example, by the following parameters: Mean residence time (MRT), elimination half-live ($t_{1/2}$), volume-of-distribution ($V_D$), area under the curve (AUC), clearance (CL) and bioavailability after oral administration ($F_{oral}$).

The compounds of the invention and metabolites thereof are devoid of the hydrazine sub-structure that causes structural alerts for mutagenicity and carcinogenicity as described in Benigni et al. (*Chem. Rev.* 2011, 11, 2507-2536). Thus, compounds of the invention may bear the advantage of reduced genotoxic potential.

Some compounds according to the present invention, including the physiologically acceptable salts, exhibit favourable inhibition of cytochrome P450 (CYP) isozymes in corresponding in vitro assays for CYP isozyme inhibition as described in E. Kerns & L. Di (*Drug-like properties: concepts, structure design and methods: from ADME to toxicity optimization*, Elsevier, 1$^{st}$ ed, 2008), chapter 32 and references therein. Reduced inhibition of CYP isozymes is expected to translate into a reduced risk for undesirable drug-drug interactions which is the interference of one drug with the normal metabolic or pharmacokinetic behaviour of a co-administered drug.

Some compounds according to the present invention, including the physiologically acceptable salts, exhibit favourable, i.e. low, inhibition of the hERG channel in a patch clamp assay as described in E. Kerns & L. Di (*Drug-like properties: concepts, structure design and methods: from ADME to toxicity optimization*, Elsevier, 1$^{st}$ ed, 2008), chapter 34 and references cited therein.

DETAILED DESCRIPTION OF THE INVENTION

A compound of formula 1

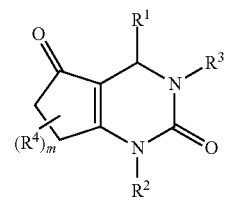

wherein
R$^1$ is phenyl or a five- or six-membered heteroaryl, wherein one, two or three elements are replaced by an element independently selected from the group consisting of N, O and S; preferably phenyl or pyridinyl; each ring optionally substituted with one, two or three substituents independently selected from the group consisting of halogen, O$_2$N—, NC—, H$_2$N—, HO—, R$^{1.1}$, R$^{1.1}$O—, R$^{1.2}$, R$^{1.3}$S—, R$^{1.3}$(O)$_2$S— and R$^{1.3}$(O)$_2$S—;
R$^{1.1}$ is independently selected from the group consisting of C$_{1-6}$-alkyl-, C$_{3-6}$-cycloalkyl-, C$_{1-6}$-haloalkyl-, and C$_{3-6}$-halocycloalkyl;
R$^{1.2}$ is HO—C$_{1-6}$-alkyl- or R$^{1.1}$—O—C$_{1-6}$-alkyl-;
R$^{1.3}$ is independently selected from the group consisting of H, HO—, R$^{1.1}$ and R$^{1.2}$; preferably R$^{1.1}$;
R$^2$ is phenyl or a five- or six-membered heteroaryl, wherein one or two elements are replaced by an element independently selected from the group consisting of N, O and S; preferably phenyl and pyridinyl; each ring optionally substituted with a substituent independently selected from the group consisting of halogen, C$_{1-4}$-alkyl-, C$_{1-4}$-haloalkyl- and C$_{1-4}$-alkyl-O—;
R$^3$ is a residue independently selected from the group consisting of
R$^{3.1}$—;
R$^{3.2}$(O)C—;
R$^{3.2}$O(O)C—;
s R$^{3.2}$O(O)C-A-; preferably R$^{3.2}$O(O)C—CH$_2$—;
R$^{3.2}$S—; R$^{3.2}$(O)S—; R$^{3.2}$(O)$_2$S—; preferably R$^{3.2}$(O)$_2$S—;
(R$^{3.2}$)$_2$N(O)C and
(R$^{3.2}$)$_2$N(O)C-A-; preferably (R$^{3.2}$)$_2$N(O)C—CH$_2$—;
R$^{3.1}$ is independently selected from the group consisting of H, R$^{3.3}$, R$^{3.4}$, C$_{1-6}$-alkyl-C$_{3-6}$-cycloalkyl- and C$_{3-6}$-cycloalkyl-C$_{1-6}$-alkyl-, each optionally substituted with one or two substituents independently selected from R$^{3.1.1}$—;
R$^{3.1.1}$ is selected from the group consisting of HO—, halogen, NC—, R$^{3.3}$O—, R$^{3.5}$, R$^{3.6}$ and R$^{3.7}$ or $R^{3.1.1}$ denotes a ring independently selected from phenyl and a four-membered heterocyclic ring containing one element independently selected from among N, O, S, S(O) and S(O)$_2$ or $R^{3.1.1}$ denotes a five- or six-membered heterocyclic or heteroaryl ring containing one, two or three elements independently selected from among N, O, S, S(O) and S(O)$_2$; each of the rings optionally substituted with one or two substituents independently selected from among HO—, O=, halogen, NC—, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$;

$R^{3.2}$ is independently selected from $R^{3.1}$, phenyl or a five- or six-membered heterocyclic or heteroaryl ring containing one, two or three elements independently selected from N, O, S, S(O) and S(O)$_2$; each ring optionally substituted with one or two substituents independently selected from HO—, O=, NC—, halogen, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$;

or two $R^{3.2}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from among N, O, S, S(O) and S(O)$_2$; optionally substituted with one or two substituents, independently selected from among HO—, F, O=, NC—, $R^{3.3}$, $R^{3.3}$O—, $R^{3.3}$—(O)C—, $R^{3.4}$, $R^{3.5}$, $R^{3.6}$, $R^{3.7}$, phenyl and a five- or six-membered heterocyclic or heteroaryl ring containing one, two or three elements independently selected from among N, O, S, S(O) and S(O)$_2$; or two substituents are together $R^{3.8}$;

$R^{3.3}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{3.4}$ is HO—$C_{1-6}$-alkyl- or $R^{3.3}$—O—$C_{1-6}$-alkyl-;

$R^{3.5}$ is independently selected from the group consisting of $H_2N$—, $R^{3.3}$—HN—, $(R^{3.3})_2N$—, $R^{3.3}$—(O)C—HN— and $R^{3.3}$—(O)C—$(R^{3.3})N$—;

$R^{3.6}$ is independently selected from the group consisting of $R^{3.3}$—(O)S—, $R^{3.3}$—(O)$_2$S—, $R^{3.3}$(HN)S—, $R^{3.3}$(HN)(O)S—, $R^{3.3}(R^{3.3}N)S$—, $R^{3.3}(R^{3.3}N)(O)S$—, $R^{3.3}(R^{3.4}N)S$—, $R^{3.3}(R^{3.4}N)(O)S$—; $R^{3.3}$(NC—N)S— and $R^{3.3}$(NC—N)(O)S—;

$R^{3.7}$ is independently selected from the group consisting of HO(O)C—, $H_2N$(O)C—, $R^{3.3}$—O—(O)C—, $R^{3.3}$—NH—(O)C— and $(R^{3.3})_2N$—(O)C—;

$R^{3.8}$ is independently selected from the group consisting of $C_{1-6}$-alkylene and $C_{1-6}$-haloalkylene, wherein optionally one or two CH$_2$-groups are replaced by —HN—, —$(R^{3.3})N$—, —$(R^{3.4})N$—, —$(R^{3.3}$(O)C—)N—, —$(R^{3.4}$(O)C—)N—, —O—, —S—, —S(O)— or —S(O)$_2$—;

A is —CH$_2$—, —CH$_2$—CH$_2$— or —CH$_2$—CH$_2$—CH$_2$—; preferably —CH$_2$—; optionally substituted with one or two substituents independently selected from the group consisting of halogen, $R^{3.3}$, $R^{3.3}$O—, $R^{3.4}$ or two substituents together are $R^{3.8}$;

$R^4$ is independently selected from the group consisting of halogen, $C_{1-6}$-alkyl-, $C_{3-6}$-cycloalkyl-, $C_{1-6}$-haloalkyl- and $C_{3-6}$-halocycloalkyl; or two $R^4$ are together $C_{1-6}$-alkylene or $C_{1-6}$-haloalkylene;

m is 0, 1 or 2; preferably 0;

or a salt thereof.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, S(O), S(O)$_2$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

For example, the term "3-carboxypropyl-group" represents the following substituent:

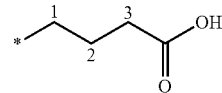

wherein the carboxy group is attached to the third carbon atom of the propyl group. The terms "1-methylpropyl-", "2,2-dimethylpropyl-" or "cyclopropylmethyl-" group represent the following groups:

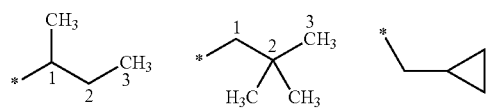

The asterisk may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

All isomeric forms (especially all stereoisomeric forms, e.g. all chiral, enantiomeric, diastereomeric and racemic forms, all tautomeric and all geometric isomeric forms) of a compound of the present invention are intended with this invention, unless the specific isomer is specifically indicated. Obviously, the isomer which is pharmacologically more potent and/or more efficacious is preferred.

It will be appreciated that the compounds of the present invention contain at least one asymmetrically substituted carbon atom, and may therefore be isolated as pure enantiomers or as a racemic or non-racemic mixture of both enantiomers. It will be appreciated that some of the compounds of the present invention contain more than one stereogenic center, i.e. more than one asymmetrically substituted carbon or sulfur atom, and may therefore be isolated as pure diastereomers or as diastereomeric mixtures, both in optically active or racemic forms.

The invention contemplates all conceivable stereoisomers, particularly the diastereomers and enantiomers mentioned herein, e.g. in substantially pure form, in enriched form (e.g. substantially free of any or all other undesired enantiomers and/or diastereomers and/or in any mixing ratio, including the racemic forms, as well as the salts thereof.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris-(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —CH$_2$—, —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH(CH$_3$)—CH$_2$—, —CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

By the term "halo" added to a "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: H$_2$FC—, HF$_2$C—, F$_3$C—.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring system including aromatic ring system containing one or more elements selected from N, O, S, S(O) or S(O)$_2$, consisting of 3 to 14 ring atoms wherein none of the heteroatoms is part of the aromatic ring. The term "heterocyclyl" is intended to include all the possible isomeric forms; thus, the term "heterocyclyl" includes the following exemplary structures which are not depicted as radicals as each form may be attached through a covalent bond to any atom so long as appropriate valences are maintained:

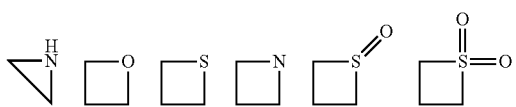

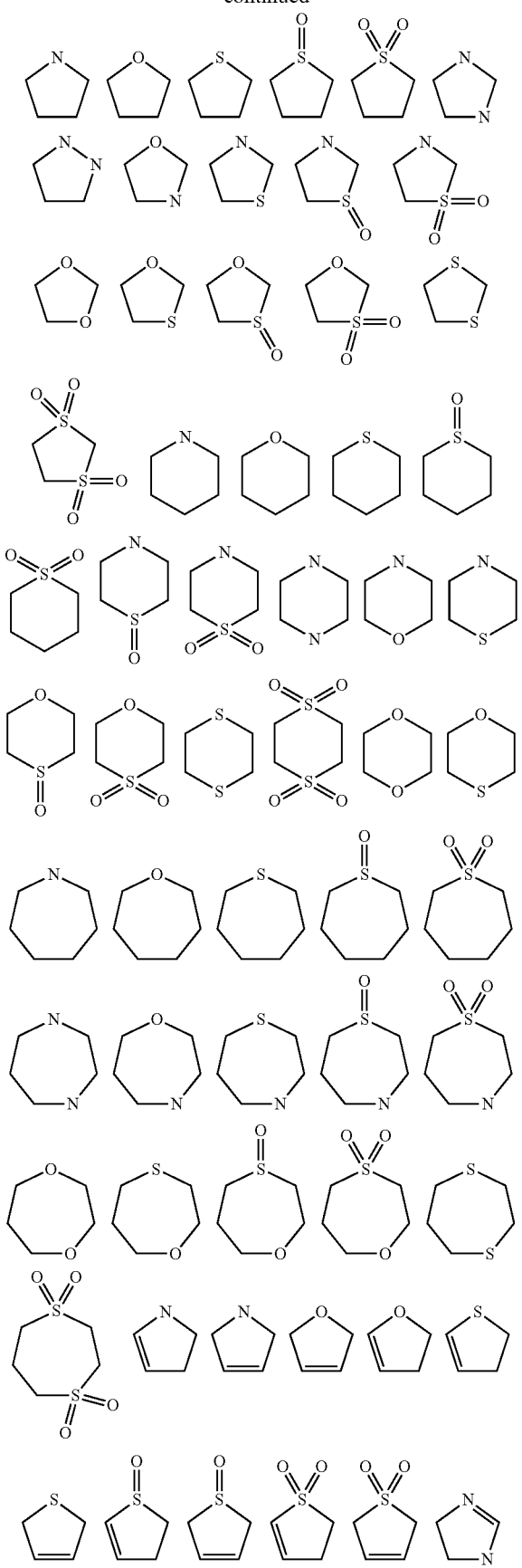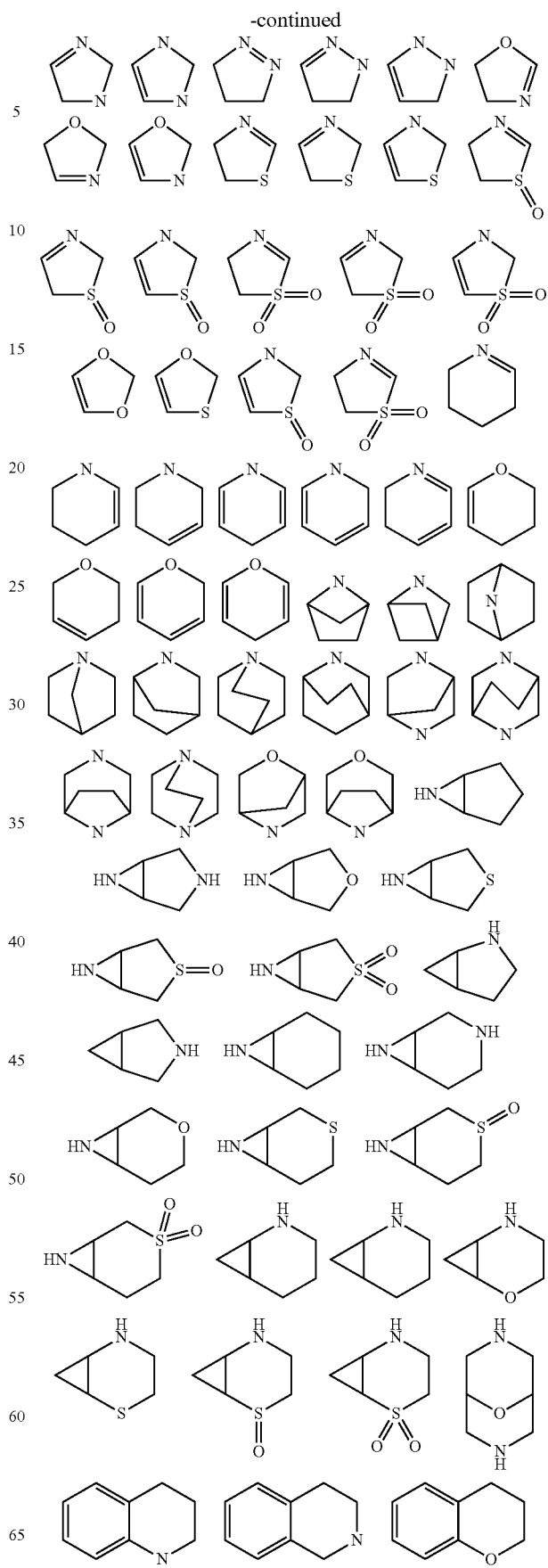

-continued

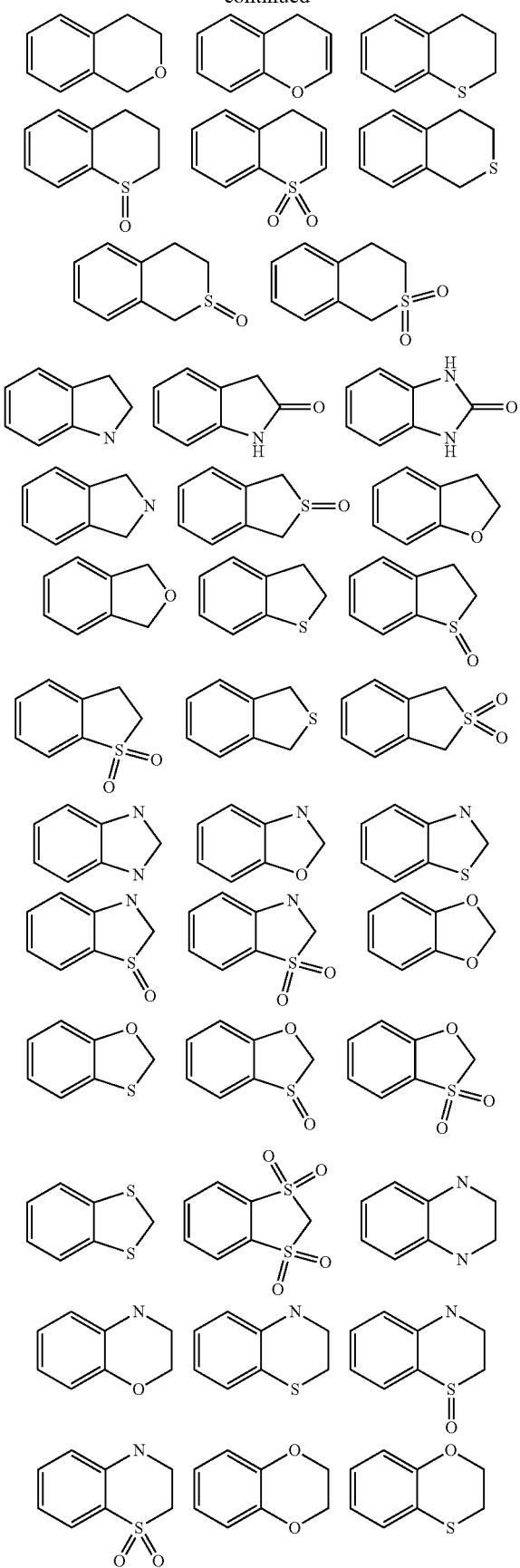

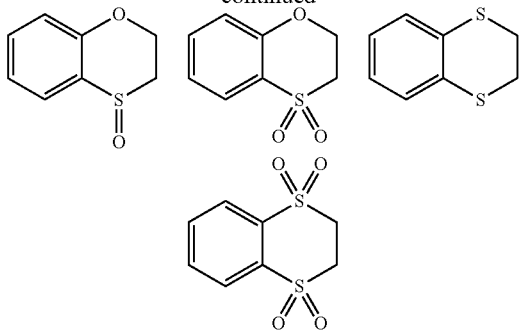

The term "heteroaryl" means a mono- or polycyclic-ring systems containing one or more elements selected from N, O, S, S(O) or S(O)$_2$, consisting of 5 to 14 ring atoms wherein at least one of the heteroatoms is part of aromatic ring. The term "heteroaryl" is intended to include all the possible isomeric forms; Thus, the term "heteroaryl" includes the following exemplary structures which are not depicted as radicals as each form may be attached through a covalent bond to any atom so long as appropriate valences are maintained:

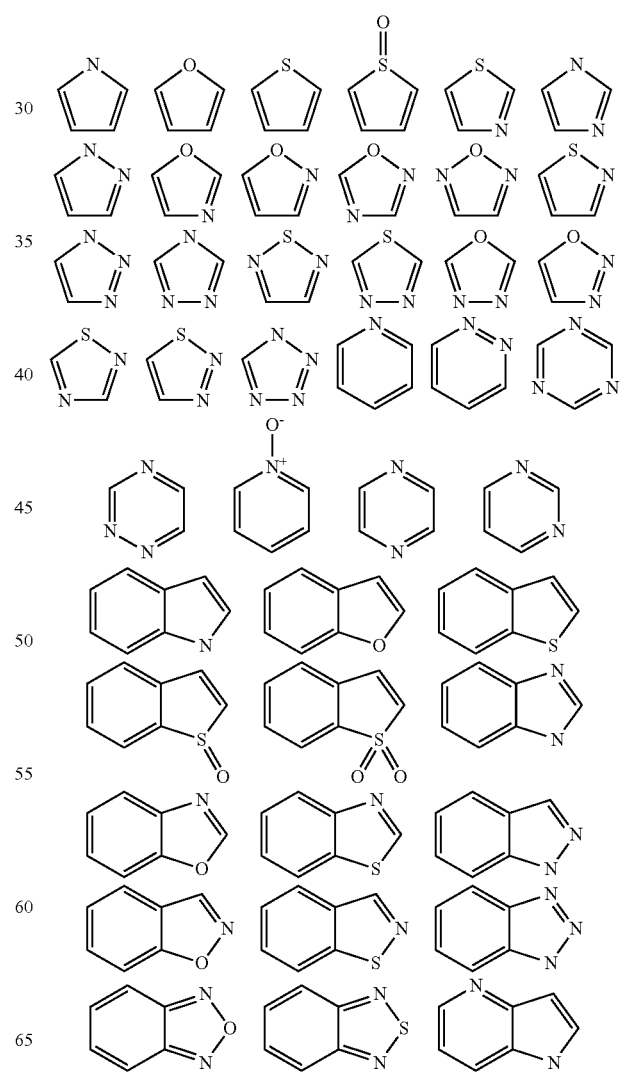

-continued

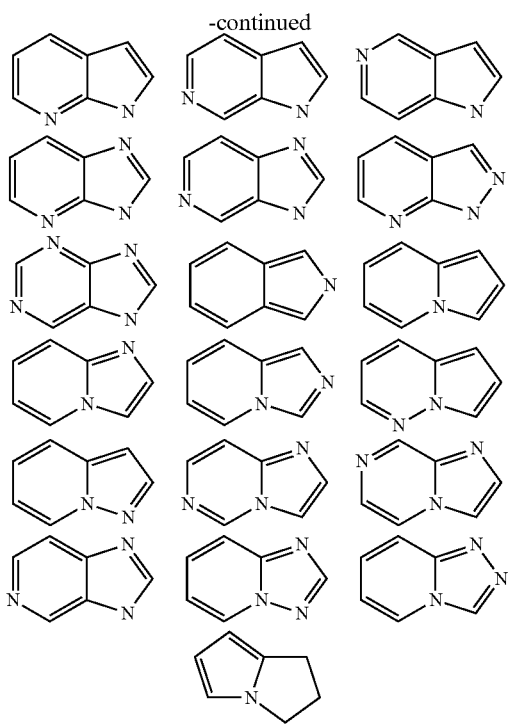

Preferred Embodiments

Preferred are the above compounds of formula 1, wherein $R^1$ is $R^{1.a}$ and $R^{1.a}$ is phenyl or pyridinyl; each ring optionally substituted by one, two or three residues independently selected from the group consisting of halogen, $O_2N$—, NC—, $H_2N$—, HO—, $R^{1.1}$, $R^{1.1}O$—, $R^{1.2}$, $R^{1.3}S$—, $R^{1.3}(O)S$— and $R^{1.3}(O)_2S$—.

Preferred are the above compounds of formula 1, wherein $R^1$ is $R^{1.b}$ and $R^{1.b}$ is phenyl or pyridinyl; each ring optionally substituted by one, two or three residues independently selected from the group consisting of halogen, NC—, $R^{1.1}$, $R^{1.3}(O)S$— and, $R^{1.3}(O)_2S$—. Preferred are the above compounds of formula 1, wherein $R^1$ is $R^{1.c}$ and $R^{1.c}$ is phenyl or pyridinyl; each ring optionally substituted by one, two or three residues independently selected from the group consisting of F, Cl, Br—, NC—, $R^{1.1}$, $R^{1.3}(O)S$— and $R^{1.3}(O)_2S$—, and $R^{1.1}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{1.2}$ is HO—$C_{1-6}$-alkyl- or $R^{1.1}$—O—$C_{1-6}$-alkyl-;

$R^{1.3}$ is independently selected from the group consisting of H, HO—, $R^{1.1}$ and $R^{1.2}$;

Preferred are the above compounds of formula 1, wherein $R^1$ is $R^{1.d}$ and $R^{1.d}$ is phenyl or pyridinyl; each ring optionally substituted by one, two or three residues independently selected from the group consisting of F, Cl, Br—, NC—, Me, Et, i-Pr, t-Bu, cyclopropyl, Me(O)S—, Me(O)$_2$S—, Et(O)$_2$S—, i-Pr(O)$_2$S—, t-Bu(O)$_2$S— and cyclopropyl(O)$_2$S—. Particularly preferred are the above compounds of formula 1, wherein $R^1$ is $R^{1.d}$ and $R^{1.d}$ is phenyl or pyridinyl; each ring optionally substituted by one, two or three residues independently selected from the group consisting of F, Cl, Br—, NC—, Me, Me(O)S—, Me(O)$_2$S— and Et(O)$_2$S—.

Preferred are the above compounds of formula 1, wherein $R^1$ is $R^{1.e}$ and $R^{1.e}$ is phenyl or pyridinyl; each ring optionally substituted by one or two residues independently selected from the group consisting of NC—, Me(O)S—, Me(O)$_2$S and Et(O)$_2$S.

Preferred are the above compounds of formula 1, wherein $R^1$ is $R^{1.f}$ and $R^{1.f}$ is

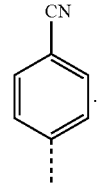

Preferred are the above compounds of formula 1, wherein $R^1$ is $R^{1.g}$ and $R^{1.g}$ is

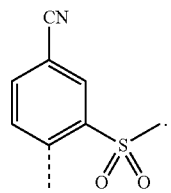

Preferred are the above compounds of formula 1, wherein $R^1$ is $R^{1.h}$ and $R^{1.h}$ is

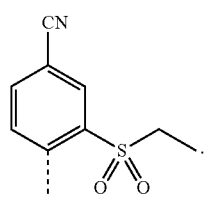

Preferred are the above compounds of formula 1, wherein $R^1$ is $R^{1.i}$ and $R^{1.i}$ is

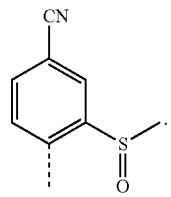

Preferred are the above compounds of formula 1, wherein $R^1$ is $R^{1.j}$ and $R^{1.j}$ is

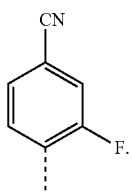

Preferred are the above compounds of formula 1, wherein $R^2$ is $R^{2.a}$ and $R^{2.a}$ is phenyl or a six-membered heteroaryl;

wherein one or two elements are replaced by an element independently selected from the group consisting of N, O and S; each ring optionally substituted with a substituent independently selected from the group consisting of halogen, $C_{1-4}$-alkyl-, $C_{1-4}$-haloalkyl- and $C_{1-4}$-alkyl-O—.

Preferred are the above compounds of formula 1, wherein $R^2$ is $R^{2.b}$ and $R^{2.b}$ is phenyl or a six-membered heteroaryl; wherein one or two elements are replaced by N; each ring optionally substituted with a substituent independently selected from the group consisting of halogen, $C_{1-4}$-alkyl- and $C_{1-4}$-haloalkyl-.

Preferred are the above compounds of formula 1, wherein $R^2$ is $R^{2.c}$ and $R^{2.c}$ is phenyl or pyridinyl; each optionally substituted with a substituent independently selected from the group consisting of halogen, $C_{1-4}$-alkyl- and $C_{1-4}$-haloalkyl-.

Preferred are the above compounds of formula 1, wherein $R^2$ is $R^{2.d}$ and $R^{2.d}$ is phenyl or pyridinyl; each optionally substituted with a substituent independently selected from among $F_3C$—, $F_2HC$— and $FH_2C$—.

Particularly preferred are the above compounds of formula 1, wherein $R^2$ is $R^{2.d}$ and $R^{2.d}$ is phenyl or pyridinyl; each optionally substituted with a substituent independently selected from among $F_3C$— and $F_2HC$—.

Preferred are the above compounds of formula 1, wherein $R^2$ is $R^{2.d}$ and $R^{2.d}$ is phenyl, optionally substituted with a substituent independently selected from the group consisting of $F_3C$— and $F_2HC$—.

Preferred are the above compounds of formula 1, wherein $R^2$ is $R^{2.f}$ and $R^{2.f}$ is pyridinyl, optionally substituted with a substituent independently selected from the group consisting of $F_3C$— and $F_2HC$—.

In a preferred embodiment of the invention $R^2$ is one of the above mentioned rings carrying the above mentioned substituent in meta-position to the connection of $R^2$ with the compound of formula 1.

Preferred are the above compounds of formula 1, wherein $R^2$ is $R^{2.g}$ and $R^{2.g}$ is

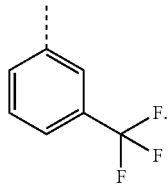

Preferred are the above compounds of formula 1, wherein $R^2$ is $R^{2.h}$ and $R^{2.h}$ is

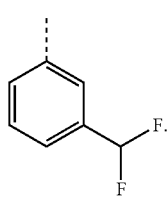

Preferred are the above compounds of formula 1, wherein $R^2$ is $R^{2.i}$ and $R^{2.i}$ is

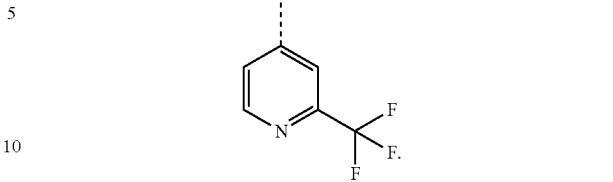

Preferred are the above compounds of formula 1, wherein $R^3$ is $R^{3.a}$ and $R^{3.a}$ is selected from the group consisting of $R^{3.1}$—;

$R^{3.2}O(O)C$—;

$R^{3.2}O(O)C$—$CH_2$—;

$R^{3.2}(O)_2S$—;

$(R^{3.2})_2N(O)C$— and $(R^{3.2})_2N(O)C$—$CH_2$—.

Preferred are the above compounds of formula 1, wherein $R^3$ is $R^{3.b}$ and $R^{3.b}$ is selected from the group consisting of $R^{3.1}$—;

$R^{3.2}O(O)C$—;

$R^{3.2}O(O)C$—$C$—$H_2$—;

$R^{3.2}(O)_2S$—;

$(R^{3.2})_2N(O)C$— and $(R^{3.2})_2N(O)C$—$CH_2$—.

Preferred are the above compounds of formula 1, wherein $R^3$ is independently selected from among $HO(O)C$—$H_2C$—, $MeO(O)C$—$H_2C$—, $H_2N(O)C$—$H_2C$—, $MeHN(O)C$—$H_2C$—, $Me_2N(O)C$—$H_2C$—, morpholinyl-$(O)C$—$H_2C$—, azetidinyl-$(O)C$—$H_2C$—, pyrrolidinyl-$(O)C$—$H_2C$—, $MeHN(O)C$—, $EtHN(O)C$—, $HO(CH_2)_2HN(O)C$—, $HO(CMe_2)(CH_2)HN(O)C$—, $HO(CH_2)_3HN(O)C$—, $Me(O)S(CH_2)_2HN(O)C$—, $Me(O)_2S(CH_2)_2HN(O)C$—, $Et(O)_2S$— and $Me(O)_2S$—.

Preferred are the above compounds of formula 1, wherein $R^3$ is independently selected from among $HO(O)C$—$H_2C$—, $MeO(O)C$—$H_2C$—, $H_2N(O)C$—$H_2C$—, $MeHN(O)C$—$H_2C$—, $Me_2N(O)C$—$H_2C$—, morpholinyl-$(O)C$—$H_2C$—, azetidinyl-$(O)C$—$H_2C$— and pyrrolidinyl-$(O)C$—$H_2C$—.

Preferred are the above compounds of formula 1, wherein $R^3$ is independently selected from among $MeHN(O)C$—, $EtHN(O)C$—, $HO(CH_2)_2HN(O)C$—, $HO(CMe_2)(CH_2)HN(O)C$—, $HO(CH_2)_3HN(O)C$—, $Me(O)S(CH_2)_2HN(O)C$— and $Me(O)_2S(CH_2)_2HN(O)C$—.

Preferred are the above compounds of formula 1, wherein $R^3$ is selected from among the examples (E#) 1 to 59 of Table 1 $R^3$—Embodiments of the invention for $R^3$, $R^{3.2}$, $R^{3.3}$, $R^{3.4}$, $R^{3.5}$, $R^{3.6}$, $R^{3.7}$, $R^{3.8}$ (if present):

TABLE 1

| | | $R^3$ - Embodiments of the invention | | | | | | |
|---|---|---|---|---|---|---|---|---|
| E# | $R^3$ | $R^{3.2}$ | $R^{3.3}$ | $R^{3.4}$ | $R^{3.5}$ | $R^{3.6}$ | $R^{3.7}$ | $R^{3.8}$ |
| 1. | $R^{3.1.a}$ | | $R^{3.3.a}$ | $R^{3.4.b}$ | $R^{3.5.b}$ | $R^{3.6.b}$ | $R^{3.7.b}$ | |
| 2. | $R^{3.1.b}$ | | $R^{3.3.a}$ | $R^{3.4.b}$ | | | | |
| 3. | $R^{3.1.c}$ | | $R^{3.3.a}$ | $R^{3.4.b}$ | $R^{3.5.b}$ | $R^{3.6.b}$ | $R^{3.7.b}$ | $R^{3.8.b}$ |

TABLE 1-continued

R³ - Embodiments of the invention

| E# | R³ | R³·² | R³·³ | R³·⁴ | R³·⁵ | R³·⁶ | R³·⁷ | R³·⁸ |
|---|---|---|---|---|---|---|---|---|
| 4. | $R^{3.1.d}$ | | $R^{3.3.a}$ | $R^{3.4.b}$ | $R^{3.5.b}$ | $R^{3.6.b}$ | $R^{3.7.b}$ | |
| 5. | H | | | | | | | |
| 6. | Me | | | | | | | |
| 7. | —CH₂—CN | | | | | | | |
| 8. | $R^{3.2}$O(O)C— | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |
| 9. | $R^{3.2}$O(O)C— | $R^{3.2.b}$ | $R^{3.3.a}$ | $R^{3.4.b}$ | | | | |
| 10. | $R^{3.2}$O(O)C— | $R^{3.2.c}$ | | | | | | |
| 11. | $R^{3.2}$O(O)C— | $R^{3.2.d}$ | $R^{3.3.a}$ | $R^{3.4.b}$ | $R^{3.5.b}$ | $R^{3.6.b}$ | $R^{3.7.b}$ | $R^{3.8.b}$ |
| 12. | $R^{3.2}$O(O)C— | $R^{3.2.h}$ | | | | | | |
| 13. | $R^{3.2}$O(O)C—CH₂—; | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |
| 14. | $R^{3.2}$O(O)C—CH₂—; | $R^{3.2.b}$ | $R^{3.3.a}$ | $R^{3.4.b}$ | | | | |
| 15. | $R^{3.2}$O(O)C—CH₂—; | $R^{3.2.c}$ | | | | | | |
| 16. | $R^{3.2}$O(O)C—CH₂—; | $R^{3.2.d}$ | $R^{3.3.a}$ | $R^{3.4.b}$ | $R^{3.5.b}$ | $R^{3.6.b}$ | $R^{3.7.b}$ | $R^{3.8.b}$ |
| 17. | $R^{3.2}$O(O)C—CH₂—; | $R^{3.2.h}$ | | | | | | |
| 18. | $R^{3.2}$(O)₂S—; | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |
| 19. | $R^{3.2}$(O)₂S—; | $R^{3.2.b}$ | $R^{3.3.a}$ | $R^{3.4.b}$ | | | | |
| 20. | $R^{3.2}$(O)₂S—; | $R^{3.2.c}$ | | | | | | |
| 21. | $R^{3.2}$(O)₂S—; | $R^{3.2.d}$ | $R^{3.3.a}$ | $R^{3.4.b}$ | $R^{3.5.b}$ | $R^{3.6.b}$ | $R^{3.7.b}$ | $R^{3.8.b}$ |
| 22. | $R^{3.2}$(O)₂S—; | Me; | | | | | | |
| 23. | $R^{3.2}$(O)₂S—; | $R^{3.2.h}$ | | | | | | |
| 24. | $R^{3.2}$HN(O)C— | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |
| 25. | $R^{3.2}$HN(O)C— | $R^{3.2.b}$ | $R^{3.3.a}$ | $R^{3.4.b}$ | | | | |
| 26. | $R^{3.2}$HN(O)C— | $R^{3.2.c}$ | | | | | | |
| 27. | $R^{3.2}$HN(O)C— | $R^{3.2.d}$ | $R^{3.3.a}$ | $R^{3.4.b}$ | $R^{3.5.b}$ | $R^{3.6.b}$ | $R^{3.7.b}$ | $R^{3.8.b}$ |
| 28. | $R^{3.2}$HN(O)C— | $R^{3.2.h}$ | | | | | | |
| 29. | $R^{3.2}$HN(O)C— | H | | | | | | |
| 30. | $R^{3.2}$HN(O)C— | Me | | | | | | |
| 31. | $R^{3.2}$HN(O)C— | Et | | | | | | |
| 32. | $R^{3.2}$HN(O)C— | cyclo-Pr | | | | | | |
| 33. | $R^{3.2}$HN(O)C— | HO(CH₂)₂— | | | | | | |
| 34. | $R^{3.2}$HN(O)C— | HO(CMe₂)CH₂— | | | | | | |
| 35. | $R^{3.2}$HN(O)C— | HO(CH₂)₃— | | | | | | |
| 36. | $R^{3.2}$HN(O)C—CH₂— | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |
| 37. | $R^{3.2}$HN(O)C—CH₂— | $R^{3.2.b}$ | $R^{3.3.a}$ | $R^{3.4.b}$ | | | | |
| 38. | $R^{3.2}$HN(O)C—CH₂— | $R^{3.2.c}$ | | | | | | |
| 39. | $R^{3.2}$HN(O)C—CH₂— | $R^{3.2.d}$ | $R^{3.3.a}$ | $R^{3.4.b}$ | $R^{3.5.b}$ | $R^{3.6.b}$ | $R^{3.7.b}$ | $R^{3.8.b}$ |
| 40. | $R^{3.2}$HN(O)C—CH₂— | $R^{3.2.h}$ | | | | | | |
| 41. | $(R^{3.2})_2$N(O)C— | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |
| 42. | $(R^{3.2})_2$N(O)C— | $R^{3.2.b}$ | $R^{3.3.a}$ | $R^{3.4.b}$ | | | | |
| 43. | $(R^{3.2})_2$N(O)C— | $R^{3.2.e}$ | $R^{3.3.a}$ | $R^{3.4.b}$ | $R^{3.5.b}$ | $R^{3.6.b}$ | $R^{3.7.b}$ | $R^{3.8.b}$ |
| 44. | $(R^{3.2})_2$N(O)C— | $R^{3.2.f}$ | $R^{3.3.a}$ | $R^{3.4.b}$ | $R^{3.5.b}$ | $R^{3.6.b}$ | $R^{3.7.b}$ | $R^{3.8.b}$ |
| 45. | $(R^{3.2})_2$N(O)C— | $R^{3.2.g}$ | $R^{3.3.a}$ | $R^{3.4.b}$ | $R^{3.5.b}$ | $R^{3.6.b}$ | $R^{3.7.b}$ | $R^{3.8.b}$ |
| 46. | $(R^{3.2})_2$N(O)C—CH₂— | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |
| 47. | $(R^{3.2})_2$N(O)C—CH₂— | $R^{3.2.b}$ | $R^{3.3.a}$ | $R^{3.4.b}$ | | | | |
| 48. | $(R^{3.2})_2$N(O)C—CH₂— | $R^{3.2.c}$ | | | | | | |
| 49. | $(R^{3.2})_2$N(O)C—CH₂— | $R^{3.2.d}$ | $R^{3.3.a}$ | $R^{3.4.b}$ | $R^{3.5.b}$ | $R^{3.6.b}$ | $R^{3.7.b}$ | $R^{3.8.b}$ |
| 50. | $(R^{3.2})_2$N(O)C—CH₂— | $R^{3.2.e}$ | $R^{3.3.a}$ | $R^{3.4.b}$ | $R^{3.5.b}$ | $R^{3.6.b}$ | $R^{3.7.b}$ | $R^{3.8.b}$ |
| 51. | $(R^{3.2})_2$N(O)C—CH₂— | $R^{3.2.f}$ | $R^{3.3.a}$ | $R^{3.4.b}$ | $R^{3.5.b}$ | $R^{3.6.b}$ | $R^{3.7.b}$ | $R^{3.8.b}$ |
| 52. | $(R^{3.2})_2$N(O)C—CH₂— | $R^{3.2.g}$ | $R^{3.3.a}$ | $R^{3.4.b}$ | $R^{3.5.b}$ | $R^{3.6.b}$ | $R^{3.7.b}$ | $R^{3.8.b}$ |
| 53. | Me(O)₂S— | | | | | | | |
| 54. | MeHN(O)C— | | | | | | | |
| 55. | EtHN(O)C— | | | | | | | |
| 56. | cyclo-PrHN(O)C— | | | | | | | |
| 57. | HO(CH₂)₂HN(O)C— | | | | | | | |
| 58. | HO(CMe₂)(CH₂)—HN(O)C—; | | | | | | | |
| 59. | HO(CH₂)₃HN(O)C— | | | | | | | |

Preferred are the above compounds of formula 1, wherein $R^{3.1}$ is $R^{3.1.a}$ and $R^{3.1.a}$ is H, $R^{3.3}$, $R^{3.4}$, $C_{1-6}$-alkyl-$C_{3-6}$-cycloalkyl-, $C_{3-6}$-cycloalkyl-$C_{1-6}$-alkyl-, each optionally substituted with one or two substituents independently selected from $R^{3.1.1}$—; and $R^{3.1.1}$ is selected from among HO—, halogen, NC—, $R^{3.3}$O—, $R^{3.5}$, $R^{3.6}$ and $R^{3.7}$.

Preferred are the above compounds of formula 1, wherein $R^{3.1}$ is $R^{3.1.b}$ and $R^{3.1.b}$ is selected from among H, $R_{3.3}$, $R^{3.4}$, $C_{1-6}$-alkyl-$C_{3-6}$-cycloalkyl- and $C_{3-6}$-cycloalkyl-$C_{1-6}$-alkyl-.

Preferred are the above compounds of formula 1, wherein $R^{3.1}$ is $R^{3.1.c}$ and $R^{3.1.c}$ is selected from among H, $R^{3.4}$ and $C_{1-6}$-alkyl-, optionally substituted with one or two substituents independently selected from $R^{3.1.1}$—; and $R^{3.1.1}$ is a ring independently selected from among phenyl and a four-membered heterocyclic ring containing one element independently selected from among N, O, S, S(O) and S(O)₂; or $R^{3.1.1}$ denotes a five- or six-membered heterocyclic or heteroaryl ring containing one, two or three elements independently selected from among N, O, S, S(O) and S(O)₂;

each of the rings optionally substituted with one or two substituents independently selected from among HO—, O═, halogen, NC—, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$.

Preferred are the above compounds of formula 1, wherein $R^{3.1}$ is $R^{3.1.d}$ and $R^{3.1.d}$ is independently selected from among H, $R^{3.4}$ and $C_{1-6}$-alkyl-, optionally substituted with one or two substituents independently selected from among $R^{3.1.1}$—; and $R^{3.1.1}$ is a ring independently selected from among phenyl and a five- or six-membered heterocyclic or heteroaryl ring containing one, two or three elements independently selected from among N, O, S, S(O) and S(O)$_2$;

each of the rings optionally substituted with one or two substituents independently selected from HO—, O=, halogen, NC—, $R^{3.3}$, $R^{3.3}$O—, $R^{3.3}$—(O)C—, $R^{3.4}$, $R^{3.5}$, $R^{3.6}$ and $R^{3.7}$.

Preferred are the above compounds of formula 1, wherein $R^{3.2}$ is $R^{3.2.a}$ and $R^{3.2.a}$ is $R^{3.1.a}$.

Preferred are the above compounds of formula 1, wherein $R^{3.2}$ is $R^{3.2.b}$ and $R^{3.2.b}$ is $R^{3.1.b}$.

Preferred are the above compounds of formula 1, wherein $R^{3.2}$ is $R^{3.2.c}$ and $R^{3.2.c}$ is phenyl.

Preferred are the above compounds of formula 1, wherein $R^{3.2}$ is $R^{3.2.d}$ and $R^{3.2.d}$ is a five- or six-membered heterocyclic or heteroaryl ring containing one, two or three elements independently selected from among N, O, S, S(O) and S(O)$_2$; each ring optionally substituted with one or two substituents independently selected from among HO—, O=, NC—, halogen, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$.

Preferred are the above compounds of formula 1, wherein $R^{3.2}$ is $R^{3.2.e}$ and two $R^{3.2.e}$ are together a three-, four-, five- or six-membered monocyclic or a six-, seven-, eight-, nine- or ten-membered bicyclic heterocyclic or heterocyclic ring optionally containing additional to the nitrogen one or two elements independently selected from among N, O, S, S(O) and S(O)$_2$; optionally substituted with one or two substituents, independently selected from among HO—, F, O=, NC—, $R^{3.3}$, $R^{3.3}$O—, $R^{3.3}$—(O)C—, $R^{3.4}$, $R^{3.5}$, $R^{3.7}$ and $R^{3.6}$ or two substituents are together $R^{3.8}$.

Preferred are the above compounds of formula 1, wherein $R^{3.2}$ is $R^{3.2.f}$ and two $R^{3.2.f}$ are together a three-, four-, five- or six-membered heterocyclic or heteroaryl ring optionally containing additional to the nitrogen one or two elements independently selected from among N, O, S, S(O) and S(O)$_2$; optionally substituted with one or two substituents, independently selected from the group consisting of HO—, F, O=, NC—, $R^{3.3}$, $R^{3.3}$O—, $R^{3.3}$—(O)C—, $R^{3.4}$, $R^{3.5}$, $R^{3.7}$, $R^{3.6}$ or two substituents are together $R^{3.8}$.

Preferred are the above compounds of formula 1, wherein $R^{3.2}$ is $R^{3.2.g}$ and two $R^{3.2.g}$ are together a six-, seven-, eight-, nine- or ten-membered bicyclic heterocyclic or heteroaryl ring optionally containing additional to the nitrogen one or two elements independently selected from the group consisting of N, O, S, S(O) and S(O)$_2$; optionally substituted with one or two substituents, independently selected from the group consisting of HO—, F, O=, NC—, $R^{3.3}$, $R^{3.3}$O—, $R^{3.3}$—(O)C—, $R^{3.4}$, $R^{3.5}$, $R^{3.7}$ and $R^{3.6}$ or two substituents are together $R^{3.8}$.

Preferred are the above compounds of formula 1, wherein $R^{3.2}$ is $R^{3.2.h}$ and $R^{3.2.h}$ is selected from the group consisting of H, Me, Et, n-Pr, i-Pr and cyclopropyl.

Preferred are the above compounds of formula 1, wherein $R^{3.3}$ is $R^{3.3.a}$ and $R^{3.3.a}$ is selected from the group consisting of Me, Et, n-Pr, i-Pr, n-Bu, t-Bu, cyclopropyl, cyclobutyl, cyclopentyl, cyclohexyl, F$_3$C—, F$_2$HC—, F$_3$C—CH$_2$—, F$_2$HC—CH$_2$— and FH$_2$C—CH$_2$—.

Preferred are the above compounds of formula 1, wherein $R^{3.4}$ is $R^{3.4.a}$ and $R^{3.4.a}$ is selected from the group consisting of HO—CH$_2$—, HO—CH$_2$—CH$_2$—, HO—CH$_2$—CH$_2$—CH$_2$—, $R^{3.3.a}$O—CH$_2$—, $R^{3.3.a}$O—CH$_2$—CH$_2$— and $R^{3.3}$O—CH$_2$—CH$_2$—CH$_2$—.

Preferred are the above compounds of formula 1, wherein $R^{3.4}$ is $R^{3.4.b}$ and $R^{3.4.b}$ is selected from the group consisting of HO—CH$_2$—, HO—CH$_2$—CH$_2$—, HO—CH$_2$—CH$_2$—CH$_2$—, MeO—CH$_2$—, MeO—CH$_2$—CH$_2$—, MeO—CH$_2$—CH$_2$—CH$_2$—, EtO-CH$_2$— EtO-CH$_2$—CH$_2$— and EtO-CH$_2$—CH$_2$—CH$_2$—.

Preferred are the above compounds of formula 1, wherein $R^{3.5}$ is $R^{3.5.a}$ and $R^{3.5.a}$ is selected from the group consisting of H$_2$N—, $R^{3.3.a}$HN—, $(R^{3.3.a})_2$N—, $R^{3.3.a}$(O)C—HN— and $R^{3.3.a}$—(O)C—$(R^{3.3.a})$N—.

Preferred are the above compounds of formula 1, wherein $R^{3.5}$ is $R^{3.5.b}$ and $R^{3.5.b}$ is selected from the group consisting of H$_2$N—, MeHN—, (Me)$_2$N—, EtHN-, (Et)$_2$N—, i-PrHN—, (i-Pr)(Me)N—, t-BuHN-, (t-Bu)(Me)N—, Me(O)C—HN—, Et(O)C—HN—, n-Pr(O)C—HN—, i-Pr(O)C—HN— and t-Bu(O)C—HN—.

Preferred are the above compounds of formula 1, wherein $R^{3.6}$ is $R^{3.6.a}$ and $R^{3.6.a}$ is selected from the group consisting of $R^{3.3.a}$(O)S—, $R^{3.3.a}$(O)$_2$S—, $R^{3.3.a}$(HN)S—, $R^{3.3.a}$(HN)(O)S—, $R^{3.3.a}$($R^{3.3.a}$N)S—, $R^{3.3.a}$($R^{3.3.a}$N)(O)S—, $R^{3.3.a}$($R^{3.4.a}$N)S—, $R^{3.3.a}$($R^{3.4.a}$N)(O)S—, $R^{3.3.a}$(NC—N)S— and $R^{3.3.a}$(NC—N)(O)S—.

Preferred are the above compounds of formula 1, wherein $R^{3.6}$ is $R^{3.6.b}$ and $R^{3.6.b}$ is selected from the group consisting of Me(O)S—, Et(O)S—, i-Pr(O)S—, Me(O)$_2$S—, Et(O)$_2$S—, i-Pr(O)$_2$S—, Me(HN)S—, Et(HN)S—, i-Pr(HN)S—, Me(HN)(O)S—, Et(HN)(O)S—, i-Pr(HN)(O)S—, Me(MeN)S—, Et(MeN)S—, i-Pr(MeN)S—, Me(MeN)(O)S—, Et(MeN)(O)S—, i-Pr(MeN)(O)S—, Me(HOCH$_2$CH$_2$N)S—, Et(HOCH$_2$CH$_2$N)S—, i-Pr(HOCH$_2$CH$_2$N)S—, Me(HOCH$_2$CH$_2$N)(O)S—, Et(HOCH$_2$CH$_2$N)(O)S—, i-Pr(HOCH$_2$CH$_2$N)(O)S—, Me(MeOCH$_2$CH$_2$N)S—, Et(MeOCH$_2$CH$_2$N)S—, i-Pr(MeOCH$_2$CH$_2$N)S—, Me(MeOCH$_2$CH$_2$N)(O)S—, Et(MeOCH$_2$CH$_2$N)(O)S— and i-Pr(MeOCH$_2$CH$_2$N)(O)S—, Preferred are the above compounds of formula 1, wherein $R^{3.7}$ is $R^{3.7.a}$ and $R^{3.7.a}$ is selected from the group consisting of HO(O)C—, H$_2$N(O)C—, $R^{3.3.a}$O(O)C—, $R^{3.3.a}$NH(O)C— and $(R^{3.3.a})_2$N(O)C—.

Preferred are the above compounds of formula 1, wherein $R^{3.7}$ is $R^{3.7.b}$ and $R^{3.7.b}$ is selected from the group consisting of HO(O)C—, H$_2$N(O)C—, MeO(O)C—, EtO(O)C—, i-PrO(O)C—, t-BuO(O)C—, MeNH(O)C—, EtNH(O)C—, i-PrNH(O)C—, t-BuNH(O)C—, (Me)$_2$N(O)C—, (Et)$_2$N(O)C—, (i-Pr)(Me)N(O)C—, (t-Bu)(Me)N(O)C—, Et(Me)N(O)C—, i-Pr(Me)N(O)C— and t-Bu(Me)N(O)C—.

Preferred are the above compounds of formula 1, wherein $R^{3.8}$ is $R^{3.8.a}$ and $R^{3.8.a}$ is independently selected from the group consisting of —CH$_2$—, —CH$_2$CH$_2$—, —CH$_2$CH$_2$CH$_2$—, —CH$_2$CH$_2$CH$_2$CH$_2$— and —CH$_2$CH$_2$CH$_2$CH$_2$CH$_2$—, wherein optionally one or two CH$_2$-groups are independently replaced by a group selected from among —HN—, -MeN—, -EtN-, -(Me(O)C—)N—, -(Et(O)C—)N—, -(MeO(O)C—)N—, -(EtO(O)C—)N—, —O—, —S—, —S(O)— and —S(O)$_2$—.

Preferred are the above compounds of formula 1, wherein $R^{3.8}$ is $R^{3.8.b}$ and $R^{3.8.b}$ is selected from the group consisting of —CH$_2$—, —CH$_2$CH$_2$—, —CH$_2$CH$_2$CH$_2$—, —CH$_2$CH$_2$CH$_2$CH$_2$— and —CH$_2$CH$_2$CH$_2$CH$_2$CH$_2$—, wherein optionally one or two CH$_2$-groups are independently replaced by a group selected from among —HN—, -MeN—, -EtN-, —O—, —S—, —S(O)— and —S(O)$_2$—.

Preferred are the above compounds of formula 1, wherein A is $A^a$ and $A^a$ is —CH$_2$—, optionally substituted with one or two substituents independently selected from the group consisting of halogen, $R^{3.3}$, $R^{3.3}O$— and $R^{3.4}$ or two substituents together are —$CH_2CH_2$—.

Preferred are the above compounds of formula 1, wherein A is $A^b$ and $A^b$ is —$CH_2$—, optionally substituted with one or two substituents independently selected from the group consisting of F, Me, Et, i-Pr, MeO, EtO, $HOCH_2O$— and $MeOCH_2$—.

Preferred are the above compounds of formula 1, wherein A is $A^c$ and $A^c$ is —$CH_2$— or —CHMe-.

Preferred are the above compounds of formula 1, wherein A is $A^d$ and $A^d$ is —$CH_2$—.

Preferred are the above compounds of formula 1, wherein $R^4$ is $R^{4.a}$ and $R^{4.a}$ is selected from the group consisting of halogen, $C_{1-6}$-alkyl-, $C_{3-6}$-cycloalkyl-, $C_{1-6}$-haloalkyl- and $C_{3-6}$-halocycloalkyl.

Preferred are the above compounds of formula 1, wherein $R^4$ is $R^{4.b}$ and $R^{4.b}$ is F, Me.

Preferred are the above compounds of formula 1, wherein $R^4$ is $R^{4.c}$ and $R^{4.c}$ is $C_{1-6}$-alkyl-. Particularly preferred are the above compounds of formula 1, wherein $R^4$ is $R^{4.c}$ and $R^{4.c}$ is Me.

Preferred are the above compounds of formula 1, wherein m is 0.

Preferred is a compound of formula 1, wherein $R^1$ is $R^{1.b}$ and $R^{1.b}$ is phenyl or pyridinyl; each ring optionally substituted by one, two or three residues independently selected from the group consisting of halogen, NC—, $R^{1.1}$, $R^{1.3}(O)S$— and $R^{1.3}(O)_2S$—;

$R^2$ is $R^{2.b}$ and $R^{2.b}$ is phenyl or a six-membered heteroaryl; wherein one or two elements are replaced by N; each ring optionally substituted with a substituent independently selected from the group consisting of halogen, $C_{1-4}$-alkyl- and $R^3$ is a residue independently selected from the group consisting of $R^{3.1}$—;

$R^{3.2}O(O)C$— or $R^{3.2}O(O)C$—$CH_2$—;

$R^{3.2}(O)_2S$—;

$(R^{3.2})_2N(O)C$— and $(R^{3.2})_2N(O)C$—$CH_2$—.

$R^{3.1}$ is independently selected from the group consisting of H, $R^{3.3}$, $R^{3.4}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from $R^{3.1.1}$—;

$R^{3.1}$ is selected from the group consisting of HO—, halogen, NC—, $R^{3.3}O$—, $R^{3.5}$, $R^{3.6}$ and $R^{3.7}$ or $R^{3.1.1}$ denotes a ring independently selected from among phenyl and a four-membered heterocyclic ring containing one element independently selected from among N, O, S, S(O) and $S(O)_2$; or $R^{3.1.1}$ denotes a five- or six-membered heterocyclic or heteroaryl ring containing one, two or three elements independently selected from among N, O, S, S(O) and $S(O)_2$;

each of the rings as defined for $R^{3.1.1}$ is optionally substituted with one or two substituents independently selected from among HO—, O=, halogen, $R^{3.3}$, $R^{3.3}O$—, $R^{3.3}$—(O)C—, $R^{3.4}$, $R^{3.5}$, $R^{3.6}$ and $R^{3.7}$ or two substituents are together $R^{3.8}$;

$R^{3.2}$ is independently selected from $R^{3.1}$, phenyl or a five- or six-membered heterocyclic or heteroaryl ring containing one, two or three elements independently selected from among N, O, S, S(O) and $S(O)_2$; each ring optionally substituted with one or two substituents independently selected from among HO—, O=, NC—, halogen, $R^{3.3}$, $R^{3.3}O$—, $R^{3.3}$—(O)C—, $R^{3.4}$, $R^{3.5}$, $R^{3.6}$ and $R^{3.7}$ or two substituents are together $R^{3.8}$;

or two $R^{3.2}$ are together a five- or six-membered monocyclic or a eight-, nine- or ten-membered bicyclic heterocyclic or heteroaryl ring optionally containing additional to the nitrogen one or two elements independently selected from among N, O, S, S(O) and $S(O)_2$; optionally substituted with one or two substituents, independently selected from among HO—, F, O=, $R^{3.3}$, $R^{3.3}O$—, $R^{3.3}$—(O)C—, $R^{3.4}$, $R^{3.5}$, $R^{3.7}$ and $R^{3.6}$ or two substituents are together $R^{3.8}$;

$R^{3.3}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{3.4}$ is HO—$C_{1-6}$-alkyl- or $R^{3.3}$—O—$C_{1-6}$-alkyl-;

$R^{3.5}$ is independently selected from the group consisting of $H_2N$—, $R^{3.3}$—HN—, $(R^{3.3})_2N$— and $R^{3.3}$—(O)C—HN—;

$R^{3.6}$ is independently selected from the group consisting of $R^{3.3}$—(O)S—, $R^{3.3}$—(O)$_2$S—, $R^{3.3}$(HN)S—, $R^{3.3}$(HN)(O)S—$R^{3.3}(R^{3.3}N)S$—, $R^{3.3}(R^{3.3}N)(O)S$—, $R^{3.3}(R^{3.4}N)S$— and $R^{3.3}(R^{3.4}N)(O)S$—;

$R^{3.7}$ is independently selected from the group consisting of HO(O)C—, $H_2N(O)C$—, $R^{3.3}$—O—(O)C—, $R^{3.3}$—NH—(O)C— and $(R^{3.3})_2N$—(O)C—;

$R^{3.8}$ is independently selected from the group consisting of $C_{1-6}$-alkylene or $C_{1-6}$-haloalkylene, wherein optionally one or two $CH_2$-groups are replaced by a group selected from among —HN—, —$(R^{3.3})N$—, —$(R^{3.4})N$—, —$R^{3.3}(O)C$—)N—, —$(R^{3.4}(O)C$—)N—, —O—, —S—, S(O)— and —$S(O)_2$—;

$R^4$ is independently selected from among halogen and $C_{1-6}$-alkyl-.

m is 0, 1 or 2; preferably 0;

or a salt thereof.

Preferred is a compound of formula 1, wherein $R^1$ is $R^{1.d}$ and $R^{1.d}$ is phenyl or pyridinyl; each ring optionally substituted by one, two or three residues independently selected from the group consisting of F, Cl, Br—, NC—, Me, $Me(O)_2S$—, $Et(O)_2S$— and Me(O)S—.

$R^2$ is $R^{2.c}$ and $R^{2.c}$ is phenyl or pyridinyl; each optionally substituted with a substituent independently selected from the group consisting of halogen, $C_{1-4}$-alkyl- and $C_{1-4}$-haloalkyl-;

$R^3$ is selected of the examples (E#) 1 to 59 of the Table 1 $R^3$—Embodiments of the invention; or $R^3$ is independently selected from among $HO(O)C$—$H_2C$—, $MeO(O)C$—$H_2C$—, $H_2N(O)C$—$H_2C$—, $MeHN(O)C$—$H_2C$—, $Me_2N(O)C$—$H_2C$—, morpholinyl-(O)C—$H_2C$—, azetidinyl-(O)C—$H_2C$—, pyrrolidinyl-(O)C—$H_2C$—, MeHN(O)C—, EtHN(O)C—, $HO(CH_2)_2HN(O)C$— and $HO(CMe_2)(CH_2)HN(O)C$—;

$R^4$ is $C_{1-6}$-alkyl;

m is 0, 1 or 2;

or a salt thereof.

Preferred is a compound of formula 1, wherein $R^1$ is $R^{1.e}$ and $R^{1.e}$ is phenyl or pyridinyl; each ring optionally substituted by one or two residues independently selected from among NC—, Me(O)S—, $Me(O)_2S$ and $Et(O)_2S$;

$R^2$ is $R^{2.d}$ and $R^{2.d}$ is phenyl or pyridinyl; each optionally substituted with a substituent independently selected from the group consisting of $F_3C$— and $F_2HC$—;

$R^3$ is selected from among the examples (E#) 1 to 59 of the Table 1 $R^3$—Embodiments of the invention; or $R^3$ is independently selected from among HO(O)C—$H_2C$—, MeO(O)C—$H_2C$—, $H_2N(O)C$—$H_2C$—, MeHN(O)C—

H$_2$C—, Me$_2$N(O)C—H$_2$C—, morpholinyl-(O)C—H$_2$C—, azetidinyl-(O)C—H$_2$C—, pyrrolidinyl-(O)C—H$_2$C—, MeHN(O)C—, EtHN(O)C—, HO(CH$_2$)$_2$HN(O)C—, HO(CMe$_2$)(CH$_2$)HN(O)C—, HO(CH$_2$)$_3$HN(O)C—, Me(O)S(CH$_2$)$_2$HN(O)C—, Me(O)$_2$S(CH$_2$)$_2$HN(O)C—, Et(O)$_2$S— and Me(O)$_2$S—.

m is 0;

or a salt thereof.

Preferred is a compound of formula 1, wherein

R$^1$ is R$^{1.e}$ and R$^{1.e}$ is phenyl or pyridinyl; each ring optionally substituted by one or two residues independently selected from among NC—, Me(O)S—, Me(O)$_2$S and Et(O)$_2$S;

R$^2$ is R$^{2.d}$ and R$^{2.d}$ is phenyl or pyridinyl; each optionally substituted with a substituent independently selected from among F$_3$C— and F$_2$HC—;

R$^3$ is one of the examples (E#) 2, 4, 5, 6, 7, 11, 12, 16, 17, 21, 22, 23, 27, 28, 29, 30, 31, 32, 33, 37, 43, 48 selected from among the examples of the Table 1 R$^3$—Embodiments of the invention; or R$^3$ is independently selected from among HO(O)C—H$_2$C—, MeO(O)C—H$_2$C—, H$_2$N(O)C—H$_2$C—, MeHN(O)C—H$_2$C—, Me$_2$N(O)C—H$_2$C—, morpholinyl-(O)C—H$_2$C—, azetidinyl-(O)C—H$_2$C—, pyrrolidinyl-(O)C—H$_2$C—, MeHN(O)C—, EtHN(O)C—, HO(CH$_2$)$_2$HN(O)C—, HO(CMe$_2$)(CH$_2$)HN(O)C—, HO(CH$_2$)$_3$HN(O)C—, Me(O)S(CH$_2$)$_2$HN(O)C—, Me(O)$_2$S(CH$_2$)$_2$HN(O)C—, Et(O)$_2$S— and Me(O)$_2$S—.

m is 0;

or a salt thereof.

Preferred is a compound of formula 1, wherein

R$^1$ is R$^{1.e}$ and R$^{1.e}$ is phenyl or pyridinyl; each ring optionally substituted by one or two residues independently selected from among NC—, Me(O)S—, Me(O)$_2$S and Et(O)$_2$S;

R$^2$ is R$^{2.d}$ and R$^{2.d}$ is phenyl or pyridinyl; each optionally substituted with a substituent independently selected from the group consisting of F$_3$C— or F$_2$HC—;

R$^3$ is one of the examples (E#) 2, 5, 6, 11, 16, 17, 21, 22, 23, 27, 33, 37, 43, 48 selected from among the examples of the Table 1 R$^3$—Embodiments of the invention; or R$^3$ is independently selected from among HO(O)C—H$_2$C—, MeO(O)C—H$_2$C—, H$_2$N(O)C—H$_2$C—, MeHN(O)C—H$_2$C—, Me$_2$N(O)C—H$_2$C—, morpholinyl-(O)C—H$_2$C—, azetidinyl-(O)C—H$_2$C—, pyrrolidinyl-(O)C—H$_2$C—, MeHN(O)C—, EtHN(O)C—, HO(CH$_2$)$_2$HN(O)C—, HO(CMe$_2$)(CH$_2$)HN(O)C—, HO(CH$_2$)$_3$HN(O)C—, Me(O)S(CH$_2$)$_2$HN(O)C—, Me(O)$_2$S(CH$_2$)$_2$HN(O)C—, Et(O)$_2$S— and Me(O)$_2$S—.

m is 0;

or a salt thereof.

Preferred is a compound of formula 1, wherein R$^3$ is a residue independently selected from the group consisting of

R$^{3.1}$—;

R$^{3.2}$O(O)C— or R$^{3.2}$O(O)C—CH$_2$—;

R$^{3.2}$(O)$_2$S— and (R$^{3.2}$)$_2$N(O)C— or (R$^{3.2}$)$_2$N(O)C—CH$_2$—;

R$^{3.1}$ is independently selected from the group consisting of H, R$^{3.3}$, R$^{3.4}$, C$_{1-6}$-alkyl-C$_{3-6}$-cycloalkyl-, C$_{3-6}$-cycloalkyl-C$_{1-6}$-alkyl-, each optionally substituted with one or two substituents independently selected from R$^{3.1.1}$—;

R$^{3.1.1}$ is selected from the group consisting of HO—, halogen, NC—, R$^{3.3}$O—, R$^{3.5}$, R$^{3.6}$ and R$^{3.7}$ or R$^{3.1.1}$ denotes a ring independently selected from among phenyl and a four-membered heterocyclic ring containing one element independently selected from N, O, S, S(O) and S(O)$_2$;

R$^{3.1.1}$ denotes a five- or six-membered heterocyclic or heteroaryl ring containing one, two or three elements independently selected from N, O, S, S(O) and S(O)$_2$; each of the rings optionally substituted with one or two substituents independently selected from HO—, O═, halogen, R$^{3.3}$, R$^{3.3}$O—, R$^{3.3}$—(O)C—, R$^{3.4}$, R$^{3.5}$, R$^{3.6}$ and R$^{3.7}$ or two substituents are together R$^{3.8}$;

R$^{3.2}$ is independently selected from R$^{3.1}$, phenyl or a five- or six-membered heterocyclic or heteroaryl ring containing one, two or three elements independently selected from among N, O, S, S(O) and S(O)$_2$; each ring optionally substituted with one or two substituents independently selected from HO—, O═, NC—, halogen, R$^{3.3}$, R$^{3.3}$O—, R$^{3.3}$—(O)C—, R$^{3.4}$, R$^{3.5}$, R$^{3.6}$ and R$^{3.7}$ or two substituents are together R$^{3.8}$;

or two R$^{3.2}$ are together a five- or six-membered monocyclic or a eight-, nine- or ten-membered bicyclic heterocyclic or heteroaryl ring optionally containing additional to the nitrogen one or two elements independently selected from among N, O, S, S(O) and S(O)$_2$; optionally substituted with one or two substituents, independently selected from HO—, F, O═, R$^{3.3}$, R$^{3.3}$O—, R$^{3.3}$—(O)C—, R$^{3.4}$, R$^{3.5}$, R$^{3.7}$ and R$^{3.6}$ or two substituents are together R$^{3.8}$;

R$^{3.3}$ is independently selected from the group consisting of C$_{1-6}$-alkyl-, C$_{3-6}$-cycloalkyl-, C$_{1-6}$-haloalkyl- and C$_{3-6}$-halocycloalkyl;

R$^{3.4}$ is HO—C$_{1-6}$-alkyl- or R$^{3.3}$—O—C$_{1-6}$-alkyl-;

R$^{3.5}$ is independently selected from the group consisting of H$_2$N—, R$^{3.3}$—HN—, (R$^{3.3}$)$_2$N— and R$^{3.3}$—(O)C—HN—;

R$^{3.6}$ is independently selected from the group consisting of R$^{3.3}$—(O)S—, R$^{3.3}$—(O)$_2$S—, R$^{3.3}$(HN)S—, R$^{3.3}$(HN)(O)S—R$^{3.3}$(R$^{3.3}$N)S—, R$^{3.3}$(R$^{3.3}$N)(O)S—, R$^{3.3}$(R$^{3.4}$N)S— and R$^{3.3}$(R$^{3.4}$N)(O)S—;

R$^{3.7}$ is independently selected from the group consisting of HO(O)C—, H$_2$N(O)C—, R$^{3.3}$—O—(O)C—, R$^{3.3}$—NH—(O)C— and (R$^{3.3}$)$_2$N—(O)C—;

R$^{3.8}$ is independently selected from the group consisting of C$_{1-6}$-alkylene or C$_{1-6}$-haloalkylene, wherein optionally one or two CH$_2$-groups are replaced by —HN—, —(R$^{3.3}$)N—, —(R$^{3.4}$)N—, —(R$^{3.3}$(O)C—)N—, —(R$^{3.4}$(O)C—)N—, —O—, —S—, —S(O)— and —S(O)$_2$—;

or a salt therof.

Preferred is a compound of formula 1, wherein

R$^1$ is independently selected from the group consisting of formulas (a) to (d)

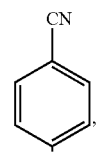
(a)

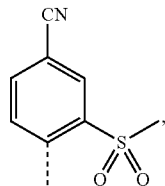
(b)

-continued (c) 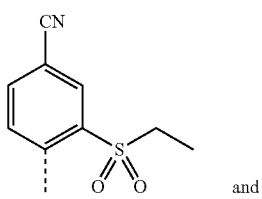

and (d) 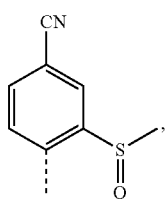

$R^2$ is independently selected from the group consisting of Phenyl-CF$_3$, Phenyl-CHF$_2$— and Pyridinyl-CF$_3$—, preferably selected from the group consisting of formulas (e) to (g)

(e) 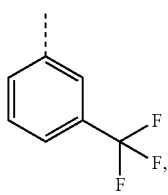

(f) 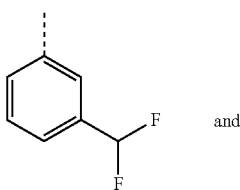

and (g) 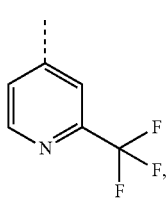

and $R^3$ is hydrogen or independently selected from the group consisting of Me, NC—CH$_2$—, Me(O)$_2$S—, MeHN(O)C—, EtHN(O)C—, cyclo-PrHN(O)C—, HO(CH$_2$)$_2$HN(O)C—, HO(CMe$_2$)(CH$_2$)HN(O)C— and HO(CH$_2$)$_3$HN(O)C—.

Preferred of all of the above mentioned embodiments of the invention is a compound of formula 1, wherein configuration of formula 1 is according to formula 1'

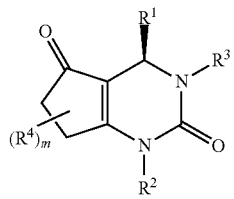

1' or a salt thereof.

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes. Starting materials are commercially available or may be prepared by methods that are described in the literature or herein, or may be prepared in an analogous or similar manner Any functional groups in the starting materials or intermediates may be protected using conventional protecting groups. These protecting groups may be cleaved again at a suitable stage within the reaction sequence using methods familiar to the one skilled in the art.

Compounds of the invention VI are accessible using the synthetic route illustrated in Scheme 1; $R^1$, $R^{E.1}$, $R^{E.2}$ have the meanings as defined hereinbefore and hereinafter.

SCHEME 1

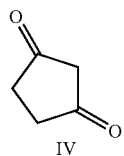

IV

↓ Step C

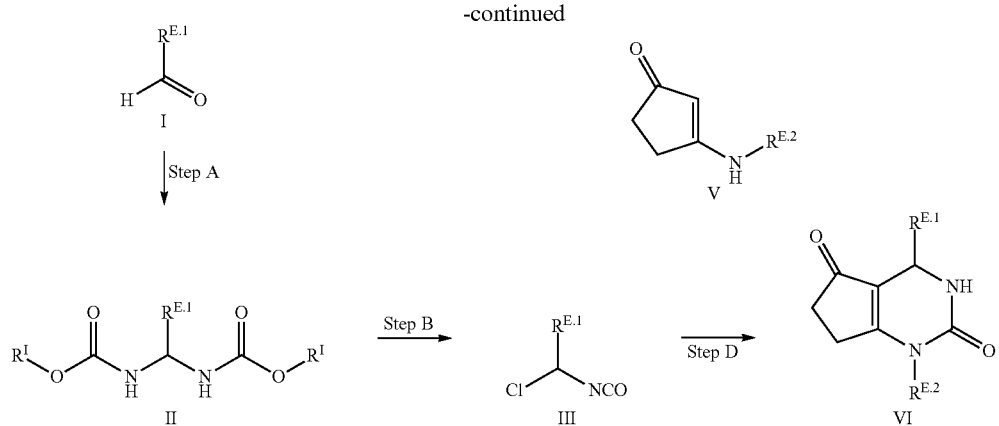

Intermediates II (Step A, intermediate I→intermediate II) can be prepared as described in Vovk et al. (*Synlett* 2006, 3, 375-378) or in PL2004/369318, by heating an aliphatic or aromatic aldehyde I with a carbamate, for example methyl carbamate, ethyl carbamate (urethane) or benzyl carbamate in the presence of a strong Brønsted or a Lewis acid, for example sulfuric acid, hydrogen chloride, p-toluenesulfonic acid, Amberlyst 15, tetrafluoro-boric acid, trifluoroacetic acid or boron trifluoride, either without solvent as a melt or in a suitable solvent, such as benzene, toluene, acetonitrile, diethyl ether, chloroform, acetic anhydride or mixtures thereof. The reaction takes place within 1 to 24 hours. Preferred reaction temperatures are between room temperature and 160° C., or the boiling point of the solvent, respectively. Preferably the reaction is done with molten ethyl carbamate as reactant and a catalytic amount of concentrated sulfuric acid at temperatures of 140-160° C. without any additional solvent.

The chlorination (Step B, intermediate II→intermediate III) can be done as described in Vovk et al. (*Synlett* 2006, 3, 375-378) and Sinitsa et al. (*J. Org. Chem. USSR* 1978, 14, 1107) by heating intermediate II together with a chlorinating agent, for example phosphorous pentachloride, phosphoryl chloride or sulfuryl chloride in an organic solvent, for example benzene or toluene. The reaction takes place within 1 to 24 hours. Preferred reaction temperatures are between 50° C. and 150° C.

Alternatively, intermediates III can be prepared as described in Jochims et al. (*Chem. Ber.* 1982, 115, 860-870) by α-halogenation of aliphatic isocyanates, for example benzyl iso-cyanate, using for example a bromination agent, for example N-bromosuccinimide Isocyanates can be synthesized as described in U.S. Pat. No. 6,207,665 and in Charalambides et al. (*Synth. Commun.* 2007, 37, 1037-1044), by reacting an amine precursor with phosgene.

Intermediates V (Step C, intermediate→IV intermediates V) can be prepared as described in Chen et al. (*Synth. Commun.* 2010, 40, 2506-2510) and Tietcheu et al. (*J. Heterocyclic Chem.* 2002, 39, 965-973) by reacting cyclopentane-1,3-dione (IV) and an aliphatic or aromatic amine in the presence of a catalyst, for example Ytterbium triflate [Yb(OTf)$_3$] or an acid, for example hydrogen chloride or p-toluenesulfonic acid, optionally in a solvent, for example water, acetic acid, acetonitrile, benzene, toluene. The reaction takes place within 1-24 hours. Preferred reaction temperatures are between room temperature and 120° C., most preferred room temperature.

Alternatively, intermediates V can be prepared as described in Scott et al. (*J. Med. Chem.* 1993, 36, 1947-1955) by direct condensation of the 1,3-dicarbonyl compound with an amine under reflux in a suitable solvent, for example benzene or toluene with azeotropic removal of water. Alternatively, intermediates V can be prepared as described in Mariano et al. (*J. Org. Chem.* 1984, 49, 220-228) by reacting an amine with 3-chloro-2-cyclopenten-1-one, which can be prepared from cyclopentane-1,3-dione.

Compounds according to the present invention (Step D, intermediates III→compounds of the invention VI) can be prepared as described in Vovk et al. (*Synlett* 2006, 3, 375-378), Vovk et al. (*Russ. J. Org. Chem.* 2010, 46, 709-715) and Kushnir et al. (*Russ. J. Org. Chem.* 2011, 47, 1727-1732) by reacting intermediates III with intermediates V in an organic solvent, for example dichloromethane, chloroform, benzene or toluene. The reaction takes place within 1-24 hours. Preferred reaction temperatures are between 0° C. and 100° C.

Compounds according to the present invention VII, VIII, IX, X and XI are accessible via the synthetic routes depicted in scheme 2; $R^{II}$, $R^{III}$, $R^{IV}$, $R^{V}$, $R^{E.1}$, $R^{E.2}$, $R^{E.3}$ have the meanings as defined hereinbefore and hereinafter.

SCHEME 2

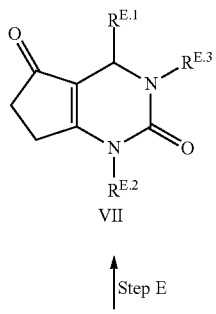

Step E

-continued

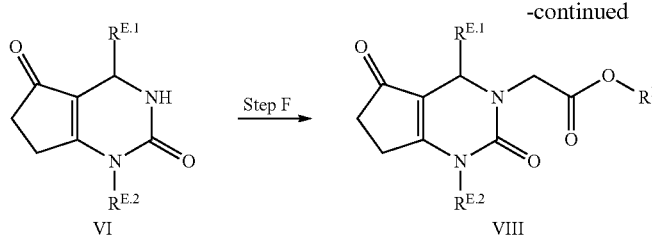

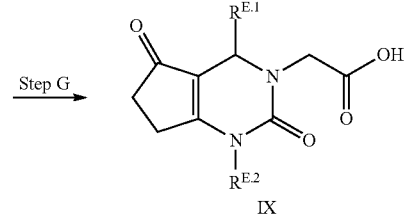

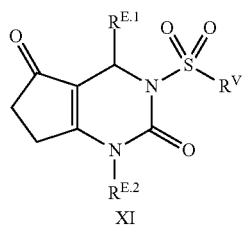

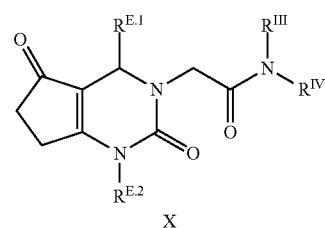

Compounds of the invention VII (Step E, compounds of the invention VI→compounds of the invention VII, $R^{E.3}$=alkyl or substituted alkyl) can be prepared as described in WO04024700 by reacting compounds of the invention VI with an alkylating agent, for example a dialkyl sulfate, for example dimethyl sulfate, an alkyl halide, for example methyl iodide or an alkyl sulfonylate, for example benzyl tosylate, in the presence of a suitable a) base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example tetrahydrofuran, N,N-dimethylformamide, acetonitrile, 1,4-dioxane, dichloromethane or toluene. The reaction takes place within 1-72 hours. Preferred reaction temperatures are between 0° C. and 100° C.

Compounds of the invention VIII (Step F, compounds of the invention VI→compounds of the invention VIII) can be prepared in analogy to compounds of the invention VII (Step E, compounds of the invention VI→compounds of the invention VII), using an appropriate alkyl haloacetate as alkylating agent, for example methyl bromoacetate.

Compounds of the invention IX (Step G, compounds of the invention VIII→compounds of the invention IX) can be prepared as described in WO04024700, by reacting compounds of the invention VIII with water in the presence of a suitable base, for example sodium hydroxide, potassium hydroxide, caesium hydroxide, lithium hydroxide, sodium carbonate, potassium carbonate, sodium methoxide or sodium ethoxide in a suitable solvent, for example water, methanol, ethanol, propanol, N,N-dimethylformamide, tetrahydrofuran, 1,4-dioxane, acetonitrile or mixtures thereof. The reaction takes place within 1-72 hours. Preferred reaction temperatures are between 0° C. and 100° C.

The amide coupling (Step H, compounds of the invention IX→compounds of the invention X) can be achieved by reacting the carboxylic acid intermediate IX with amines $R^{III}NH_2$ or $R^{III}R^{IV}NH$ in the m presence of an amide coupling reagent, for example N,N,N',N'-tetramethyl-O-(benzotriazol-1-yl)uronium tetrafluoroborate (TBTU) or N,N,N',N'-tetramethyl-O-(benzotriazol-1-yl)uronium hexafluorophosphate (HBTU), in the presence of a base, for example triethylamine, N,N-diisopropylethylamine or N-methylmorpholine in an organic solvent, for example N-methyl-2-pyrrolidone N,N-dimethylformamide, N,N-dimethylacetamide or mixtures thereof. The reaction takes place within 1-72 hours. Preferred reaction temperatures are between 0° C. and 50° C., most preferred room temperature.

Compounds of the invention XI (Step J, compounds of the invention VI→compounds of the invention XI, $R^V$=alkyl or aryl) can be prepared as described in WO07137874, by reacting compounds of the invention VI with a sulfonylating agent, for example methanesulfonyl chloride or para-toluenesulfonyl chloride in the presence of a base, for example sodium hydride, lithium diisopropylamide, potassium hexamethyldisilazide, lithium hexamethyldisilazide, an organolithium reagent, for example tert-butyllithium or a Grignard reagent, for example iso-propylmagnesiumchloride, in an organic solvent, for example tetrahydrofuran, N,N-dimethylformamide, acetonitrile, 1,4-dioxane or dichloromethane. The reaction takes place within 1-72 hours. Preferred reaction temperatures are between 0° C. and room temperature.

Compounds according to the present invention XIII and XIV are accessible via the synthetic routes depicted in scheme 3; $R^{III}$, $R^{IV}$, $R^{VI}$, $R^{E.1}$, $R^{E.2}$ have the meanings as defined hereinbefore and hereinafter.

SCHEME 3

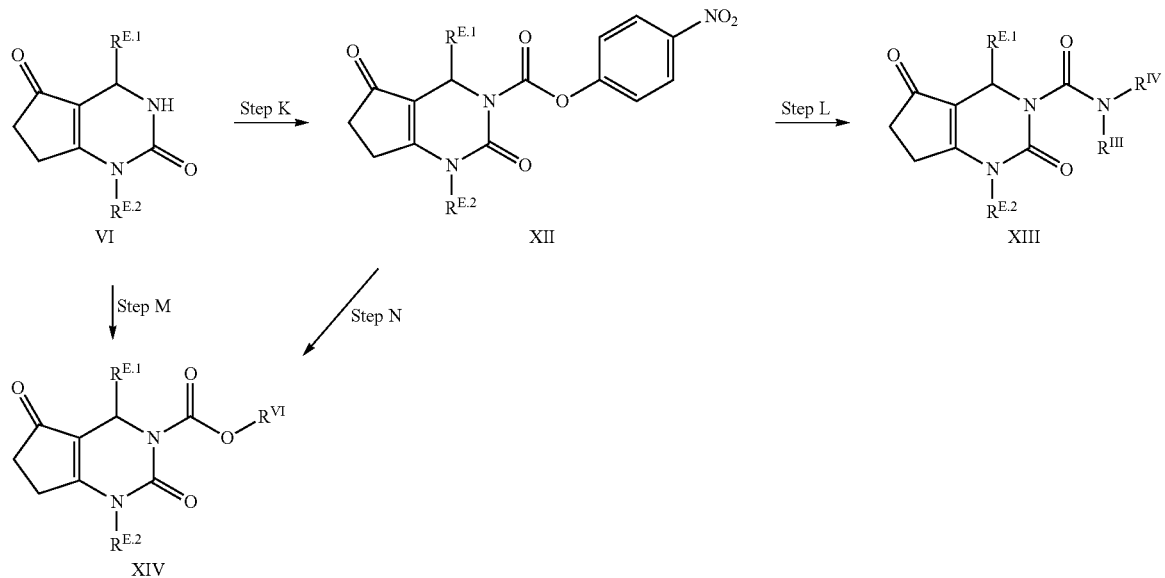

Intermediates XII (Step K, compounds of the invention VI→intermediates XII) can be prepared as described in WO09080199, by reacting compounds of the invention VI with 4-nitrophenyl chloroformate in the presence of a base, for example triethylamine, N,N-diisopropylethylamine or N-methylmorpholine, optionally in the presence of a catalyst, for example 4-dimethylaminopyridine, in an organic solvent, for example dichloromethane, tetrahydrofuran, acetonitrile or N,N-dimethylformamide. The reaction takes place within 1-24 hours. Preferred reaction temperatures are between 0° C. and 50° C., most preferred room temperature.

Compounds of the invention XIII (Step L, intermediates XII→compounds of the invention XIII) can be prepared as described in WO09080199, by reacting intermediates XII with an amine $R^{III}NH_2$ or $R^{III}R^{IV}NH$ in an organic solvent, for example dichloromethane, acetonitrile, tetrahydrofuran, 1,4-dioxane, toluene or N,N-dimethylformamide. The reaction takes place within 1-72 hours. Preferred reaction temperatures are between 0° C. and 50° C., most preferred room temperature.

Compounds of the invention XIV (Step M, compounds of the invention VI compounds of the invention XIV) can be prepared as described in WO07046513 or JP2000273087, by reacting compounds of the invention VI with a suitable chloroformate $ClCO_2R^{VI}$, for example methyl chloroformate or benzyl chloroformate, in the presence of a suitable base, for example potassium carbonate, sodium hydride, sodium hydroxide, cesium carbonate, lithium diisopropylamide, potassium hexamethyldisilazide, lithium hexamethyldisilazide, an organolithium reagent, for example tert-butyl-lithium or a Grignard reagent, for example isopropylmagnesiumchloride, in an organic solvent, for example tetrahydrofuran, N,N-dimethylformamide, acetonitrile, 1,4-dioxane, dichloromethane or toluene. The reaction takes place within 1-72 hours. Preferred reaction temperatures are between 0° C. and 100° C.

Alternatively, compounds of the invention XIV (Step N, intermediates XII→compounds of the invention XIV) can be prepared as described in WO03101917 or WO11085211, by reacting intermediates XII with a suitable alcohol, for example methanol, isopropanol, 2-methoxyethanol or benzyl alcohol, in the presence of a suitable base, for example potassium carbonate, potassium tert-butoxide or sodium hexamethyldisilazide in an organic solvent, for example tetrahydrofuran, N,N-dimethylformamide, acetonitrile, dichloromethane or dimethylsulfoxide. The reaction takes place within 1-72 hours. Preferred reaction temperatures are between 0° C. and 100° C., most preferred room temperature. Additionally to the synthetic route depicted in Scheme 1, compounds of the invention VI are also accessible using the synthetic route depicted in Scheme 4, $R^{E.1}$, $R^{E.2}$ have the meanings as defined hereinbefore and hereinafter.

SCHEME 4

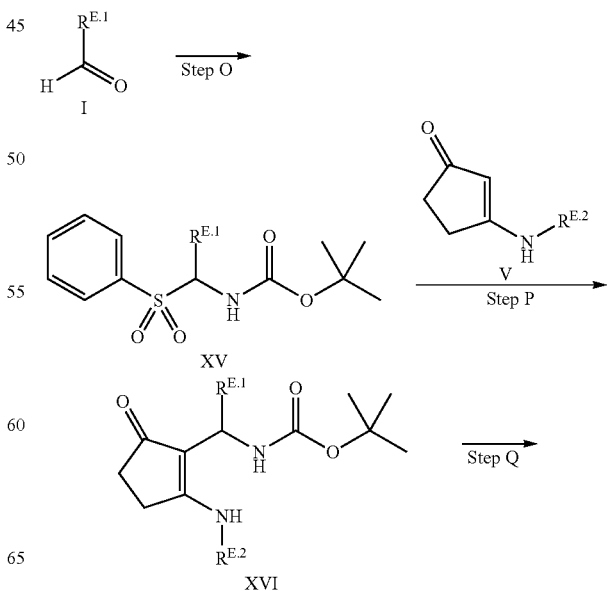

-continued

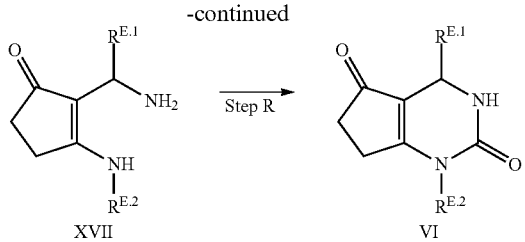

Intermediates XV (Step O, intermediate I→intermediate XV) can be prepared as described in Best et al. (*J. Am. Chem. Soc.* 2012, 134, 18193-18196) or in Yang et al. (*Org. Synth.* 2009, 86, 11-17), by reacting an aromatic aldehyde I with a suitable sulfinate, for example sodium benzenesulfinic acid, and a suitable carbamate, for example methyl carbamate or tert-butyl carbamate, in the presence of a suitable acid, for example formic acid, in a suitable solvent, for example tetrahydrofuran, ethanol, methanol or a mixture of solvents, for example tetrahydrofuran and water. Alternatively, as described in Reingruber et al. (*Adv. Synth. Catal.* 2009, 351, 1019-1024) or in WO06136305, a suitable lewis acid, for example trimethylsilyl chloride, can be used as acid and acetonitrile or toluene can be used as solvent. The reaction takes place within 1-6 days. Preferred reaction temperatures are between 0° C. and 50° C., most preferred room temperature.

Intermediates XVI (Step P, intermediate XV→intermediate XVI) can be prepared in analogy to the method described for the preparation of compounds of the invention VI (Scheme 1, Step D, intermediate III→compound of the invention VI), by reacting intermediates XV with intermediates V in the presence of a suitable base, for example sodium hydride or sodium tert-butoxide, in a suitable organic solvent, for example tetrahydrofuran or 2-methyltetrahydrofuran. The reaction takes place within 1-24 h. Preferred reaction temperatures are between 0° C. and 50° C., most preferred room temperature.

Intermediates XVII (Step Q, intermediate XVI→intermediate XVII) can be prepared by reacting intermediates XVI with a suitable acid, for example hydrogen chloride, in a suitable solvent, for example 1,4-dioxane. The reaction takes place between 1-72 hours. Preferred reaction temperatures are between 0° C. and room temperature, most preferred room temperature.

Compounds of the invention VI (Step R, intermediate XVII→compound of the invention VI) can be prepared as described in Cstitortoki et al. (*Tetrahedron Lett.* 2011, 67, 8564-8571) or in WO11042145, by reacting intermediates XVII with a suitable reagent, for example phosgene, triphosgene or carbonyl diimidazole, in the presence of a suitable base, for example triethylamine, N,N-diisopropylethylamine, pyridine or sodium carbonate, in a suitable solvent, for example acetonitrile, dichloromethane or toluene. The reaction takes place between 1-72 hours. Preferred reaction temperatures are between 0° C. and 50° C., most preferred room temperature.

Preliminary Remarks

The term room temperature denotes a temperature of about 20° C. As a rule, $^1$H NMR spectra and/or mass spectra have been obtained of the compounds prepared. Compounds given with a specific configuration at a stereocenter are isolated as pure isomers.

The retention times given are measured under the following conditions (TFA: trifluoroacetic acid, DEA: diethylamine, scCO$_2$: supercritical carbon dioxide):

| Method Name: | V011_S01 | | | |
|---|---|---|---|---|
| Column: | XBridge C18, 4.6 × 30 mm, 3.5 μm | | | |
| Column Supplier: | Waters | | | |

| Gradient/Solvent Time [min] | % Solvent [H$_2$O, 0.1% NH$_3$] | % Solvent [acetonitrile] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| Method Name: | V012_S01 | | | |
|---|---|---|---|---|
| Column: | XBridge C18, 4.6 × 30 mm, 3.5 μm | | | |
| Column Supplier: | Waters | | | |

| Gradient/Solvent Time [min] | % Solvent [H$_2$O, 0.1% TFA] | % Solvent [acetonitrile] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| Method Name: | W018_S01 | | | |
|---|---|---|---|---|
| Column: | Sunfire C18, 4.6 × 30 mm, 2.5 μm | | | |
| Column Supplier: | Waters | | | |

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 97 | 3 | 4 | 60 |
| 0.15 | 97 | 3 | 3 | 60 |
| 2.15 | 0 | 100 | 3 | 60 |
| 2.20 | 0 | 100 | 4, 5 | 60 |
| 2.40 | 0 | 100 | 4, 5 | 60 |

| Method Name: | X012_S01 | | | |
|---|---|---|---|---|
| Column: | Xbridge BEH C18, 2.1 × 30 mm, 1.7 μm | | | |
| Column Supplier: | Waters | | | |

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

| Method Name: | Z003_004 | | | |
|---|---|---|---|---|
| Column: | XBridge C18, 3 × 30 mm, 2.5 μm | | | |
| Column Supplier: | Waters | | | |

| Gradient/Solvent Time [min] | % Solvent [H$_2$O, 0.1% NH$_3$] | % Solvent [methanol] | Flow [ml/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method Name: | Z011_S03 |
| --- | --- |
| Column: | XBridge C18, 3 × 30 mm, 2.5 μm |
| Column Supplier: | Waters |

| Gradient/Solvent Time [min] | % Solvent [H₂O, 0.1% NH₃] | % Solvent [acetonitrile] | Flow [ml/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z017_S04 |
| --- | --- |
| Column: | ZORBAX™ SB-C₁₈, 3 × 30 mm, 1.8 μm |
| Column Supplier: | Agilent |

| Gradient/Solvent Time [min] | % Solvent [H₂O, 0.1% TFA] | % Solvent [acetonitrile] | Flow [ml/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z018_S04 |
| --- | --- |
| Column: | Sunfire, 3 × 30 mm, 2.5 μm |
| Column Supplier: | Waters |

| Gradient/Solvent Time [min] | % Solvent [H₂O, 0.1% TFA] | % Solvent [acetonitrile] | Flow [ml/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z018_S04 |
| --- | --- |
| Column: | Sunfire, 3 × 30 mm, 2.5 μm |
| Column Supplier: | Waters |

| Gradient/Solvent Time [min] | % Solvent [H₂O, 0.1% TFA] | % Solvent [acetonitrile] | Flow [ml/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | 001_CA03 |
| --- | --- |
| Column: | SunFire C18, 4.6 × 30 mm, 3.5 μm |
| Column Supplier: | Waters |

| Gradient/Solvent Time [min] | % Solvent [H₂O, 0.1% TFA] | % Solvent [acetonitrile] | Flow [ml/min] | Temperature [° C.] |
| --- | --- | --- | --- | --- |
| 0.0 | 98 | 2 | 2.5 | 60.0 |
| 1.5 | 0 | 100 | 2.5 | 60.0 |
| 1.8 | 0 | 100 | 2.5 | 60.0 |

| Method Name: | I_IB_15_MeOH_DEA |
| --- | --- |
| Column: | Chiralpak IB 4.6 × 250 mm, 5 μm |
| Column Supplier: | Daicel |

| Gradient/Solvent Time [min] | % Solvent [MeOH, 0.2% DEA] | % Solvent [scCO₂] | Flow [ml/min] | Temperature [° C.] | Back Pressure [bar] |
| --- | --- | --- | --- | --- | --- |
| 10 min | 15 | 85 | 4 | 40 | 150 |

| Method Name: | I_IB_20_MeOH_DEA |
| --- | --- |
| Column: | Chiralpak IB 4.6 × 250 mm, 5 μm |
| Column Supplier: | Daicel |

| Gradient/Solvent Time [min] | % Solvent [MeOH, 0.2% DEA] | % Solvent [scCO₂] | Flow [ml/min] | Temperature [° C.] | Back Pressure [bar] |
| --- | --- | --- | --- | --- | --- |
| 10 min | 20 | 80 | 4 | 40 | 150 |

| Method Name: | I_IC_30_MeOH_DEA |
| --- | --- |
| Column: | Chiralpak IC 4.6 × 250 mm, 5 μm |
| Column Supplier: | Daicel |

| Gradient/Solvent Time [min] | % Solvent [MeOH, 0.2% DEA] | % Solvent [scCO₂] | Flow [ml/min] | Temperature [° C.] | Back Pressure [bar] |
| --- | --- | --- | --- | --- | --- |
| 10 min | 30 | 70 | 4 | 40 | 100 |

| Method Name: | X011_S03 |
| --- | --- |
| Column: | Xbridge BEH C18, 2.1 × 30 mm, 1.7 μm |
| Column Supplier: | Waters |

| Gradient/Solvent Time [min] | % Solvent [H₂O, 0.1% NH₃] | % Solvent [acetonitrile] | Flow [ml/min] | Temperature [° C.] |
| --- | --- | --- | --- | --- |
| 0.0 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

| Method Name: | X018_S01 |
| --- | --- |
| Column: | Sunfire C18, 2.1 × 30 mm, 2.5 μm |
| Column Supplier: | Waters |

| Gradient/Solvent Time [min] | % Solvent [H₂O, 0.1% TFA] | % Solvent [acetonitrile] | Flow [ml/min] | Temperature [° C.] |
| --- | --- | --- | --- | --- |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| Method Name: | Z006_U01 |
| --- | --- |
| Column: | XBridge Phenyl, 3 × 30 mm, 2.5 μm |
| Column Supplier: | Waters |

| Gradient/ Solvent Time [min] | % Solvent [H$_2$O, 0.1% TFA] | % Solvent [methanol] | Flow [ml/min] | Temperature [° C.] |
| --- | --- | --- | --- | --- |
| 0.0 | 50 | 50 | 1.9 | 60 |
| 0.20 | 50 | 50 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method Name: | 001_CA07 |
| --- | --- |
| Column: | SunFire C18, 2.1 × 50 mm, 2.5 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.0 | 95 | 5 | 1.5 | 60.0 |
| 0.75 | 0 | 100 | 1.5 | 60.0 |
| 0.85 | 0 | 100 | 1.5 | 60.0 |

| Method Name: | 002_CA03 |
| --- | --- |
| Column: | SunFire C18, 3.0 × 30 mm, 2.5 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.0 | 99 | 1 | 2.0 | 60.0 |
| 0.90 | 0 | 100 | 2.0 | 60.0 |
| 1.1 | 0 | 100 | 2.0 | 60.0 |

| Method Name: | 002_CA07 |
| --- | --- |
| Column: | XBridge BEH C18, 3 × 30 mm, 1.7 μm |
| Column Supplier: | Waters |

| Gradient/ Solvent Time [min] | % Solvent [H$_2$O, 0.1% NH$_3$] | % Solvent [acetonitrile] | Flow [ml/min] | Temperature [° C.] |
| --- | --- | --- | --- | --- |
| 0.0 | 95 | 5.0 | 1.5 | 60.0 |
| 0.7 | 0.1 | 99.9 | 1.5 | 60.0 |
| 0.8 | 0.1 | 99.9 | 1.5 | 60.0 |
| 0.81 | 95 | 5 | 1.5 | |
| 1.1 | 95 | 5 | 1.5 | |

| Method Name: | 003_CA04 |
| --- | --- |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.0 | 98 | 2 | 2.0 | 60.0 |
| 1.2 | 0 | 100 | 2.0 | 60.0 |
| 1.4 | 0 | 100 | 2.0 | 60.0 |

| Method Name: | 005_CA01 |
| --- | --- |
| Column: | SunFire C18, 3.0 × 30 mm, 2.5 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.0 | 98 | 2 | 2.0 | 60.0 |
| 1.2 | 0 | 100 | 2.0 | 60.0 |
| 1.4 | 0 | 100 | 2.0 | 60.0 |

| Method Name: | I_IA_15_MeOH_DEA |
| --- | --- |
| Column: | Chiralpak IA 4.6 × 250 mm, 5 μm |
| Column Supplier: | Daicel |

| Gradient/ Solvent Time [min] | % Solvent [MeOH, 0.2% DEA] | % Solvent [scCO$_2$] | Flow [ml/min] | Temperature [° C.] | Back Pressure [bar] |
| --- | --- | --- | --- | --- | --- |
| 10 min | 15 | 85 | 4 | 40 | 150 |

| Method Name: | I_IA_20_MeOH_NH3 |
| --- | --- |
| Column: | Chiralpak IA 4.6 × 250 mm, 5 μm |
| Column Supplier: | Daicel |

| Gradient/ Solvent Time [min] | % Solvent [MeOH, 20 mM NH$_3$] | % Solvent [scCO$_2$] | Flow [ml/min] | Temperature [° C.] | Back Pressure [bar] |
| --- | --- | --- | --- | --- | --- |
| 10 min | 20 | 80 | 4 | 40 | 150 |

| Method Name: | I_IA_30_MeOH_NH3 |
| --- | --- |
| Column: | Chiralpak IA 4.6 × 250 mm, 5 μm |
| Column Supplier: | Daicel |

| Gradient/ Solvent Time [min] | % Solvent [MeOH, 20 mM NH$_3$] | % Solvent [scCO$_2$] | Flow [ml/min] | Temperature [° C.] | Back Pressure [bar] |
| --- | --- | --- | --- | --- | --- |
| 10 min | 30 | 70 | 4 | 40 | 150 |

| Method Name: | I_IB_25_MeOH_DEA |
| --- | --- |
| Column: | Chiralpak IB 4.6 × 250 mm, 5 μm |
| Column Supplier: | Daicel |

| Gradient/ Solvent Time [min] | % Solvent [MeOH, 0.2% DEA] | % Solvent [scCO$_2$] | Flow [ml/min] | Temperature [° C.] | Back Pressure [bar] |
| --- | --- | --- | --- | --- | --- |
| 10 min | 25 | 75 | 4 | 40 | 150 |

| Method Name: | I_IB_25_MeOH_NH3 |
| --- | --- |
| Column: | Chiralpak IB 4.6 × 250 mm, 5 μm |
| Column Supplier: | Daicel |

| Gradient/ Solvent Time [min] | % Solvent [MeOH, 20 mM NH$_3$] | % Solvent [scCO$_2$] | Flow [ml/min] | Temperature [° C.] | Back Pressure [bar] |
| --- | --- | --- | --- | --- | --- |
| 10 min | 25 | 75 | 4 | 40 | 150 |

| Method Name: | L_IB_30_MeOH_DEA |
| --- | --- |
| Column: | Chiralpak IB 4.6 × 250 mm, 5 μm |
| Column Supplier: | Daicel |

| Gradient/ Solvent Time [min] | % Solvent [MeOH, 0.2% DEA] | % Solvent [scCO$_2$] | Flow [ml/min] | Temperature [° C.] | Back Pressure [bar] |
| --- | --- | --- | --- | --- | --- |
| 10 min | 30 | 70 | 4 | 40 | 150 |

| Method Name: | L_IB_40_MeOH_DEA |
| --- | --- |
| Column: | Chiralpak IB 4.6 × 250 mm, 5 μm |
| Column Supplier: | Daicel |

| Gradient/ Solvent Time [min] | % Solvent [MeOH, 0.2% DEA] | % Solvent [scCO$_2$] | Flow [ml/min] | Temperature [° C.] | Back Pressure [bar] |
| --- | --- | --- | --- | --- | --- |
| 10 min | 40 | 60 | 4 | 40 | 150 |

Assignment of Absolute Configurations

The absolute configuration of example 1A has been assigned unambiguously by X-ray structure analysis to be (R). This (R)-enantiomer (example 1A) is significantly more potent with respect to the inhibition of neutrophil elastase than the (S)-enantiomer (example 1B), as can be seen from the measured IC$_{50}$ values of 11.5 nM (example 1A) and 8040 nM (example 1B), respectively. The absolute configuration of all other pure enantiomers described has been assigned in analogy to example 1A, that is, the more potent enantiomer (the eutomer) with respect to the inhibition of neutrophil elastase, i.e. the enantiomer with the lower IC$_{50}$ value has been assigned to have the same absolute configuration as example 1A.

Syntheses of Starting Materials

The following starting materials are prepared as described in the literature cited:
3-(3-(trifluoromethyl)phenylamino)cyclopent-2-enone: *Aust. J. Chem.* 2005, 58, 870-876; 1-bromo-4-(chloro(isocyanato)methyl)benzene: *Synlett* 2006, 3, 375-378; tert-butyl (4-cyanophenyl)(phenylsulfonyl)methylcarbamate: *J. Am. Chem. Soc.* 2011, 133, 1248-1250.

The synthesis of the following starting materials has been described before in the literature cited:
tert-butyl(4-bromophenyl)(phenylsulfonyl)methylcarbamate: *J. Am. Chem. Soc.* 2011, 133, 8892-8895; 3-(benzyloxy)cyclopent-2-enone: *Chin. Chem. Lett.* 2008, 19, 767-770.

INTERMEDIATE 1

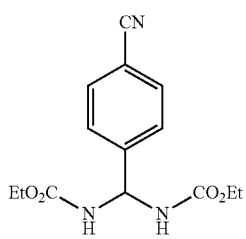

Diethyl (4-Cyanophenyl)methylenedicarbamate

In a three-necked round bottom flask equipped with a drying tube filled with calcium chloride and an inlet for nitrogen, 4-formylbenzonitrile (25.0 g, 191 mmol) and ethyl carbamate (37.4 g, 419 mmol) are heated at 145° C. The flask is being purged with a flow of nitrogen, and concentrated sulfuric acid (ca. 200 μL, ca. 3 mmol) is added slowly drop by drop. After 7 h the solidified reaction mixture is cooled to room temperature, crushed, mixed thoroughly with water and dried. Yield: 53.0 g; ESI mass spectrum: [M+Na]$^+$=314; Retention time HPLC: 0.88 min (V011_S01).

INTERMEDIATE 2

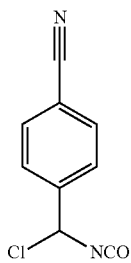

4-(Chloro(isocyanato)methyl)benzonitrile

Phosphorous pentachloride (83.3 g, 400 mmol) is added to a suspension of diethyl (4-cyanophenyl)methylenedicarbamate (intermediate 1, 53.0 g, 182 mmol) in benzene (200 mL) and the mixture is heated at reflux for 2 h. The benzene is evaporated and the mixture is then purified by distillation under reduced pressure. The first fraction (ca. 40° C., ca. 0.01 mbar) is discarded. The second fraction (ca. 110° C., ca. 0.6 mbar) is collected. Yield: 28.4 g; ESI mass spectrum: [M+MeOH−HCl+H]$^+$=189; Retention time HPLC: 0.65 min (Z003_004).

INTERMEDIATE 3

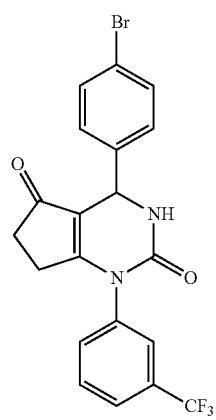

4-(4-Bromophenyl)-1-(3-(trifluoromethyl)phenyl)-3,4,6,7-tetrahydro-1H-cyclopenta[d]pyrimidine-2,5-dione A solution of 1-bromo-4-(chloro(isocyanato)methyl)benzene (14.7 g, 47.6 mmol) in dichloromethane (100 mL) is added to a solution of 3-(3-(trifluoromethyl)phenylamino)-cyclopent-2-enone (11.0 g, 45.6 mmol) in dichloromethane (100 mL) and the mixture is heated at reflux for 1.5 hours. Water is added, and the phases are extracted twice with dichloromethane. The combined organic layers are concentrated and the residue is purified by flash chromatography on silica (gradient cyclohexane/ethyl acetate 4:1 to ethyl acetate). Yield: 7.5 g; ESI mass spectrum: ESI mass spectrum: [($^{79}$Br)-M+H]$^+$=451, [($^{81}$Br)-M+H]$^+$=453; Retention time HPLC: 1.15 min (V012_S01).

Intermediates 3A and 3B: Enantiomers of Intermediate 3

The enantiomers of racemic 4-(4-bromophenyl)-1-(3-(trifluoromethyl)phenyl)-3,4,6,7-tetrahydro-1H-cyclopenta[d]pyrimidine-2,5-dione (intermediate 3, 2.10 g, 4.66 mmol) are separated by preparative supercritical fluid chromatography on a chiral phase (Daicel Chiralpak IB, 10×250 mm, 5 µm, 20% MeOH+0.2% diethylamine in supercritical CO$_2$, 40° C., 150 bar back pressure).

INTERMEDIATE 3A

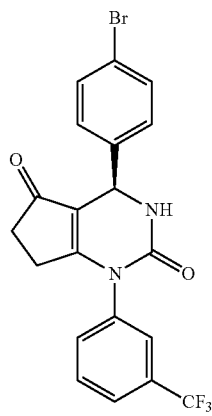

(R)-4-(4-Bromophenyl)-1-(3-(trifluoromethyl)phenyl)-3,4,6,7-tetrahydro-1H-cyclopenta[d]pyrimidine-2,5-dione Yield: 1.05 g; ESI mass spectrum: [($^{79}$Br)-M+H]$^+$=451, [($^{81}$Br)-M+H]$^+$=453; Retention time: 3.76 min (late eluting enantiomer) (I_IB_20_MeOH_DEA).

INTERMEDIATE 3B

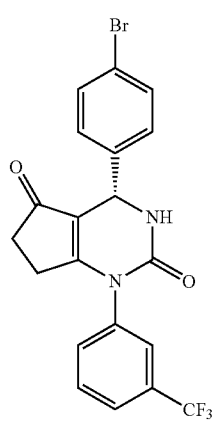

(S)-4-(4-Bromophenyl)-1-(3-(trifluoromethyl)phenyl)-3,4,6,7-tetrahydro-1H-cyclopenta[d]pyrimidine-2,5-dione Yield: 0.94 g; ESI mass spectrum: [($^{79}$Br)-M+H]$^+$=451, [($^{81}$Br)-M+H]$^+$=453; Retention time: 3.08 min (early eluting enantiomer) (I_IB_20_MeOH_DEA).

INTERMEDIATE 4

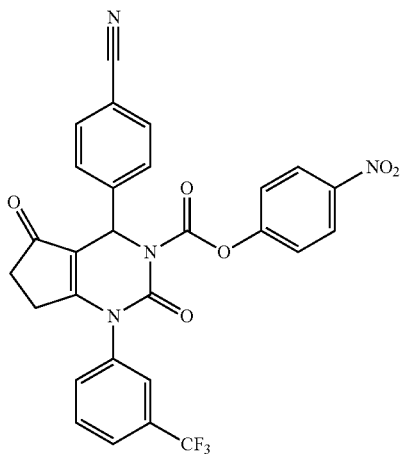

4-Nitrophenyl 4-(4-Cyanophenyl)-2,5-dioxo-1-(3-(trifluoromethyl)phenyl)-4,5,6,7-tetrahydro-1H-cyclopenta[d]pyrimidine-3(2H)-carboxylate 4-Nitrophenyl chloroformate (1.11 g, 5.52 mmol) is added to a solution of 4-(2,5-dioxo-1-(3-(trifluoromethyl)phenyl)-2,3,4,5,6,7-hexahydro-1H-cyclopenta[d]pyrimidin-4-yl)benzo-nitrile (example 1, 1.33 g, 3.35 mmol), N,N-diisopropylethylamine (2.28 mL, 13.4 mmol) and 4-(dimethylamino)pyridine (409 mg, 3.35 mmol) in dichloromethane (24 mL). After 1 h the mixture is washed with water and concentrated. The residue is purified by flash chromatography on silica (gradient cyclohexane to cyclohexane/ethyl acetate 3:7). Yield: 623 mg; ESI mass spectrum [M+H]$^+$=563; Retention time HPLC: 0.99 min (Z018_S04).

INTERMEDIATE 5

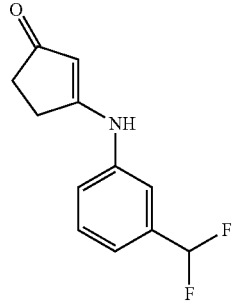

3-(3-(Difluoromethyl)phenylamino)cyclopent-2-enone

A mixture of cyclopentane-1,3-dione (2.00 g, 20.4 mmol), 3-(difluoromethyl)aniline (2.92 g, 20.4 mmol) and Ytterbium (III) trifluormethanesulfonate (63 mg, 0.10 mmol, 0.5 mol %) is stirred at room temperature for 2 h. Methanol and water are added and the resulting precipitate is filtered and dried. Yield: 2.75 g; ESI mass spectrum: [M+H]$^+$=224; Retention time HPLC: 0.82 min (V012_S01).

INTERMEDIATE 6

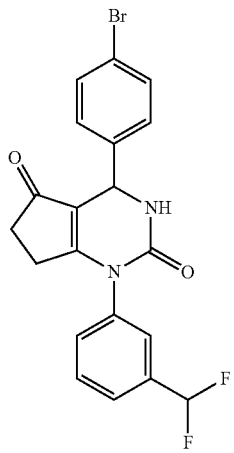

4-(4-Bromophenyl)-1-(3-(difluoromethyl)phenyl)-3,4,6,7-tetrahydro-1H-cyclopenta[d]-pyrimidine-2,5-dione A solution of 1-bromo-4-(chloro(isocyanato)methyl)benzene (240 mg, 0.974 mmol) in dichloromethane (2 mL) is added dropwise to a solution of 3-(3-(difluoromethyl)phenylamino)cyclopent-2-enone (intermediate 5, 217 mg, 0.974 mmol) in dichloromethane (2 mL) and the reaction mixture is heated at reflux for 2 h. Water is added, and the phases are extracted twice with dichloromethane. The combined organic layers are concentrated and the residue is purified by flash chromatography on silica (gradient cyclohexane/ethyl acetate 4:1 to ethyl acetate). Yield: 159 mg; ESI mass spectrum: [($^{79}$Br)-M+H]$^+$=433, [($^{81}$Br)-M+H]$^+$=435; Retention time HPLC: 0.56 min (X012_S01).

INTERMEDIATE 7

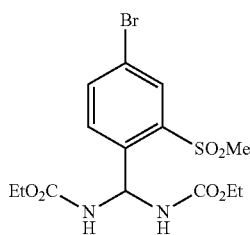

Diethyl (4-Bromo-2-methylsulfonyl)phenyl)methylenedicarbamate

The title compound is prepared in analogy to diethyl (4-cyanophenyl)methylenedicarbamate (intermediate 1), substituting 4-formylbenzonitrile with 4-bromo-2-(methyl-sulfonyl)benzaldehyde (4.50 g, 17.1 mmol) and purifying the crude product by flash chromatography on silica (gradient dichloromethane to dichloromethane/methanol 93:7). Yield: 5.05 g; ESI mass spectrum: [($^{79}$Br)-M+H]$^+$=423, [($^{81}$Br)-M+H]$^+$=425; Retention time HPLC: 0.77 min (Z011_S03).

INTERMEDIATE 8

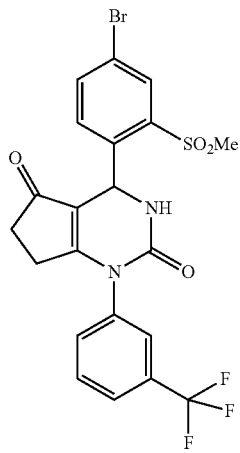

4-(4-Bromo-2-(methylsulfonyl)phenyl)-1-(3-(trifluoromethyl)phenyl)-3,4,6,7-tetrahydro-1H-cyclopenta[d]pyrimidine-2,5-dione Step 1: 4-Bromo-1-(chloro(isocyanato)methyl)-2-(methylsulfonyl)benzene Phosphorous pentachloride (5.47 g, 26.2 mmol) is added to a suspension of diethyl (4-bromo-2-methylsulfonyl)phenyl) methylenedicarbamate (intermediate 7, 5.05 g, 11.9 mmol) in toluene (30 mL) and the mixture is heated at reflux for 3 h. The toluene is evaporated and the mixture is then purified by distillation under reduced pressure (ca. 160° C., 0.1 mbar). Yield: 945 mg.

Step 2: 4-(4-Bromo-2-(methylsulfonyl)phenyl)-1-(3-(trifluoromethyl)phenyl)-3,4,6,7-tetrahydro-1H-cyclopenta[d]pyrimidine-2,5-dione 3-(3-(Trifluoromethyl)phenylamino)cyclopent-2-enone (234 mg, 0.97 mmol) is added to a solution of 4-bromo-1-(chloro(isocyanato)methyl)-2-(methylsulfonyl)benzene (Step 1, 945 mg, 2.91 mmol) in dichloromethane (10 mL). The mixture is heated at reflux over night and then concentrated under reduced pressure. The residue is purified by reversed phase HPLC (Agilent ZORBAX™ SB—C$_{18}$, gradient of acetonitrile in water, 0.1% formic acid). Yield: 110 mg; ESI mass spectrum: ESI mass spectrum: [($^{79}$Br)-M+H]$^+$=529, [($^{81}$Br)-M+H]$^+$=531; Retention time HPLC: 1.21 min (Z017_S04).

INTERMEDIATE 9

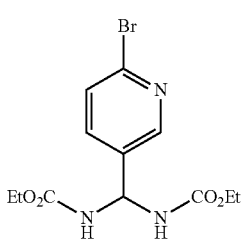

Diethyl (6-Bromopyridin-3-yl)methylenedicarbamate

The title compound is prepared in analogy to diethyl (4-cyanophenyl)methylenedicarbamate (intermediate 1), substituting 4-formylbenzonitrile with 6-bromonicotinaldehyde (7.00 g, 37.6 mmol) and reducing the reaction time from 7 h to 1 h. Yield: 7.82 g; ESI mass spectrum: [($^{79}$Br)-M+H]$^+$=346, [($^{81}$Br)-M+H]$^+$=348; Retention time HPLC: 0.87 min (V011_S01).

INTERMEDIATE 10

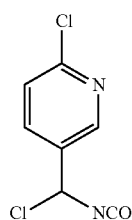

2-Chloro-5-(chloro(isocyanato)methyl)pyridine

The title compound is prepared in analogy to 4-(chloro(isocyanato)methyl)benzonitrile (intermediate 2), replacing diethyl (4-cyanophenyl)methylenedicarbamate (intermediate 1) with diethyl (6-bromopyridin-3-yl)methylenedicarbamate (intermediate 9, 7.82 g, 22.6 mmol) and collecting the appropriate fraction (ca. 85-90° C., ca. 0.3 mbar). Yield: 1.07 g. ESI mass spectrum: [M−HCl+2MeOH+H]$^+$=231; Retention time HPLC: 0.73 min (V011_S01).

INTERMEDIATE 11

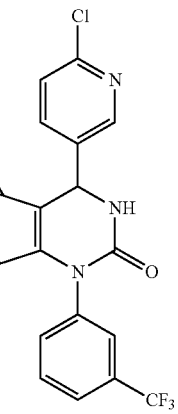

4-(6-Chloropyridin-3-yl)-1-(3-(trifluoromethyl)phenyl)-3,4,6,7-tetrahydro-1H-cyclopenta[d]pyrimidine-2,5-dione A solution of 3-(3-(trifluoromethyl)phenylamino)cyclopent-2-enone (900 mg, 3.73 mmol) in dichloromethane (8 mL) is added dropweise to a solution of 2-chloro-5-(chloro(iso-cyanato)methyl)pyridine (intermediate 10, 757 mg, 3.73 mmol) in dichloromethane (7 mL). The mixture is stirred at room temperature for 2 h and concentrated, and the residue is purified by reversed phase HPLC (Waters Xbridge™-C$_{18}$, gradient of acetonitrile in water, 0.1% NH$_3$). Yield: 160 mg; ESI mass spectrum [M+H]$^+$=408; Retention time HPLC: 0.98 min (V011_S01).

INTERMEDIATE 12

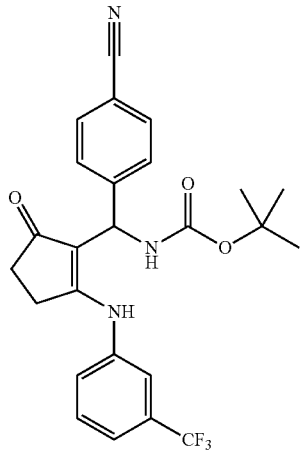

tert-Butyl(4-Cyanophenyl)(5-oxo-2-(3-(trifluoromethyl)phenylamino)cyclopent-1-enyl)methylcarbamate Sodium hydride (60% in mineral oil, 1.06 g, 26.5 mmol) is added at room temperature in portions to a mixture of 3-(3-(trifluoromethyl)phenylamino)cyclopent-2-enone (4.31 g, 17.9 mmol) and 2-methyltetrahydrofuran. After 20 min tert-butyl(4-cyanophenyl)(phenyl-sulfonyl)methylcarbamate (10.0 g, 24.2 mmol based on 90% purity) is added, and the mixture is stirred at room temperature for 1 h. Water is added and the phases are separated. The organic layer is washed with water and concentrated under reduced pressure, and the residue is recrystallized from tert-butyl methyl ether. Yield: 6.92 g. ESI mass spectrum: [M+H]$^+$=472; Retention time HPLC: 0.76 min (X012_S01).

INTERMEDIATE 13

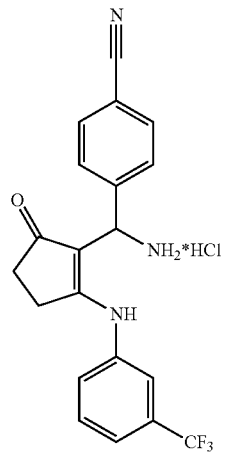

4-(Amino(5-oxo-2-(3-(trifluoromethyl)phenylamino)cyclopent-1-enyl)methyl)benzonitrile hydrochloride A solution of hydrogen chloride in 1,4-dioxane (4 M, 29.3 mL, 117 mmol) is added to a mixture of tert-butyl(4-cyanophenyl)(5-oxo-2-(3-(trifluoromethyl)phenylamino)cyclopent-1-enyl)methylcarbamate (intermediate 12, 6.92 g, 14.7 mmol) in 1,4-dioxane (30 mL), and the mixture is stirred at room temperature for 2 h. All volatiles are removed under reduced pressure, and the residue is treated with tert-butyl methyl ether (50 mL). The precipitate is filtered, washed with tert-butyl methyl ether and dried. Yield: 6.10 g. ESI mass spectrum: [M+H]$^+$=372; Retention time HPLC: 0.62 min (X011_S02).

INTERMEDIATE 14

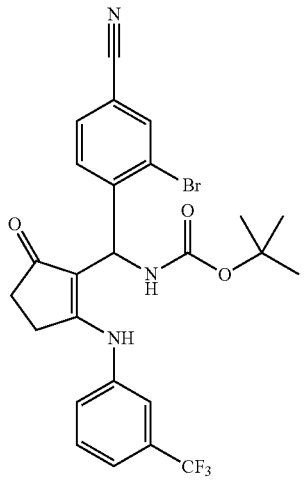

tert-Butyl (2-Bromo-4-cyanophenyl)(5-oxo-2-(3-(trifluoromethyl)phenylamino)cyclopent-1-enyl)methylcarbamate Step 1: tert-Butyl (2-Bromo-4-cyanophenyl)(phenyl-sulfonyl)methylcarbamate Formic acid (3.9 mL, 104 mmol) is added to a solution of tert-butyl carbamate (1.90 g, 16.2 mmol), 2-bromo-4-cyanobenzaldehyde (3.41 g, 16.2 mmol) and sodium benzenesulfinate (2.67 g, 16.2 mmol) in a mixture of tetrahydrofuran (7.0 mL) and water (60 mL), and the mixture is stirred at room temperature for 6 days. Water (180 mL) is added, and the precipitate is filtered and washed with water. The precipitate is treated with tert-butyl methyl ether (30 mL), and the mixture is stirred for 30 min. The precipitate is filtered, washed with tert-butyl methyl ether, and dried. Yield: 3.35 g. ESI mass spectrum: [($^{79}$Br)-M+H]$^+$=451, [($^{81}$Br)-M+H]$^+$=453; Retention time HPLC: 0.66 min (X012_S01).

Step 2: tert-Butyl (2-Bromo-4-cyanophenyl)(5-oxo-2-(3-(trifluoromethyl)phenylamino)cyclopent-1-enyl)methylcarbamate Sodium hydride (60% in mineral oil, 360 mg, 9.00 mmol) is added in portions to a mixture of 3-(3-(trifluoromethyl)phenylamino)cyclopent-2-enone (2.16 g, 8.96 mmol) and 2-methyltetrahydrofuran (30 mL). After 30 min tert-butyl (2-bromo-4-cyanophenyl)(phenyl-sulfonyl)methylcarbamate (Step 1, 3.35 g, 7.43 mmol) is added and the mixture is stirred at room temperature for 2 h. Water is added and the phases are separated. The aqueous phase is extracted twice with ethyl acetate, and the combined organic phases are washed with water, dried over MgSO$_4$ and concentrated under reduced pressure. The residue is treated with tert-butyl methyl ether, and the mixture is stirred for 15 min. The precipitate is filtered, washed with tert-butyl methyl ether, and dried. Yield: 3.18 g. ESI mass spectrum: [($^{79}$Br)-M+H]$^+$=550, [($^{81}$Br)-M+H]$^+$=552; Retention time HPLC: 0.73 min (X012_S01).

Intermediates 14.1-14.6

The following intermediates are prepared in analogy to tert-butyl (2-bromo-4-cyano-phenyl)(5-oxo-2-(3-(trifluoromethyl)phenylamino)cyclopent-1-enyl)methylcarbamate (intermediate 14), substituting 2-bromo-4-cyanobenzaldehyde tert-butyl (2-bromo-4-cyano-phenyl)(phenylsulfonyl)methylcarbamate with the appropriate starting material as indicated in Table 2.

TABLE 2

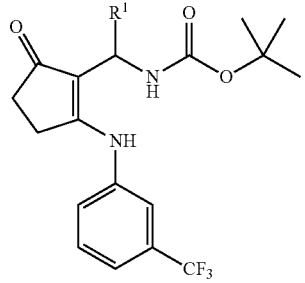

| Intermediate | Starting Material | R$^1$ | MS [M + H]$^+$ | Retention time [min] | HPLC-Method |
|---|---|---|---|---|---|
| 14.1 | ![structure with CN, Cl, CHO] | ![structure with CN, Cl] | 506 | 0.76 | X012_S01 |

TABLE 2-continued

| Intermediate | Starting Material | R¹ | MS [M + H]⁺ | Retention time [min] | HPLC-Method |
|---|---|---|---|---|---|
| 14.2 | | | 564 | 0.77 | X012_S01 |
| 14.3 | | | 502 | 0.76 | X012_S01 |
| 14.4 | | | 486 | 0.75 | X012_S01 |
| 14.5 | | | 571, 573 | 0.80 | X012_S01 |

TABLE 2-continued

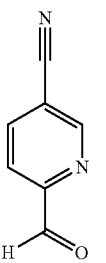

| Intermediate | Starting Material | R¹ | MS [M + H]⁺ | Retention time [min] | HPLC-Method |
|---|---|---|---|---|---|
| 14.6 | 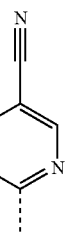 | | 473 | 1.13 | Z018_S04 |

Intermediate 15

INTERMEDIATE 15

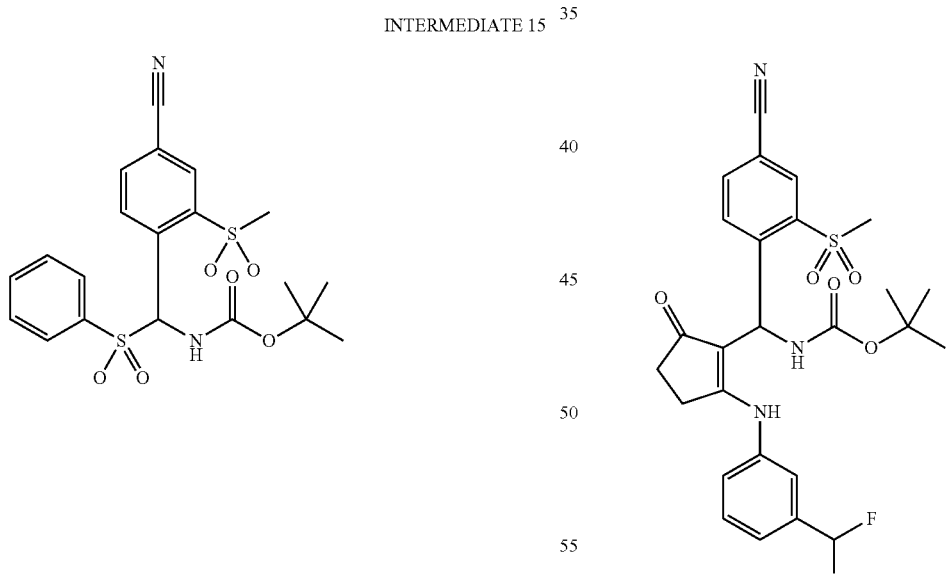

tert-Butyl (4-Cyano-2-(methylsulfonyl)phenyl)(phenylsulfonyl)methylcarbamate

Formic acid (6.2 mL, 164 mmol) is added to a solution of tert-butyl carbamate (3.05 g, 26.0 mmol), 4-formyl-3-(methylsulfonyl)benzonitrile (5.44 g, 26.0 mmol) and sodium benzenesulfinate (4.27 g, 26.0 mmol) in a mixture of tetrahydrofuran (10 mL) and water (25 mL), and the mixture is stirred at room temperature for 4 days. Water (30 mL) is added, and the precipitate is filtered, washed with water and acetonitrile and dried Yield: 5.10 g. ESI mass spectrum: [M+H]⁺=451; Retention time HPLC: 0.59 min (X012_S01).

Intermediate 16

INTERMEDIATE 16 tert-Butyl (4-Cyano-2-(methylsulfonyl)phenyl)(2-(3-(difluoromethyl)phenylamino)-5-oxocyclopent-1-enyl)methylcarbamate Sodium hydride (60% in mineral oil, 106 mg, 2.67 mmol) is added in portions to a mixture of 3-(3-(difluoromethyl)phenylamino)cyclopent-2-enone (intermediate 5, 595 mg, 2.66 mmol) and 2-methyltetrahydrofuran (20 mL). After 2 h tert-butyl (4-cyano-2-(methyl-sulfonyl)phenyl)(phenylsulfonyl)methylcarbamate (intermediate 15, 1.00 g, 2.20 mmol) is added, and the mixture is stirred at room temperature for 2 h. Water is added and the mixture is extracted with 2-methyltetrahydrofuran. The organic layer is dried over $Na_2SO_4$ and concentrated under reduced pressure. The residue is purified by reversed phase HPLC (Waters SunFire™-$C_{18}$, gradient of acetonitrile in water, 0.1% formic acid). Yield: 665 mg; ESI mass spectrum $[M+H]^+$=532; Retention time HPLC: 1.13 min (Z018_S04).

INTERMEDIATE 17

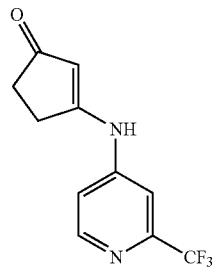

3-(2-(Trifluoromethyl)pyridin-4-ylamino)cyclopent-2-enone

A mixture of cyclopentane-1,3-dione (1.51 g, 15.4 mmol), 2-(trifluoromethyl)pyridin-4-amine (2.50 g, 15.4 mmol) and acetic acid (7.5 mL) is heated at 130° C. for 5 h, cooled at room temperature, diluted with water and methanol, and purified by reversed phase HPLC (Waters SunFire™-$C_{18}$, gradient of acetonitrile in water, 0.1% formic acid). Yield: 2.26 g; ESI mass spectrum $[M+H]^+$=243; Retention time HPLC: 0.77 min (Z018_S04).

INTERMEDIATE 18

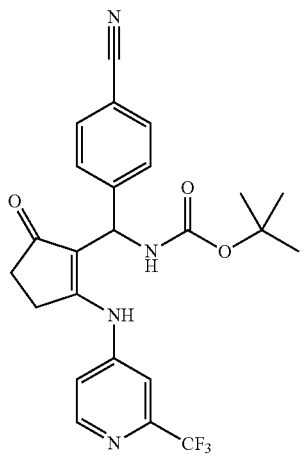

tert-Butyl(4-Cyanophenyl)(5-oxo-2-(2-(trifluoromethyl)pyridin-4-ylamino)cyclopent-1-enyl)methylcarbamate Sodium hydride (60% in mineral oil, 895 mg, 22.4 mmol) is added in portions to a mixture of 3-(2-(trifluoromethyl)pyridin-4-ylamino)cyclopent-2-enone (intermediate 17, 4.52 g, 18.7 mmol) and 2-methyltetrahydrofuran (30 mL). After 30 min tert-butyl (4-cyano-phenyl)(phenylsulfonyl)methylcarbamate (6.90 g, 18.5 mmol) is added, and mixture is stirred at room temperature for 30 min Water is added, and the phases are separated. The organic phase is dried over $Na_2SO_4$ and concentrated under reduced pressure. Yield: 9.20 g; ESI mass spectrum $[M+H]^+$=473; Retention time HPLC: 1.09 min (Z018_504).

INTERMEDIATE 19

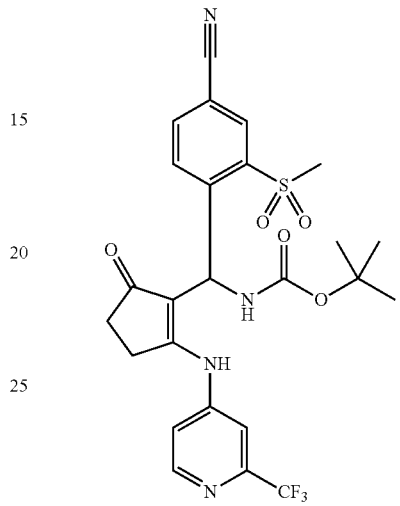

tert-Butyl (4-Cyano-2-(methylsulfonyl)phenyl)(5-oxo-2-(2-(trifluoromethyl)pyridin-4-ylamino)cyclopent-1-enyl)methylcarbamate Sodium hydride (60% in mineral oil, 515 mg, 12.9 mmol) is added in portions to a mixture of 3-(2-(trifluoromethyl)pyridin-4-ylamino)cyclopent-2-enone (intermediate 17, 2.60 g, 10.7 mmol) and 2-methyltetrahydrofuran (40 mL). After 10 min tert-butyl (4-cyano-2-(methylsulfonyl)phenyl)(phenylsulfonyl)methylcarbamate (intermediate 15, 4.83 g, 10.7 mmol) is added, and the mixture is stirred at room temperature for 30 min Water and ethyl acetate are added, and the phases are separated. The organic phases is washed twice with water and concentrated under reduced pressure. Yield: 6.20 g; ESI mass spectrum $[M+H]^+$=551; Retention time HPLC: 1.12 min (Z018_S04).

INTERMEDIATE 20

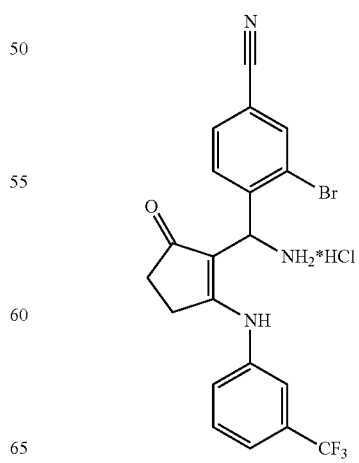

4-(Amino(5-oxo-2-(3-(trifluoromethyl)phenylamino) cyclopent-1-enyl)methyl)-3-bromobenzonitrile hydrochloride A solution of hydrogen chloride in 1,4-dioxane (4 M, 15.2 mL, 61 mmol) is added to a mixture of tert-butyl (2-bromo-4-cyanophenyl)(5-oxo-2-(3-(trifluoromethyl)phenylamino)-cyclopent-1-enyl)methylcarbamate (intermediate 14, 6.71 g, 12.2 mmol) in 1,4-dioxane (30 mL), and the mixture is stirred at room temperature for 2 h and then cooled in an ice bath. The precipitate is filtered, washed with cold acetonitrile and diethyl ether and dried. Yield: 5.90 g. ESI mass spectrum: [($^{79}$Br)-M+H]$^+$=450, [($^{81}$Br)-M+H]$^+$=452; Retention time HPLC: 1.17 min (V011_S01).

Intermediates 20.1-20.9

The following intermediates are prepared in analogy to 4-(amino(5-oxo-2-(3-(trifluoro-methyl)phenylamino)cyclopent-1-enyl)methyl)-3-bromobenzonitrile hydrochloride (intermediate 20), using the appropriate starting material as indicated in Table 3.

TABLE 3

| Intermediate | Starting Material | Structure | MS [M + H]$^+$ | Retention time [min] | HPLC-Method |
|---|---|---|---|---|---|
| 20.1 | intermediate 14.1 | 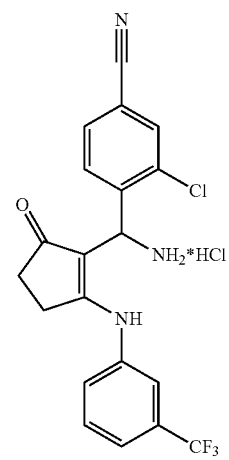 | 406 | 0.51 | X012_S01 |
| 20.2 | intermediate 14.2 | 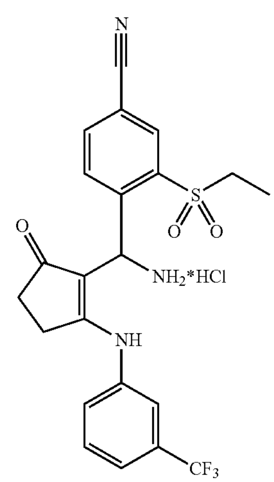 | 464 | 0.50 | X012_S01 |

TABLE 3-continued

| Intermediate | Starting Material | Structure | MS [M + H]⁺ | Retention time [min] | HPLC-Method |
|---|---|---|---|---|---|
| 20.3 | intermediate 14.3 | (structure) | 402 | 0.50 | X012_S01 |
| 20.4 | intermediate 14.4 | (structure) | 386 | 0.51 | X012_S01 |
| 20.5 | intermediate 14.5 | (structure) | 471, 473 | 0.74 | X011_S03 |

TABLE 3-continued
| Intermediate | Starting Material | Structure | MS [M + H]+ | Retention time [min] | HPLC-Method |
|---|---|---|---|---|---|
| 20.6 | intermediate 14.6 | 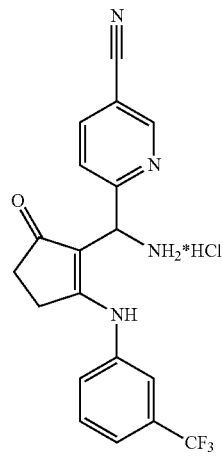 | 373 | 0.82 | Z011_S03 |
| 20.7 | intermediate 16 | 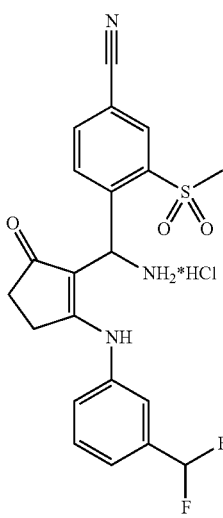 | 432 | 0.80 | Z018_S04 |
| 20.8 | intermediate 18 | 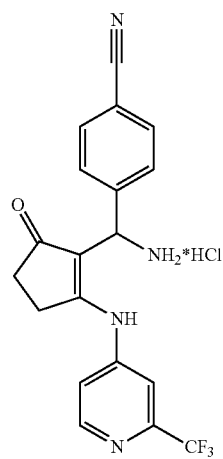 | 373 | 0.76 | Z011_S03 |

TABLE 3-continued

| Intermediate | Starting Material | Structure | MS [M + H]+ | Retention time [min] | HPLC-Method |
|---|---|---|---|---|---|
| 20.9 | intermediate 19 | 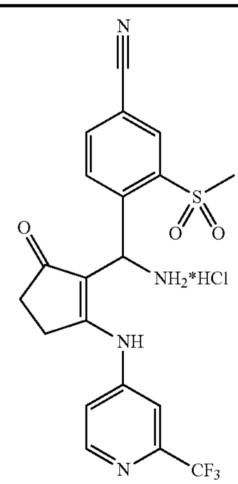 | 451 | 0.76 | Z018_S04 |

INTERMEDIATE 21

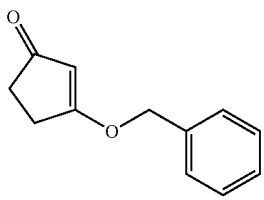

3-(Benzyloxy)cyclopent-2-enone

A mixture of cyclopentane-1,3-dione (2.00 g, 20.4 mmol), benzyl alcohol (2.11 mL, 20.4 mmoL) and para-toluenesulfonic acid (35 mg, 0.20 mmol) in toluene (10.0 mL) is heated at reflux over night. Water is added, and the mixture is extracted with dichloromethane. The organic layer is concentrated, and the residue is purified by flash chromatography on silica (gradient cyclohexane/ethyl acetate 9:1 to cyclohexane/ethyl acetate 1:4). Yield: 1.66 g; ESI mass spectrum: [M+H]+=189; Retention time HPLC: 0.51 min (X012_S01).

INTERMEDIATE 22

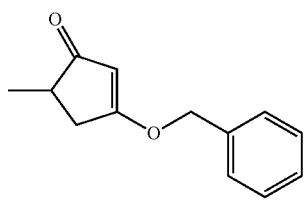

3-(Benzyloxy)-5-methylcyclopent-2-enone

A solution of 3-(benzyloxy)cyclopent-2-enone (intermediate 21, 300 mg, 1.59 mmol) in dry tetrahydrofuran (4.0 mL) is cooled at −50° C. with an acetone/dry ice bath and treated with lithium diisopropylamide (2.0 M in tetrahydrofuran, 890 mL, 1.78 mmol). After 15 min methyl iodide (100 μL, 1.59 mmol) is added, and the mixture is warmed to room temperature over night. Water and dichloromethane is added, and the phases are separated. The organic layer is concentrated under reduced pressure, and the residue is purified by reversed phase HPLC (Waters Xbridge™-$C_{18}$, gradient of acetonitrile in water, 0.1% TFA). Yield: 210 mg; ESI mass spectrum [M+H]+=203; Retention time HPLC: 0.57 min (X012_S01).

INTERMEDIATE 23

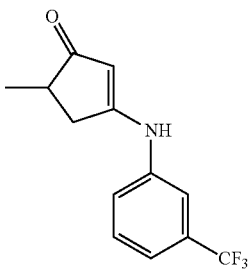

5-Methyl-3-(3-(trifluoromethyl)phenylamino)cyclopent-2-enone

A mixture of 3-(benzyloxy)-5-methylcyclopent-2-enone (intermediate 22, 210 mg, 1.04 mmol) and Palladium on carbon (10%, 127 mg) in toluene (3.0 mL) is treated with hydrogen (3.4 bar) for 9 h. The mixture is filtered, and the filtrate is treated with 3-(tri-fluormethyl)aniline (130 μL, 1.04 mmol) and Ytterbium(III) trifluormethanesulfonate (3 mg, 5 μmol) and stirred at room temperature over night. Another portion of 3-(trifluor-methyl)aniline (65 μL, 0.52 mmol) is added, and the mixture is stirred over night. Water and dichloromethane is added, and the phases are separated. The organic phase is concentrated under reduced pressure, and the residue is purified by reversed phase HPLC (Waters Xbridge™-$C_{18}$, gradient of acetonitrile in water, 0.1% TFA). Yield: 136 mg; ESI mass spectrum [M+H]+=256; Retention time HPLC: 0.55 min (X012_S01).

INTERMEDIATE 24

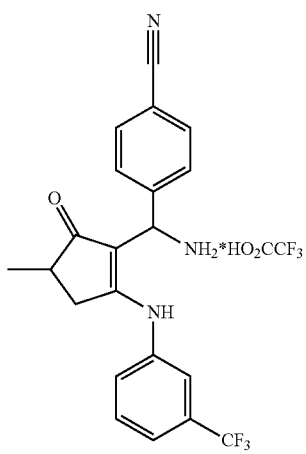

4-(Amino(4-methyl-5-oxo-2-(3-(trifluoromethyl)
phenylamino)cyclopent-1-enyl)-methyl)benzonitrile
trifluoroacetate Sodium hydride (60% in mineral oil, 6 mg, 150 μmol) is added to a mixture of 5-methyl-3-(3-(trifluoromethyl)phenylamino)cyclopent-2-enone (intermediate 23, 38 mg, 150 μmol) and 2-methyltetrahydrofuran (2 mL). After 20 min tert-butyl(4-cyanophenyl)(phenyl-sulfonyl)methylcarbamate (60 mg, 150 μmol based on 90% purity) is added, and the mixture is stirred at room temperature over night. Another portion of sodium hydride (60% in mineral oil, 6 mg, 150 μmol) is added, and the mixture is stirred for 20 min Another portion of tert-butyl(4-cyanophenyl)(phenylsulfonyl)methylcarbamate (60 mg, 150 μmol based on 90% purity) is added, and the mixture is stirred over night. Water is added, and the mixture is extracted twice with dichloromethane. The combined organic layers are concentrated under reduced pressure, and the residue is treated with 1,4-dioxane and hydrogen chloride (4 M in 1,4-dioxane, 290 μL, 1.1 mmol). The mixture is stirred at room temperature over night and treated with another portion of hydrogen chloride (4 M in 1,4-dioxane, 290 μL, 1.1 mmol). The mixture is stirred over night and treated with water. The mixture is extracted with dichloromethane, and the organic layer is concentrated under reduced pressure. The residue is purified by reversed phase HPLC (Waters Xbridge™-$C_{18}$, gradient of acetonitrile in water, 0.1% TFA). Yield: 24 mg; ESI mass spectrum [M+H]$^+$=386; Retention time HPLC: 0.49 min (X012_S01).

INTERMEDIATE 25

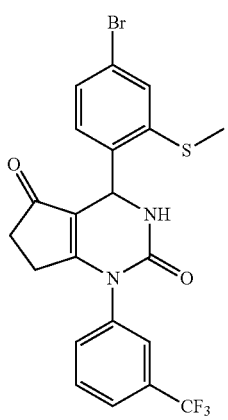

4-(4-Bromo-2-(methylthio)phenyl)-1-(3-(trifluoromethyl)phenyl)-3,4,6,7-tetrahydro-1H-cyclopenta[d]pyrimidine-2,5-dione Triethylamine (250 μL, 1.81 mmol) is added to a mixture of 2-(amino(4-bromo-2-(methyl-thio)phenyl)methyl)-3-(3-(trifluoromethyl)phenyl amino)cyclopent-2-enone hydrochloride (intermediate 20.5, 4.08 g, 7.23 mmol based on 90% purity) and 1,1'-carbonyldiimidazole (1.46 g, 9.04 mmol) in acetonitrile (54 mL), and the mixture is stirred at room temperature for 1 h. All volatiles are removed under reduced pressure, and the residue is treated with water. The precipitate is filtered and purified by flash chromatography on silica (gradient dichloromethane to dichloromethane/methanol 95:5). Yield: 3.04 g; ESI mass spectrum: [($^{79}$Br)-M+H]$^+$=497, [($^{81}$Br)-M+H]$^+$=499; Retention time HPLC: 0.65 min (X011_S03).

INTERMEDIATE 26

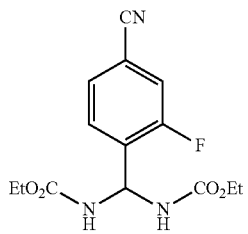

Diethyl
(4-Cyano-2-fluorophenyl)methylenedicarbamate

In a three-necked round bottom flask equipped with a drying tube filled with calcium chloride and an inlet for nitrogen, 3-fluoro-4-formylbenzonitrile (5.00 g, 33.5 mmol) and ethyl carbamate (6.57 g, 73.7 mmol) are heated at 150° C. The flask is being purged with a flow of nitrogen, and concentrated sulfuric acid (200 μL) is added drop by drop within 10 min. The mixture is heated at 150° C. for 6 h and then cooled at room temperature. The mixture is ground, treated with water (400 mL) and then stirred for 3 h. The precipitate is filtered and dried. Yield: 6.50 g; ESI mass spectrum: [M+Na]$^+$=332; Retention time HPLC: 0.58 min (Z011_S03).

INTERMEDIATE 27

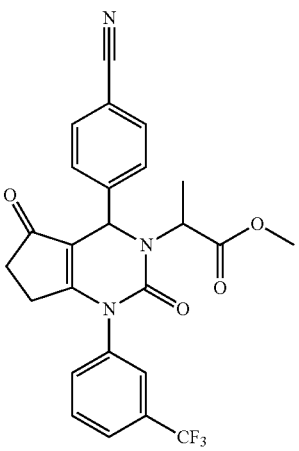

Methyl 2-(4-(4-Cyanophenyl)-2,5-dioxo-1-(3-(trifluoromethyl)phenyl)-6,7-dihydro-1H-cyclopenta[d]pyrimidin-3(2H,4H,5H)-yl)propanoate Cesium carbonate (737 mg, 2.26 mmol) is added to a solution of 4-(2,5-dioxo-1-(3-(tri-fluoromethyl)phenyl)-2,3,4,5,6,7-hexahydro-1H-cyclopenta[d]pyrimidin-4-yl)benzonitrile (example 1, 300 mg, 0.76 mmol) and methyl 2-bromopropionate (252 mg, 1.51 mmol) in N,N-dimethylformamide (10.0 mL), and the mixture is stirred at 50° C. over night. Water is added, and the mixture is extracted with dichloromethane. The organic layer is washed twice with water, dried over MgSO$_4$ and concentrated under reduced pressure. The residue is purified by reversed phase HPLC (Waters SunFire™-C$_{18}$, gradient of acetonitrile in water, 0.1% TFA). Yield: 160 mg; ESI mass spectrum: [M+H]$^+$=484; Retention time HPLC: 0.85 min (Z018_S04).

INTERMEDIATE 28

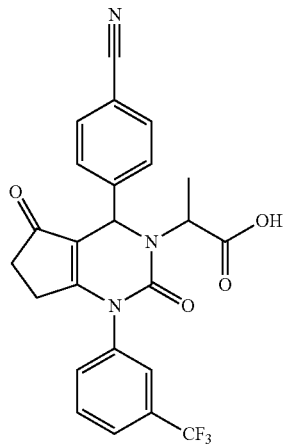

2-(4-(4-Cyanophenyl)-2,5-dioxo-1-(3-(trifluoromethyl)phenyl)-6,7-dihydro-1H-cyclopenta[d]pyrimidin-3(2H,4H,5H)-yl)propanoic acid A solution of methyl 2-(4-(4-cyanophenyl)-2,5-dioxo-1-(3-(trifluoromethyl)phenyl)-6,7-dihydro-1H-cyclopenta[d]pyrimidin-3(2H,4H,5H)-yl)propanoate (intermediate 27, 125 mg, 0.26 mmol) in 1,4-dioxane (3 mL) is treated with aqueous lithium hydroxide (2.0 M, 390 µL, 0.78 mmol), and the mixture is stirred at room temperature over night. Water is added, and the mixture is extracted with dichloromethane. The aqueous phase is acidified with 1M aqueous hydrogen chloride and extracted with dichloromethane. The combined organic layers are dried over Na$_2$SO$_4$ and concentrated under reduced pressure. Yield: 91 mg; ESI mass spectrum: [M+H]$^+$=470; Retention time HPLC: 0.85 min (Z018_S04).

INTERMEDIATE 29

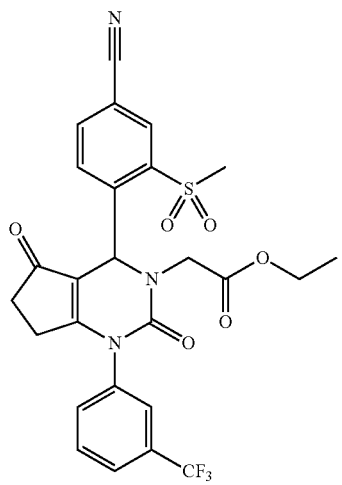

Ethyl 2-(4-(4-Cyano-2-(methylsulfonyl)phenyl)-2,5-dioxo-1-(3-(trifluoromethyl)-phenyl)-6,7-dihydro-1H-cyclopenta[d]pyrimidin-3(2H,4H,5H)-yl)acetate A mixture of 4-(2,5-dioxo-1-(3-(trifluoromethyl)phenyl)-2,3,4,5,6,7-hexahydro-1H-cyclopenta[d]pyrimidin-4-yl)-3-(methylsulfonyl)benzonitrile (example 10, 1.78 g, 3.74 mmol) and cesium carbonate (1.83 g, 5.62 mmol) in N,N-dimethylformamide (25.0 mL) is treated with ethyl bromoacetate (0.50 mL, 4.50 mml), and the mixture is stirred at room temperature over night. Water (30 ml) is added, and the precipitate is filtered and dried. Yield: 1.80 g; ESI mass spectrum: [M+H]$^+$=562; Retention time HPLC: 1.05 min (Z018_S04).

Intermediates 30.1-30.3

The following intermediates are prepared in analogy to 4-nitrophenyl 4-(4-cyanophenyl)-2,5-dioxo-1-(3-(trifluoromethyl)phenyl)-4,5,6,7-tetrahydro-1H-cyclopenta[d]pyrimidine-3(2H)-carboxylate (intermediate 4), using the appropriate starting material as indicated in Table 4, and substituting dichloromethane with acetonitrile as solvent.

TABLE 4
| Intermediate | Starting Material | Structure | MS [M + H]+ | Retention time [min] | HPLC- Method |
|---|---|---|---|---|---|
| 30.1 | example 1A | 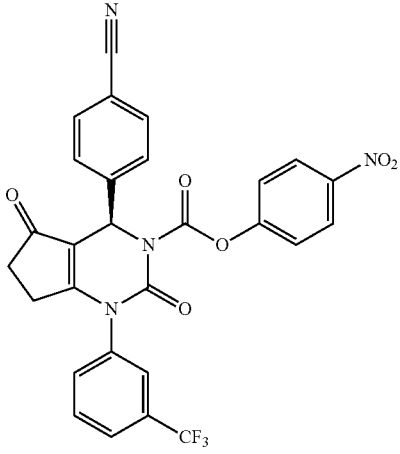 [SMILES: N#Cc1ccc([C@@H]2C3=C(CCC3=O)N(c3cccc(C(F)(F)F)c3)C(=O)N2C(=O)Oc2ccc([N+](=O)[O-])cc2)cc1] | 563 | 1.12 | Z018_S04 |
| 30.2 | example 10A | 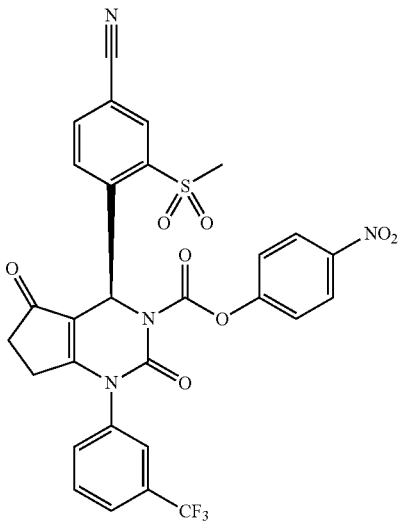 [SMILES: CS(=O)(=O)c1cc(C#N)ccc1[C@@H]1C2=C(CCC2=O)N(c2cccc(C(F)(F)F)c2)C(=O)N1C(=O)Oc1ccc([N+](=O)[O-])cc1] | 641 | 1.10 | Z018_S04 |
| 30.3 | example 15.5 | 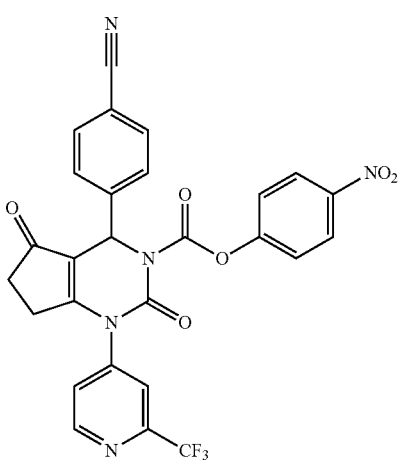 [SMILES: N#Cc1ccc(C2C3=C(CCC3=O)N(c3ccnc(C(F)(F)F)c3)C(=O)N2C(=O)Oc2ccc([N+](=O)[O-])cc2)cc1] | 564 | 1.09 | Z018_S04 |

Syntheses of Examples

EXAMPLE 1

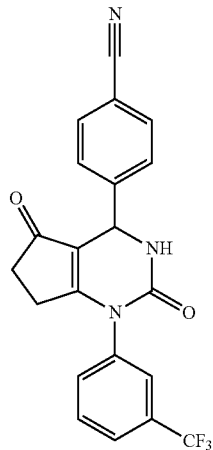

4-(2,5-Dioxo-1-(3-(trifluoromethyl)phenyl)-2,3,4,5,6,7-hexahydro-1H-cyclopenta[d]-pyrimidin-4-yl)benzonitrile Method A:

A solution of 3-(3-(trifluoromethyl)phenylamino)cyclopent-2-enone (1.00 g, 4.15 mmol) in dichloromethane (10 mL) is added dropweise over the period of 1 h to a solution of 4-(chloro(isocyanato)methyl)benzonitrile (intermediate 2, 1.04 g, 5.39 mmol) in dichloromethane (15 mL) at 30° C. The reaction mixture is heated at reflux for 4 h and then stirred over night at room temperature. The reaction mixture is purified by reversed phase HPLC (Waters Xbridge™-$C_{18}$, gradient of acetonitrile in water, 0.1% $NH_3$). Yield: 472 mg; ESI mass spectrum [M+H]$^+$=398; Retention time HPLC: 1.00 min (V011_S01).

Method B:

Under an atmosphere of argon, a mixture of 4-(4-bromophenyl)-1-(3-(trifluoromethyl)-phenyl)-3,4,6,7-tetrahydro-1H-cyclopenta[d]pyrimidine-2,5-dione (intermediate 3, 500 mg, 1.11 mmol), zinc cyanide (200 mg, 1.70 mmol) and tetrakis(triphenylphosphine)-palladium(0) (130 mg, 112 µmol) in N,N-dimethylformamide (5 mL) is heated over night at 110° C. The reaction mixture is cooled to room temperature, and water is added. The mixture is extracted twice with dichloromethane, and the combined organic layers are concentrated. The residue is purified by flash column chromatography on silica (gradient dichloromethane to dichloromethane/methanol 99:1). Yield: 190 mg; ESI mass spectrum [M+H]$^+$=398; Retention time HPLC: 1.00 min (V011_801).

Method C:

A mixture of 4-(amino(5-oxo-2-(3-(trifluoromethyl)phenylamino)cyclopent-1-enyl)-methyl)benzonitrile hydrochloride (intermediate 13, 11.8 g, 26.1 mmol based on 90% purity) in acetonitrile (100 mL) and 1,1'-carbonyldiimidazole (5.28 g, 32.6 mmol) is treated with triethylamine (0.9 mL, 6.5 mmol), and the mixture is stirred at room temperature for 1 h. All volatiles are removed under reduced pressure, and the residue is treated with water. The precipitate is filtered, washed with water and dried. The residue is purified by recrystallization from hot toluene (130 mL). Yield: 8.6 g; ESI mass spectrum [M+H]$^+$=398; Retention time HPLC: 1.06 min (V011_S01). LH4BRM00213

Examples 1A and 1B

Enantiomers of Example 1

The enantiomers of racemic 4-(2,5-dioxo-1-(3-(trifluoromethyl)phenyl)-2,3,4,5,6,7-hexahydro-1H-cyclopenta[d]pyrimidin-4-yl)benzonitrile (example 1, 190 mg, 1.11 mmol) are separated by preparative supercritical fluid chromatography on a chiral phase (Daicel Chiralpak IC, 10×250 mm, 5 µm, 30% MeOH+0.2% diethylamine in supercritical $CO_2$, 40° C., 100 bar back pressure).

EXAMPLE 1A

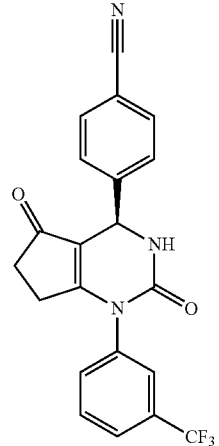

(R)-4-(2,5-Dioxo-1-(3-(trifluoromethyl)phenyl)-2,3,4,5,6,7-hexahydro-1H-cyclopenta[d]pyrimidin-4-yl)benzonitrile Yield 67 mg; ESI mass spectrum [M+H]$^+$=398; Retention time: 9.28 min (late eluting enantiomer) (I_IC_30_MeOH_DEA).

EXAMPLE 1B

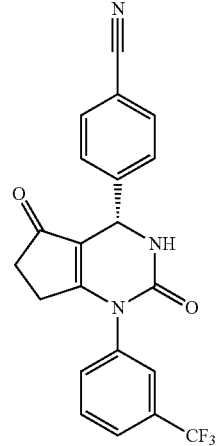

(S)-4-(2,5-Dioxo-1-(3-(trifluoromethyl)phenyl)-2,3,4,5,6,7-hexahydro-1H-cyclopenta[d]pyrimidin-4-yl)benzonitrile Yield 74 mg; ESI mass spectrum [M+H]$^+$=398; Retention time: 2.86 min (early eluting enantiomer) (I_IC_30_MeOH_DEA).

Alternatively, example 1A can be prepared as follows:

Under an atmosphere of argon, a mixture of (R)-4-(4-bromophenyl)-1-(3-(trifluoromethyl)-phenyl)-3,4,6,7-tetrahydro-1H-cyclopenta[d]pyrimidine-2,5-dione (intermediate 3A, 1.00 g, 2.22 mmol), zinc cyanide (442 mg, 3.76 mmol) and tetrakis(triphenylphosphine)-palladium(0) (256 mg, 222 µmol) in N,N-dimethylformamide (10 mL) is heated at 110° C. for 1 h. The reaction mixture is cooled to room temperature and then purified by preparative reversed-phase HPLC (Waters Xbridge™-C$_{18}$, gradient of methanol in water, 0.1% TFA). Yield: 247 mg; ESI mass spectrum [M+H]$^+$=398; Retention time HPLC: 0.53 min (X012_S01).

EXAMPLE 2

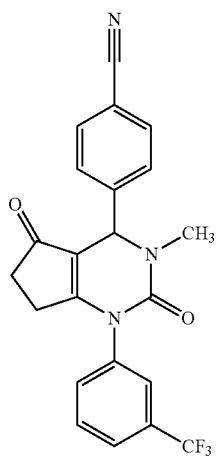

4-(3-Methyl-2,5-dioxo-1-(3-(trifluoromethyl)phenyl)-2,3,4,5,6,7-hexahydro-1H-cyclopenta[d]pyrimidin-4-yl)benzonitrile Under an atmosphere of argon, 4-(2,5-dioxo-1-(3-(trifluoromethyl)phenyl)-2,3,4,5,6,7-hexahydro-1H-cyclopenta[d]pyrimidin-4-yl)benzonitrile (example 1, 200 mg, 0.50 mmol) is added to a suspension of sodium hydride (60% in mineral oil, 24 mg, 0.60 mmol) in dry tetrahydrofuran. After 20 min, methyl iodide (41 µL, 0.66 mmol) is added. After 20 min water is added and the mixture is concentrated. The residue is purified by flash a) chromatography on silica (gradient cyclohexane/ethyl acetate 1:1 to ethyl acetate). Yield: 49 mg; ESI mass spectrum [M+H]$^+$=412; Retention time HPLC: 0.59 min (X012_S01).

EXAMPLE 2A

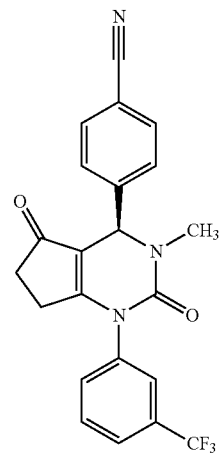

(R)-4-(3-Methyl-2,5-dioxo-1-(3-(trifluoromethyl)phenyl)-2,3,4,5,6,7-hexahydro-1H-cyclopenta[d]pyrimidin-4-yl)benzonitrile The title compound is prepared in analogy to 4-(3-methyl-2,5-dioxo-1-(3-(trifluoromethyl)-phenyl)-2,3,4,5,6,7-hexahydro-1H-cyclopenta[d]pyrimidin-4-yl)benzonitrile (example 2), using (R)-4-(2,5-dioxo-1-(3-(trifluoromethyl)phenyl)-2,3,4,5,6,7-hexahydro-1H-cyclopenta[d]pyrimidin-4-yl)benzonitrile (example 1A, 40 mg, 0.10 mmol) as starting material. Yield: 20 mg; ESI mass spectrum [M+H]$^+$=412; Retention time HPLC: 0.59 min (X012_801).

EXAMPLE 3

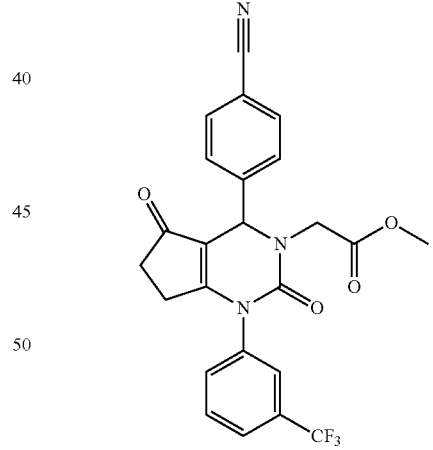

Methyl 2-(4-(4-Cyanophenyl)-2,5-dioxo-1-(3-(trifluoromethyl)phenyl)-6,7-dihydro-1H-cyclopenta[d]pyrimidin-3(2H,4H,5H)-yl)acetate A solution of 4-(2,5-dioxo-1-(3-(trifluoromethyl)phenyl)-2,3,4,5,6,7-hexahydro-1H-cyclopenta[d]pyrimidin-4-yl)benzonitrile (example 1, 3.00 g, 7.55 mmol) in dry acetonitrile (45 mL) is cooled in an ice bath and treated dropwise with lithium diisopropylamide (2 M in THF, 7.55 mL, 15.1 mmol), while the temperature is kept below 5° C. Methyl 2-bromoacetate (2.31 g, 15.1 mmol) is added and the mixture is stirred for 1.5 h. The mixture is then warmed to room temperature and stirred at room temperature over night. Water (0.5 mL) is added, the mixture is concentrated, and the residue is purified by reversed phase HPLC (Waters SunFire™-$C_{18}$, gradient of acetonitrile in water, 0.1% TFA). Yield: 2.64 g; ESI mass spectrum $[M+H]^+$=470; Retention time HPLC: 1.65 min (W018_801).

EXAMPLE 4

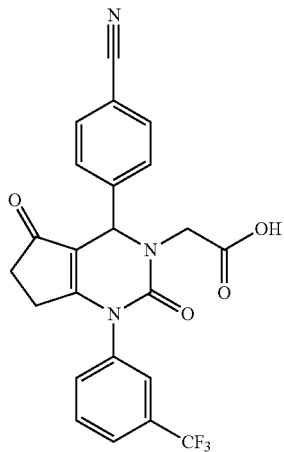

2-(4-(4-Cyanophenyl)-2,5-dioxo-1-(3-(trifluoromethyl)phenyl)-6,7-dihydro-1H-cyclopenta[d]pyrimidin-3(2H,4H,5H)-yl)acetic acid Aqueous sodium hydroxide solution (1 M, 15.0 mL, 15.0 mmol) is added to a solution of methyl 2-(4-(4-cyanophenyl)-2,5-dioxo-1-(3-(trifluoromethyl)phenyl)-6,7-dihydro-1H-cyclopenta[d]pyrimidin-3(2H,4H,5H)-yl)acetate (example 3, 2.64 g, 5.62 mmol) in tetrahydrofuran (40 mL) and the mixture is stirred at room temperature for 4 h. Water is added and the mixture is extracted three times with ethyl acetate. The aqueous layer is acidified a) with hydrogen chloride and extracted twice with dichloromethane. These organic layers are combined and concentrated. Yield: 1.84 g; ESI mass spectrum $[M+H]^+$=456; Retention time HPLC: 0.84 min (Z018_S04).

EXAMPLE 5

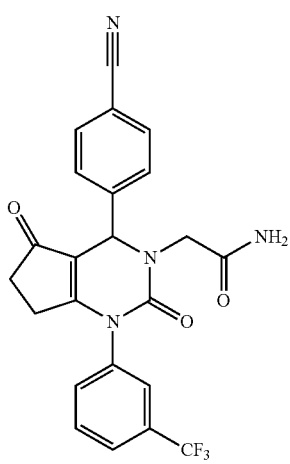

2-(4-(4-Cyanophenyl)-2,5-dioxo-1-(3-(trifluoromethyl)phenyl)-6,7-dihydro-1H-cyclopenta[d]pyrimidin-3(2H,4H,5H)-yl)acetamide N,N,N',N'-Tetramethyl-O-(benzotriazol-1-yl)uronium tetrafluoroborate (43 mg, 0.13 mmol) is added to a solution of 2-(4-(4-cyanophenyl)-2,5-dioxo-1-(3-(trifluoro-methyl)phenyl)-6,7-dihydro-1H-cyclopenta[d]pyrimidin-3(2H,4H,5H)-yl)acetic acid (example 4, 60 mg, 0.13 mmol) and N,N-diisopropylethylamine (50 µL, 0.29 mmol) in N,N-dimethylformamide (0.5 mL). After 20 min aqueous ammonia (32%, 8 µL, 0.13 mmol) added and the mixture is stirred at room temperature for 1 h. The mixture is purified by reversed phase HPLC (Waters Xbridge™-$C_{18}$, gradient of acetonitrile in water, 0.1% TFA). Yield: 36 mg; ESI mass spectrum $[M+H]^+$=455; Retention time HPLC: 0.50 min (X012_S01).

EXAMPLE 6

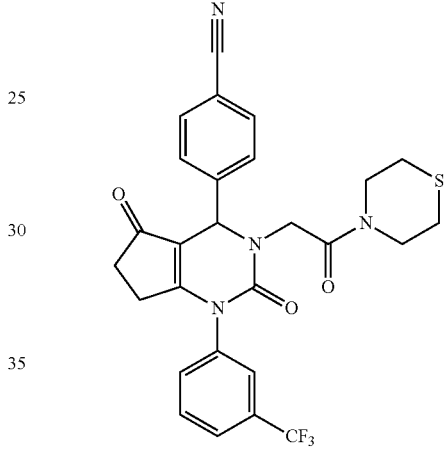

4-(2,5-Dioxo-3-(2-oxo-2-thiomorpholinoethyl)-1-(3-(trifluoromethyl)phenyl)-2,3,4,5,6,7-hexahydro-1H-cyclopenta[d]pyrimidin-4-yl)benzonitrile A solution of 2-(4-(4-cyanophenyl)-2,5-dioxo-1-(3-(trifluoromethyl)phenyl)-6,7-dihydro-1H-cyclopenta[d]pyrimidin-3(2H,4H,5H)-yl)acetic acid (example 4, 30 mg, 66 µmol) and triethylamine (30 µL, 0.22 mmol) in N,N-dimethylformamide (1.25 mL) is treated with N,N,N',N'-tetramethyl-O-(benzotriazol-1-yl)uronium tetrafluoroborate (21 mg, 66 µmol) and stirred at room temperature for 15 min. This mixture is then added to a solution of thiomorpholine (13 mg, 0.13 mmol) in N,N-dimethylformamide (0.25 mL) and stirred for 72 h. The mixture is filtered and the filtrate is purified by reversed phase HPLC (Waters Xbridge™-$C_{18}$, gradient of methanol in water, 0.1% $NH_3$). Yield: 20 mg; ESI mass spectrum $[M+H]^+$=541; Retention time HPLC: 1.17 min (001_CA03).

Examples 6.1-6.46

The following examples of Table 5 are prepared in analogy to example 6, replacing thiomorpholine with the appropriate amine as starting material.

TABLE 5
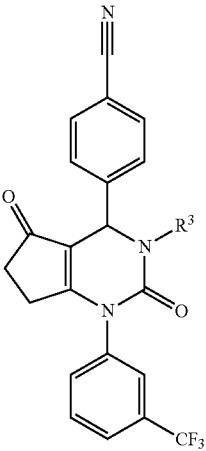
| Example | R³ | MS [M + H]⁺ | Retention time [min] | HPLC-Method |
|---|---|---|---|---|
| 6.1 | 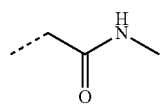 | 469 | 1.14 | 001_CA03 |
| 6.2 | 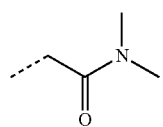 | 483 | 1.16 | 001_CA03 |
| 6.3 | 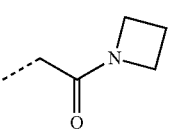 | 495 | 0.83 | Z018_S04 |
| 6.4 | 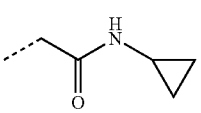 | 495 | 1.18 | 001_CA03 |
| 6.5 | 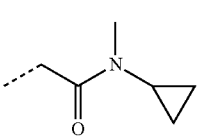 | 509 | 1.23 | 001_CA03 |
| 6.6 | 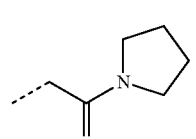 | 509 | 1.22 | 001_CA03 |
| 6.7 | 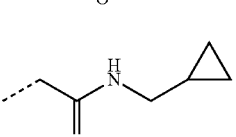 | 509 | 1.24 | 001_CA03 |
| 6.8 | 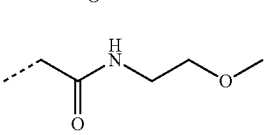 | 513 | 1.15 | 001_CA03 |

TABLE 5-continued

| Example | R³ | MS [M + H]⁺ | Retention time [min] | HPLC-Method |
|---|---|---|---|---|
| 6.9 | (3-azabicyclo[3.1.0]hexan-3-yl)methylcarbonyl | 521 | 0.88 | Z011_S03 |
| 6.10 | piperidin-1-ylmethylcarbonyl | 523 | 1.29 | 001_CA03 |
| 6.11 | (3-hydroxypyrrolidin-1-yl)methylcarbonyl | 525 | 1.01 | 001_CA03 |
| 6.12 | morpholin-4-ylmethylcarbonyl | 525 | 1.17 | 001_CA03 |
| 6.13 | (3-fluoropyrrolidin-1-yl)methylcarbonyl | 527 | 1.19 | 001_CA03 |
| 6.14 | (4-methylpiperidin-1-yl)methylcarbonyl | 537 | 1.36 | 001_CA03 |
| 6.15 | (3-oxopiperazin-1-yl)methylcarbonyl | 538 | 0.97 | 001_CA03 |

TABLE 5-continued

| Example | R³ | MS [M + H]⁺ | Retention time [min] | HPLC-Method |
|---|---|---|---|---|
| 6.16 | | 538 | 1.02 | 001_CA03 |
| 6.17 | | 538 | 0.90 | 001_CA03 |
| 6.18 | | 539 | 1.11 | 001_CA03 |
| 6.19 | | 539 | 1.09 | 001_CA03 |
| 6.20 | | 539 | 1.11 | 001_CA03 |
| 6.21 | | 539 | 1.18 | 001_CA03 |
| 6.22 | | 545 | 1.01 | 001_CA03 |
| 6.23 | | 549 | 1.08 | 001_CA03 |

TABLE 5-continued

| Example | R³ | MS [M + H]⁺ | Retention time [min] | HPLC-Method |
|---|---|---|---|---|
| 6.24 | (5-methyl-1,3,4-oxadiazol-2-yl)methyl-NH-C(O)-CH₂- | 551 | 1.07 | 001_CA03 |
| 6.25 | (4-methyl-3-oxopiperazin-1-yl)-C(O)-CH₂- | 552 | 1.03 | 001_CA03 |
| 6.26 | (5-oxopyrrolidin-2-yl)methyl-NH-C(O)-CH₂- | 552 | 1.04 | 001_CA03 |
| 6.27 | 2-(pyrrolidin-1-yl)ethyl-NH-C(O)-CH₂- | 552 | 0.91 | 001_CA03 |
| 6.28 | (1-methylpyrrolidin-2-yl)methyl-NH-C(O)-CH₂- | 552 | 0.90 | 001_CA03 |
| 6.29 | (1-methylpiperidin-4-yl)-NH-C(O)-CH₂- | 552 | 0.91 | 001_CA03 |
| 6.30 | (4-methoxypiperidin-1-yl)-C(O)-CH₂- | 553 | 1.14 | 001_CA03 |

TABLE 5-continued

| Example | R³ | MS [M + H]⁺ | Retention time [min] | HPLC-Method |
|---------|----|-----|-----|-----|
| 6.31 | | 553 | 1.05 | 001_CA03 |
| 6.32 | | 553 | 1.08 | 001_CA03 |
| 6.33 | | 553 | 1.15 | 001_CA03 |
| 6.34 | | 553 | 1.15 | 001_CA03 |
| 6.35 | | 554 | 1.02 | 001_CA03 |
| 6.36 | | 554 | 0.91 | 001_CA03 |
| 6.37 | | 557 | 0.98 | 001_CA03 |

TABLE 5-continued
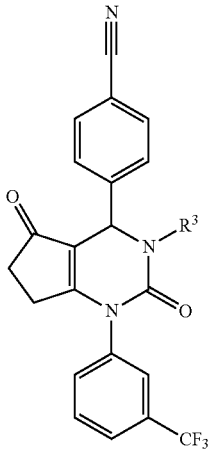
| Example | R³ | MS [M + H]⁺ | Retention time [min] | HPLC-Method |
|---|---|---|---|---|
| 6.38 | 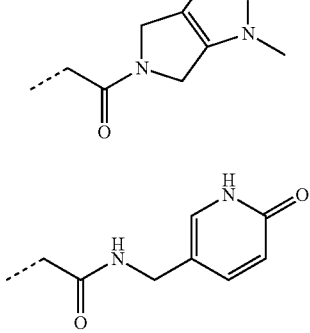 | 561 | 1.10 | 001_CA03 |
| 6.39 | 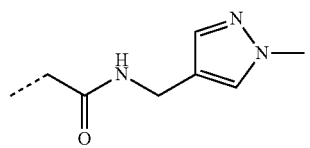 | 562 | 0.99 | 001_CA03 |
| 6.40 | 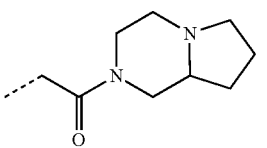 | 563 | 1.07 | 001_CA03 |
| 6.41 | 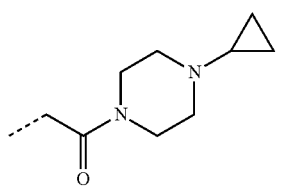 | 564 | 0.83 | 001_CA03 |
| 6.42 | 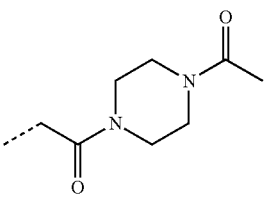 | 564 | 0.90 | 001_CA03 |
| 6.43 | | 566 | 1.10 | 001_CA03 |

TABLE 5-continued

[Structure shown at top of table with cyanophenyl, cyclopentapyrimidine-dione core, and trifluoromethylphenyl groups; R³ as variable substituent]

| Example | R³ | MS [M + H]⁺ | Retention time [min] | HPLC-Method |
|---------|-----|-------------|---------------------|-------------|
| 6.44 | [structure] | 566 | 1.06 | 001_CA03 |
| 6.45 | [structure] | 566 | 1.06 | 001_CA03 |
| 6.46 | [structure] | 588 | 1.02 | 001_CA03 |

EXAMPLE 7

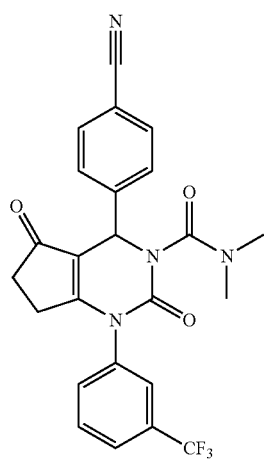

4-(4-Cyanophenyl)-N,N-dimethyl-2,5-dioxo-1-(3-(trifluoromethyl)phenyl)-4,5,6,7-tetrahydro-1H-cyclopenta[d]pyrimidine-3(2H)-carboxamide A solution of 4-nitrophenyl 4-(4-cyanophenyl)-2,5-dioxo-1-(3-(trifluoromethyl)phenyl)-4,5,6,7-tetrahydro-1H-cyclopenta[d]pyrimidine-3(2H)-carboxylate (intermediate 4, 60 mg, 0.11 mmol) in acetonitrile (1.5 mL) is treated with dimethylamine (2.0 M in tetrahydrofuran, 270 µL, 0.53 mmol) and the mixture is stirred at room temperature for 30 min. Water and N,N-dimethylformamide are added and the mixture is purified by reversed phase HPLC (Waters Xbridge™-C₁₈, gradient of acetonitrile in water, 0.1% NH₃). Yield 28 mg, ESI mass spectrum [M+H]⁺=469; Retention time HPLC: 0.87 min (Z018_S04).

Examples 7.1-7.11

The following examples of Table 6 are prepared in analogy to example 7, replacing dimethylamine with the appropriate amine as reagent.

TABLE 6

[Structure: 4-(4-cyanophenyl)-1-(3-(trifluoromethyl)phenyl)-3-R³-cyclopenta-pyrimidine-2,5-dione core]

| Example | R³ | MS [M + H]⁺ | Retention time [min] | HPLC-Method |
|---|---|---|---|---|
| 7.1 | -C(O)NH-CH₃ | 455 | 0.88 | Z011_S03 |
| 7.2 | -C(O)NH-CH₂CH₂OH | 485 | 0.85 | Z018_S04 |
| 7.3 | -C(O)NH-CH₂CH₂CH₂OH | 499 | 0.86 | Z018_S04 |
| 7.4 | -C(O)NH-CH₂CH₂OCH₃ | 499 | 0.93 | Z018_S04 |
| 7.5 | -C(O)NH-CH₂CH₂N(CH₃)₂ | 512 | 0.72 | Z018_S04 |
| 7.6 | -C(O)NH-CH₂CH₂S(O)CH₃ | 531 | 0.83 | Z018_S04 |
| 7.7 | -C(O)NH-CH₂-(1-methylpyrazol-3-yl) | 535 | 0.91 | Z018_S04 |

TABLE 6-continued

| Example | R³ | MS [M + H]⁺ | Retention time [min] | HPLC-Method |
|---|---|---|---|---|
| 7.8 | (acetamido-methyl-5-oxopyrrolidine) | 538 | 0.84 | Z018_S04 |
| 7.9 | (acetamido-1-methyl-5-oxopyrrolidine) | 538 | 0.85 | Z018_S04 |
| 7.10 | (acetamido-ethyl-methylsulfone) | 547 | 0.87 | Z018_S04 |
| 7.11 | (acetamido-methyl-5-methylsulfonylpyridine) | 610 | 0.9 | Z018_S04 |

Examples 7.1A and 7.1B: Enantiomers of Example 7.1

The enantiomers of racemic 4-(4-cyanophenyl)-N-methyl-2,5-dioxo-1-(3-(trifluoro-methyl)phenyl)-4,5,6,7-tetrahydro-1H-cyclopenta[d]pyrimidine-3(2H)-carboxamide (example 7.1, 124 mg, 0.27 mmol) are separated by preparative supercritical fluid chromatography on a chiral phase (Daicel Chiralpak AD-H, 20×250 mm, 5 µm, 20% iso-PrOH+0.2% diethylamine in supercritical $CO_2$, 40° C., 150 bar back pressure).

EXAMPLE 7.1A

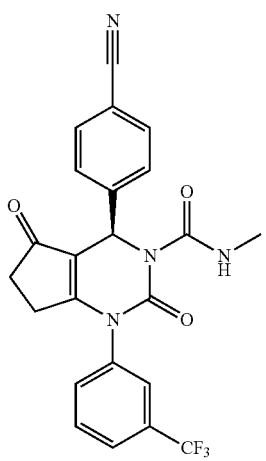

(R)-4-(4-Cyanophenyl)-N-methyl-2,5-dioxo-1-(3-(trifluoromethyl)phenyl)-4,5,6,7-tetrahydro-1H-cyclopenta[d]pyrimidine-3(2H)-carboxamide Yield: 48 mg; ESI mass spectrum [M+H]$^+$=455; Retention time: 1.26 min (early eluting enantiomer) (I_IB_30_MeOH_DEA).

EXAMPLE 7.1B

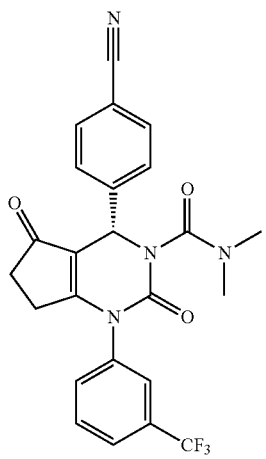

(S)-4-(4-Cyanophenyl)-N-methyl-2,5-dioxo-1-(3-(trifluoromethyl)phenyl)-4,5,6,7-tetrahydro-1H-cyclopenta[d]pyrimidine-3(2H)-carboxamide Yield: 40 mg; ESI mass spectrum [M+H]$^+$=455; Retention time: 5.24 min (late eluting enantiomer) (I_IB_30_MeOH_DEA).

Examples 7.2A and 7.2B

Enantiomers of Example 7.2

The enantiomers of racemic 4-(4-cyanophenyl)-N-(2-hydroxyethyl)-2,5-dioxo-1-(3-(trifluoromethyl)phenyl)-4,5,6,7-tetrahydro-1H-cyclopenta[d]pyrimidine-3(2H)-carboxamide (example 7.2, 223 mg, 0.46 mmol) are separated by preparative supercritical fluid chromatography on a chiral phase (Daicel Chiralpak IB, 20×250 mm, 5 μm, 30% MeOH+0.2% diethylamine in supercritical $CO_2$, 40° C., 120 bar back pressure).

EXAMPLE 7.2A

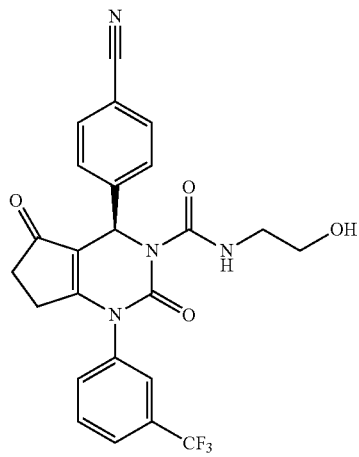

(R)-4-(4-Cyanophenyl)-N-(2-hydroxyethyl)-2,5-dioxo-1-(3-(trifluoromethyl)phenyl)-4,5,6,7-tetrahydro-1H-cyclopenta[d]pyrimidine-3(2H)-carboxamide Yield: 78 mg; ESI mass spectrum [M+H]$^+$=485; Retention time: 1.36 min (early eluting enantiomer) (I_IB_30_MeOH_DEA).

EXAMPLE 7.2B

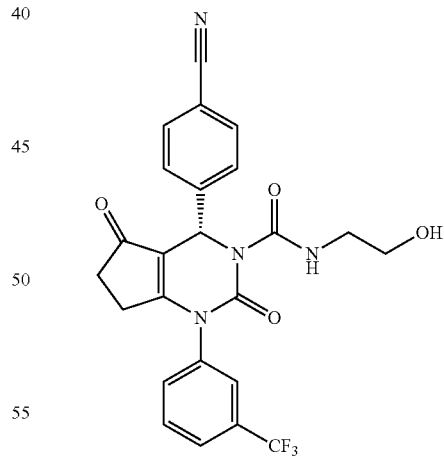

(S)-4-(4-Cyanophenyl)-N-(2-hydroxyethyl)-2,5-dioxo-1-(3-(trifluoromethyl)phenyl)-4,5,6,7-tetrahydro-1H-cyclopenta[d]pyrimidine-3(2H)-carboxamide Yield: 99 mg; ESI mass spectrum [M+H]$^+$=485; Retention time: 3.38 min (early eluting enantiomer) (I_IB_30_MeOH_DEA).

EXAMPLE 8

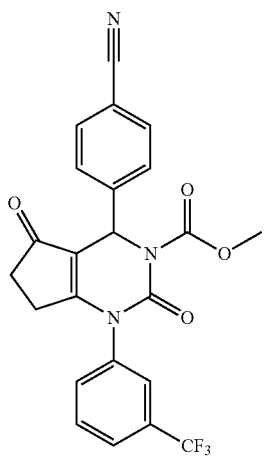

Methyl 4-(4-Cyanophenyl)-2,5-dioxo-1-(3-(trifluoromethyl)phenyl)-4,5,6,7-tetrahydro-1H-cyclopenta[d]pyrimidine-3(2H)-carboxylate A solution of 4-(2,5-dioxo-1-(3-(trifluoromethyl)phenyl)-2,3,4,5,6,7-hexahydro-1H-cyclopenta[d]pyrimidin-4-yl)benzonitrile (example 1, 30 mg, 0.076 mmol) in tetrahydrofuran (0.5 mL) is added to a suspension of sodium hydride (60% in mineral oil, 4 mg, 0.1 mmol) in dry tetrahydrofuran. After 20 min methyl chloroformate (6 μL, 0.078 mmol) is added, and the mixture is stirred at room temperature for 1 h. Water is added and the mixture is a) extracted with dichloromethane. The combined organic layers are concentrated, and the residue is purified by reversed phase HPLC (Waters Xbridge™-$C_{18}$, gradient of acetonitrile in water, 0.1% $NH_3$). Yield: 2 mg; ESI mass spectrum $[M+H]^+$=456; Retention time HPLC: 1.10 min (V011_S01).

EXAMPLE 9

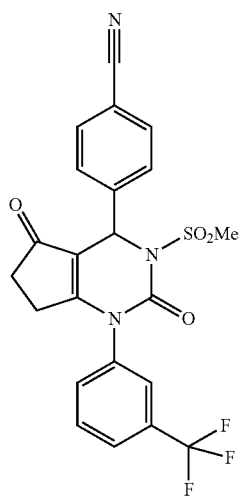

4-(3-(Methylsulfonyl)-2,5-dioxo-1-(3-(trifluoromethyl)phenyl)-2,3,4,5,6,7-hexahydro-1H-cyclopenta[d]pyrimidin-4-yl)benzonitrile 4-(2,5-Dioxo-1-(3-(trifluoromethyl)phenyl)-2,3,4,5,6,7-hexahydro-1H-cyclopenta[d]-pyrimidin-4-yl)benzonitrile (example 1, 255 mg, 0.64 mmol) is added to a suspension of sodium hydride (60% in mineral oil, 72 mg, 1.8 mmol) in dry tetrahydrofuran (15 mL) and the mixture is stirred at room temperature for 10 min. Methanesulfonyl chloride (104 μL, 1.35 mmol) is added and the mixture is stirred at 50° C. for 2 h. Water (1 mL) is added and the mixture is purified by reversed phase HPLC (Waters SunFire™-$C_{18}$, gradient of acetonitrile in water, 0.1% TFA). Yield: 230 mg; ESI mass spectrum $[M+H]^+$=476; Retention time HPLC: 0.91 min (Z018_S04).

Examples 9A and 9B

Enantiomers of Example 9

The enantiomers of racemic 4-(3-(methylsulfonyl)-2,5-dioxo-1-(3-(trifluoromethyl)phenyl)-2,3,4,5,6,7-hexahydro-1H-cyclopenta[d]pyrimidin-4-yl)benzonitrile (example 9, 230 mg, 0.48 mmol) are separated by preparative supercritical fluid chromatography on a chiral phase (Daicel Chiralpak IB, 20×250 mm, 5 μm, 15% MeOH+0.2% diethylamine in supercritical $CO_2$, 40° C., 150 bar back pressure).

EXAMPLE 9A

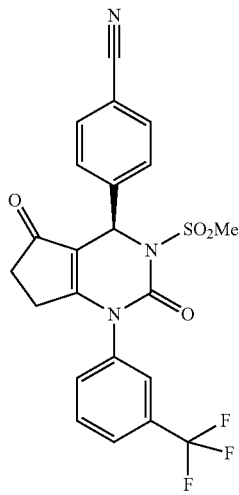

(R)-4-(3-(Methylsulfonyl)-2,5-dioxo-1-(3-(trifluoromethyl)phenyl)-2,3,4,5,6,7-hexahydro-1H-cyclopenta[d]pyrimidin-4-yl)benzonitrile Yield 65 mg; ESI mass spectrum $[M+H]^+$=476; Retention time: 2.25 min (early eluting enantiomer) (I_IB_15_MeOH_DEA).

EXAMPLE 9B

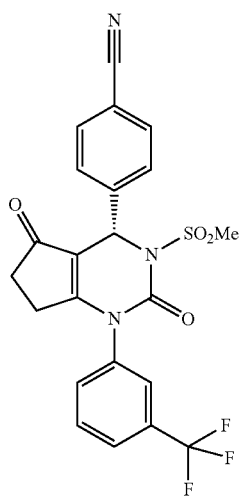

(S)-4-(3-(Methylsulfonyl)-2,5-dioxo-1-(3-(trifluoromethyl)phenyl)-2,3,4,5,6,7-hexahydro-1H-cyclopenta[d]pyrimidin-4-yl)benzonitrile Yield 71 mg; ESI mass spectrum [M+H]$^+$=476; Retention time: 3.04 min (late eluting enantiomer) (I_IB_15_MeOH_DEA).

EXAMPLE 10

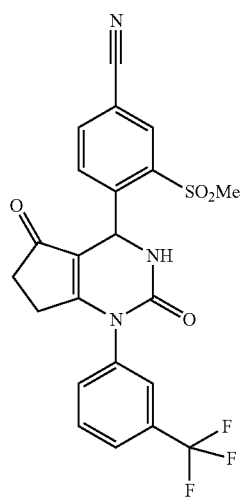

4-(2,5-Dioxo-1-(3-(trifluoromethyl)phenyl)-2,3,4,5,6,7-hexahydro-1H-cyclopenta[d]pyrimidin-4-yl)-3-(methylsulfonyl)benzonitrile Under an atmosphere of argon, a mixture of 4-(4-bromo-2-(methylsulfonyl)phenyl)-1-(3-(trifluoromethyl)phenyl)-3,4,6,7-tetrahydro-1H-cyclopenta[d]pyrimidine-2,5-dione (intermediate 8, 110 mg, 0.21 mmol), zinc cyanide (32 mg, 0.27 mmol) and tetrakis (triphenylphosphine)palladium(0) (24 mg, 21 µmol) in N,N-dimethylformamide (2 mL) is heated at 110° C. over night and then cooled to room temperature. Water is added and the mixture is filtered. The precipitate is purified by flash chromatography on silica (gradient cyclohexane/ethyl acetate 8:2 to 3:7). Yield: 40 mg; ESI mass spectrum: [M+H]$^+$=476; Retention time HPLC: 0.94 min (Z017_S04).

Examples 10A and 10B

Enantiomers of Example 10

The enantiomers of racemic 4-(2,5-dioxo-1-(3-(trifluoromethyl)phenyl)-2,3,4,5,6,7-hexahydro-1H-cyclopenta[d]pyrimidin-4-yl)-3-(methylsulfonyl)benzonitrile (example 10, 1.82 g, 3.83 mmol) are separated by preparative supercritical fluid chromatography on a chiral phase (Daicel Chiralpak IB, 20×250 mm, 5 µm, 15% MeOH+0.2% diethylamine in supercritical CO$_2$, 40° C., 120 bar back pressure).

EXAMPLE 10A

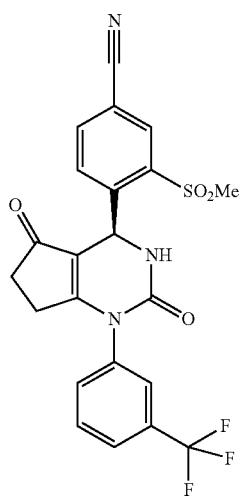

(S)-4-(2,5-Dioxo-1-(3-(trifluoromethyl)phenyl)-2,3,4,5,6,7-hexahydro-1H-cyclopenta[d]pyrimidin-4-yl)-3-(methylsulfonyl)benzonitrile Yield 620 mg; ESI mass spectrum [M+H]$^+$=476; Retention time: 2.52 min (early eluting enantiomer) (I_IB_20_MeOH_DEA).

EXAMPLE 10B

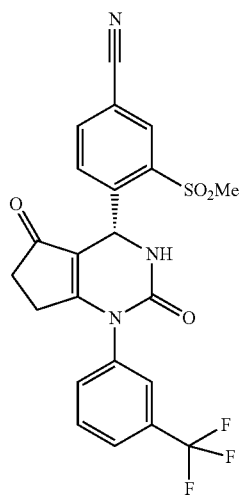

(R)-4-(2,5-Dioxo-1-(3-(trifluoromethyl)phenyl)-2,3,4,5,6,7-hexahydro-1H-cyclopenta[d]pyrimidin-4-yl)-3-(methylsulfonyl)benzonitrile Yield 554 mg; ESI mass spectrum [M+H]$^+$=476; Retention time: 2.78 min (late eluting enantiomer) (I_IB_20_MeOH_DEA).

EXAMPLE 11

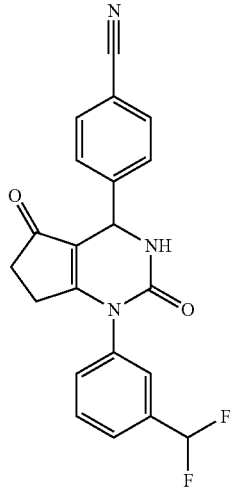

4-(1-(3-(Difluoromethyl)phenyl)-2,5-dioxo-2,3,4,5,6,7-hexahydro-1H-cyclopenta[d]-pyrimidin-4-yl)benzonitrile Under an atmosphere of argon, a mixture of 4-(4-bromophenyl)-1-(3-(difluoromethyl)-phenyl)-3,4,6,7-tetrahydro-1H-cyclopenta[d]pyrimidine-2,5-dione (intermediate 6, 159 mg, 367 µmol), zinc cyanide (73 mg, 620 µmol) and tetrakis(triphenylphosphine)palladium(0) (42 mg, 37 µmol) in N,N-dimethylformamide (2 mL) is heated at 110° C. for 3 h and then cooled to room temperature. Water is added and the mixture is extracted twice with dichloromethane. The residue is purified by flash chromatography on silica (gradient cyclohexane/ethyl acetate 7:3 to ethyl acetate). Yield: 82 mg; ESI mass spectrum: [M+H]$^+$=380; Retention time HPLC: 0.49 min (X012_S01).

EXAMPLE 12

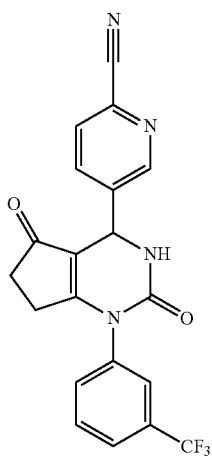

5-(2,5-Dioxo-1-(3-(trifluoromethyl)phenyl)-2,3,4,5,6,7-hexahydro-1H-cyclopenta[d]-pyrimidin-4-yl)picolinonitrile Under an atmosphere of argon, a mixture of 4-(6-chloro-pyridin-3-yl)-1-(3-(trifluoro-methyl)phenyl)-3,4,6,7-tetrahydro-1H-cyclopenta[d]pyrimidine-2,5-dione (intermediate 11, a) 120 mg, 294 µmol), zinc cyanide (59 mg, 0.50 mmol) and tetrakis(triphenylphosphine)-palladium(0) (34 mg, 29 µmol) in N,N-dimethylformamide (2 mL) is heated at 110° C. for 24 h. The reaction mixture is cooled to room temperature and then purified by preparative reversed phase HPLC (Waters Xbridge™-C$_{18}$, gradient of acetonitrile in water, 0.1% TFA). Yield: 10 mg; ESI mass spectrum [M+H]$^+$=399; Retention time HPLC: 0.50 min (V012_S01).

EXAMPLE 13

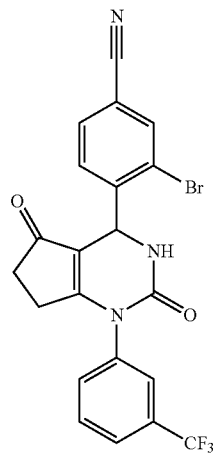

3-Bromo-4-(2,5-dioxo-1-(3-(trifluoromethyl)phenyl)-2,3,4,5,6,7-hexahydro-1H-cyclopenta[d]pyrimidin-4-yl)benzonitrile Triethylamine (0.43 mL, 3.0 mmol) is added to a mixture of 4-(amino(5-oxo-2-(3-(tri-fluoromethyl)phenylamino)cyclopent-1-enyl)methyl)-3-bromobenzonitrile hydrochloride (intermediate 20, 5.90 g, 12.1 mmol) and 1,1'-carbonyldiimidazole (2.46 g, 15.2 mmol) in acetonitrile (60 mL), and the mixture is stirred at room temperature over night. Water (700 mL) is added and the precipitate is filtered, washed with water and dried. Yield: 5.45 g. ESI a) mass spectrum: [($^{79}$Br)-M+H]$^+$=476, [($^{81}$Br)-M+H]$^+$=478; Retention time HPLC: 1.10 min (X011_S01).

EXAMPLE 14

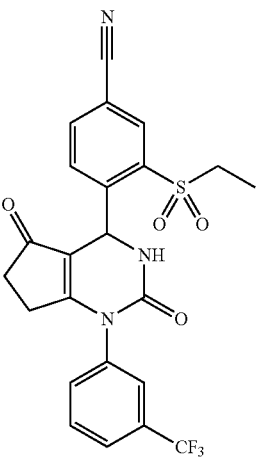

4-(2,5-Dioxo-1-(3-(trifluoromethyl)phenyl)-2,3,4,5,
6,7-hexahydro-1H-cyclopenta[d]pyrimidin-4-yl)-3-
(ethylsulfonyl)benzonitrile Triethylamine (125 µL, 0.89 mmol) is added to a mixture of 4-(amino(5-oxo-2-(3-(trifluoromethyl)phenylamino)cyclopent-1-enyl)methyl)-3-(ethylsulfonyl)benzonitrile hydrochloride (intermediate 20.2, 1.78 g, 3.56 mmol) and 1,1'-carbonyldiimidazole (720 mg, 4.45 mmol) in acetonitrile (20 mL), and the mixture is stirred at room temperature for 1 h. The mixture is concentrated under reduced pressure, and the residue is treated with water (20 mL). The precipitate is filtered and dried. Yield: 1.61 g. ESI mass spectrum: [M+H]$^+$=490; Retention time HPLC: 0.56 min (X012_801).

Examples 14A and 14B

Enantiomers of Example 14

The enantiomers of racemic 4-(2,5-dioxo-1-(3-(trifluoromethyl)phenyl)-2,3,4,5,6,7-hexahydro-1H-cyclopenta[d]pyrimidin-4-yl)-3-(ethylsulfonyl)benzonitrile (example 14, 48 mg, 98 µmol) are separated by preparative supercritical fluid chromatography on a chiral phase (Daicel Chiralpak IB, 20×250 mm, 5 µm, 20% MeOH+0.2% diethylamine in supercritical CO$_2$, 40° C., 150 bar back pressure).

EXAMPLE 14B

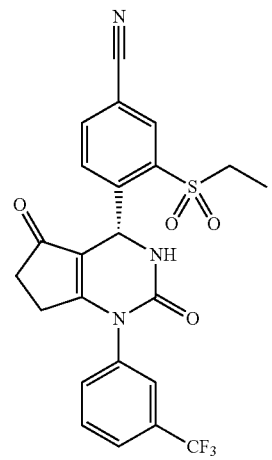

(R)-4-(2,5-Dioxo-1-(3-(trifluoromethyl)phenyl)-2,3,
4,5,6,7-hexahydro-1H-cyclopenta[d]pyrimidin-4-yl)-
3-(ethylsulfonyl)benzonitrile Yield: 16 mg; ESI mass spectrum [M+H]$^+$=490; Retention time: 2.82 min (late eluting enantiomer) (I_IB_20_MeOH_DEA).

EXAMPLE 14A

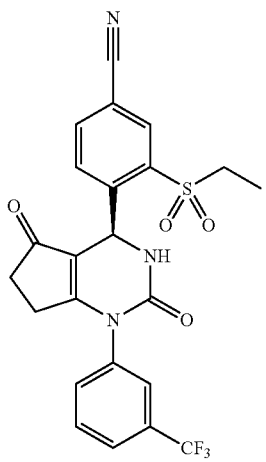

(S)-4-(2,5-Dioxo-1-(3-(trifluoromethyl)phenyl)-2,3,
4,5,6,7-hexahydro-1H-cyclopenta[d]pyrimidin-4-yl)-
3-(ethylsulfonyl)benzonitrile Yield: 16 mg; ESI mass spectrum [M+H]$^+$=490; Retention time: 2.28 min (early eluting enantiomer) (I_IB_20_MeOH_DEA).

EXAMPLE 15

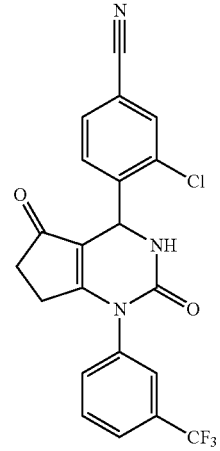

3-Chloro-4-(2,5-dioxo-1-(3-(trifluoromethyl)phenyl)-2,3,4,5,6,7-hexahydro-1H-cyclopenta[d]pyrimidin-4-yl)benzonitrile Triethylamine (0.38 mL, 2.70 mmol) is added to a mixture of 4-(amino(5-oxo-2-(3-(tri-fluoromethyl)phenylamino)cyclopent-1-enyl)methyl)-3-chlorobenzonitrile hydrochloride (intermediate 20.1, 660 mg, 1.34 mmol based on 90% purity) and 1,1'-carbonyldiimidazole (270 mg, 1.68 mmol) in acetonitrile (5 mL), and the mixture is stirred at room temperature over night. Water and dichloromethane are added, and the phases are separated. The organic layer is concentrated under reduced pressure and purified by reversed phase HPLC (Waters Xbridge™-C$_{18}$, gradient of acetonitrile in water, 0.1% TFA). Yield: 290 mg. ESI mass spectrum: [M+H]$^+$=432; Retention time HPLC: 0.61 min (X012_S01).

Examples 15.1-15.7

The following examples of Table 7 are prepared in analogy to 3-chloro-4-(2,5-dioxo-1-(3-(trifluoromethyl)phenyl)-2,3,4,5,6,7-hexahydro-1H-cyclopenta[d]pyrimidin-4-yl)benzonitrile (example 15), using the appropriate starting material and the purification method as indicated in the table (Method A: Waters Xbridge™-C$_{18}$, gradient of acetonitrile in water, 0.1% TFA; Method B: Waters SunFire™-C$_{18}$, gradient of acetonitrile in water, 0.1% TFA; Method C: Waters SunFire™-C$_{18}$, gradient of acetonitrile in water, 0.1% formic acid).

TABLE 7

| Example | Starting Material | Structure | Purification Method | MS [M + H]⁺ | Retention time [min] | HPLC-Method |
|---|---|---|---|---|---|---|
| 15.1 | intermediate 20.3 | 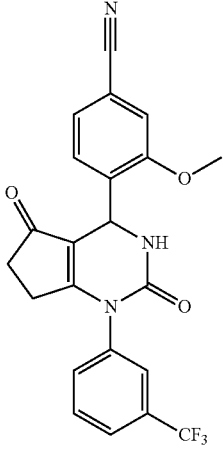 [SMILES: COc1cc(C#N)ccc1C1NC(=O)N(c2cccc(C(F)(F)F)c2)C2=C1C(=O)CC2] | A | 428 | 0.59 | X012_S01 |
| 15.2 | intermediate 20.4 | 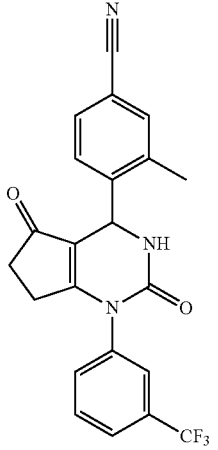 [SMILES: Cc1cc(C#N)ccc1C1NC(=O)N(c2cccc(C(F)(F)F)c2)C2=C1C(=O)CC2] | A | 412 | 0.60 | X012_S01 |
| 15.3 | intermediate 20.6 | 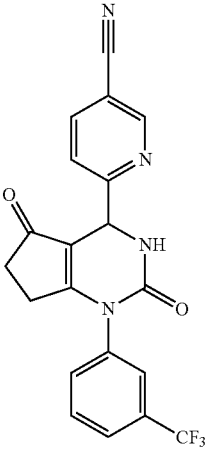 [SMILES: N#Cc1ccc(C2NC(=O)N(c3cccc(C(F)(F)F)c3)C3=C2C(=O)CC3)nc1] | B | 399 | 0.51 | X011_S03 |

TABLE 7-continued

| Example | Starting Material | Structure | Purification Method | MS [M + H]+ | Retention time [min] | HPLC- Method |
|---|---|---|---|---|---|---|
| 15.4 | intermediate 20.7 | 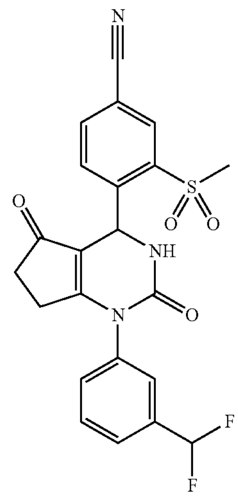 [SMILES: CS(=O)(=O)c1cc(C#N)ccc1C1NC(=O)N(c2cccc(C(F)F)c2)C2=C1C(=O)CC2] | B | 458 | 0.91 | Z018_S04 |
| 15.5 | intermediate 20.8 | 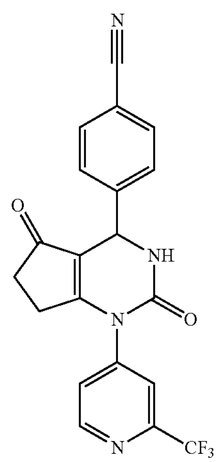 [SMILES: N#Cc1ccc(C2NC(=O)N(c3ccnc(C(F)(F)F)c3)C3=C2C(=O)CC3)cc1] | C | 399 | 0.91 | Z018_S04 |
| 15.6 | intermediate 20.9 | 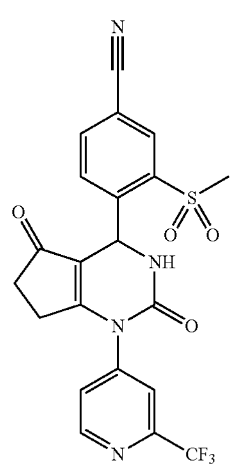 [SMILES: CS(=O)(=O)c1cc(C#N)ccc1C1NC(=O)N(c2ccnc(C(F)(F)F)c2)C2=C1C(=O)CC2] | B | 477 | 0.90 | Z018_S04 |

TABLE 7-continued

| Example | Starting Material | Structure | Purification Method | MS [M + H]+ | Retention time [min] | HPLC-Method |
|---|---|---|---|---|---|---|
| 15.7 | intermediate 24 | 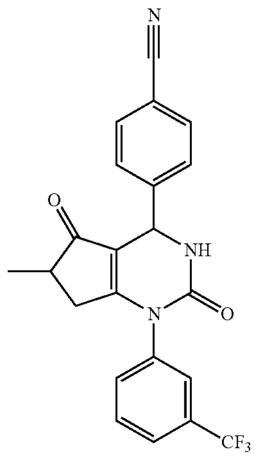 [SMILES: CC1CC2=C(C1=O)C(c1ccc(C#N)cc1)NC(=O)N2c1cccc(C(F)(F)F)c1] | A | 412 | 0.63 | X012_S01 |

Examples 15.3A and 15.3B

Enantiomers of Example 15.3

The enantiomers of racemic 6-(2,5-dioxo-1-(3-(trifluoromethyl)phenyl)-2,3,4,5,6,7-hexahydro-1H-cyclopenta[d]pyrimidin-4-yl)nicotinonitrile (example 15.3, 650 mg, 1.63 mmol) are separated by preparative supercritical fluid chromatography on a chiral phase (Daicel Chiralpak IB, 20×250 mm, 5 μm, 25% MeOH+0.2% diethylamine in supercritical $CO_2$, 40° C., 150 bar back pressure).

EXAMPLE 15.3A

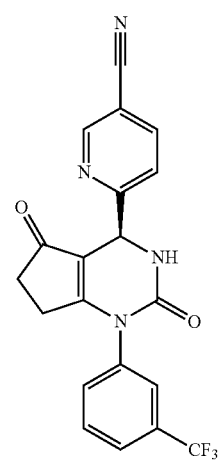

(S)-6-(2,5-Dioxo-1-(3-(trifluoromethyl)phenyl)-2,3,4,5,6,7-hexahydro-1H-cyclopenta[d]pyrimidin-4-yl)nicotinonitrile Yield: 140 mg; ESI mass spectrum [M+H]+=399; Retention time: 3.24 min (late eluting enantiomer) (I_IB_25_MeOH_NH3).

EXAMPLE 15.3B

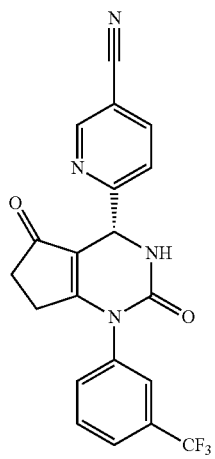

(R)-6-(2,5-Dioxo-1-(3-(trifluoromethyl)phenyl)-2,3,4,5,6,7-hexahydro-1H-cyclopenta[d]pyrimidin-4-yl)nicotinonitrile Yield: 130 mg; ESI mass spectrum [M+H]+=399; Retention time: 2.66 min (early eluting enantiomer) (I_IB_25_MeOH_NH3).

Examples 15.4A and 15.4B

Enantiomers of Example 15.4

The enantiomers of racemic 4-(1-(3-(difluoromethyl)phenyl)-2,5-dioxo-2,3,4,5,6,7-hexahydro-1H-cyclopenta[d]pyrimidin-4-yl)-3-(methylsulfonyl)benzonitrile (example 15.4, 27 mg, 59 μmol) are separated by preparative supercritical fluid chromatography on a chiral phase (Daicel Chiralpak IA, 20×250 mm, 5 μm, 30% MeOH+0.2% diethylamine in supercritical $CO_2$, 40° C., 120 bar back pressure).

EXAMPLE 15.4A

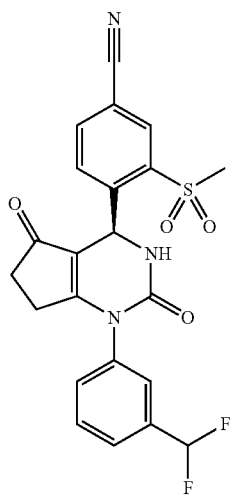

(S)-4-(1-(3-(Difluoromethyl)phenyl)-2,5-dioxo-2,3,
4,5,6,7-hexahydro-1H-cyclopenta[d]pyrimidin-4-yl)-
3-(methylsulfonyl)benzonitrile Yield: 10 mg; ESI mass spectrum [M+H]$^+$=458; Retention time: 2.37 min (early eluting enantiomer) (I_IA_30_MeOH_NH3).

EXAMPLE 15.4B

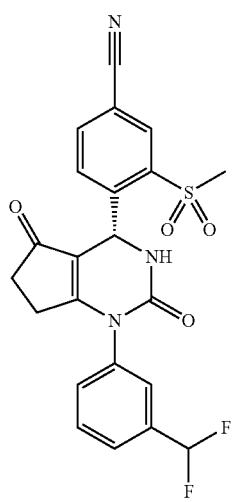

(R)-4-(1-(3-(Difluoromethyl)phenyl)-2,5-dioxo-2,3,
4,5,6,7-hexahydro-1H-cyclopenta[d]pyrimidin-4-yl)-
3-(methylsulfonyl)benzonitrile Yield: 10 mg; ESI mass spectrum [M+H]$^+$=458; Retention time: 3.00 min (late eluting enantiomer) (I_IA_30_MeOH_NH3).

EXAMPLE 16

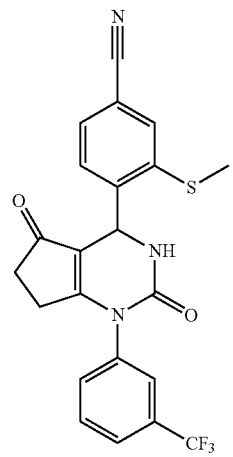

4-(2,5-Dioxo-1-(3-(trifluoromethyl)phenyl)-2,3,4,5,
6,7-hexahydro-1H-cyclopenta[d]-pyrimidin-4-yl)-3-
(methylthio)benzonitrile Under an atmosphere of argon, a mixture of 4-(4-bromo-2-(methylthio)phenyl)-1-(3-(trifluoromethyl)phenyl)-3,4,6,7-tetrahydro-1H-cyclopenta[d]pyrimidine-2,5-dione (intermediate 25, 1.74 g, 2.8 mmol based on 80% purity), zinc cyanide (430 mg, 3.64 mmol) and tetrakis (triphenylphosphine)palladium(0) (323 mg, 0.28 mmol) in N,N-dimethylformamide (12 mL) is heated at 110° C. over night and then cooled to room temperature. Water is added, and the mixture is extracted with dichloromethane. The organic layer is concentrated under reduced pressure, and the residue is purified by reversed phase HPLC (Waters Xbridge™-C$_{18}$, gradient of acetonitrile in water, 0.1% NH$_3$). Yield: 1.09 g. ESI mass spectrum: [M+H]$^+$=444; Retention time HPLC: 0.58 min (X011_S03).

EXAMPLE 17

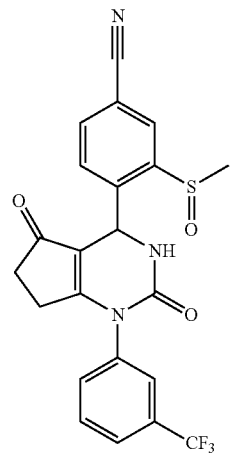

4-(2,5-Dioxo-1-(3-(trifluoromethyl)phenyl)-2,3,4,5,
6,7-hexahydro-1H-cyclopenta[d]-pyrimidin-4-yl)-3-
(methylsulfinyl)benzonitrile meta-Chloroperoxybenzoic acid (77%, 390 mg, 1.74 mmol) is added at room temperature to a solution of 4-(2,5-dioxo-1-(3-(trifluoromethyl)phenyl)-2,3,4,5,6,7-hexahydro-1H-cyclopenta[d]pyrimidin-4-yl)-3-(methylthio)benzonitrile (example 16, 776 mg, 1.75 mmol) in dichloromethane, and the mixture is stirred for 30 min Saturated aqueous NaHCO$_3$ solution is added, and the mixture is extracted with dichloromethane. The combined organic layers are concentrated under reduced pressure, and the residue is purified by flash chromatography on silica (gradient cyclohexane/ethyl acetate 1:1 to ethyl acetate. Yield: 527 mg; ESI mass spectrum [M+H]$^+$=460; Retention time HPLC: 0.48 min (early eluting diastereomer), 0.49 (late eluting diastereomer) (X012_S01).

Examples 17A and 17B

Diastereomers of Example 17

The diastereomers of 4-(2,5-dioxo-1-(3-(trifluoromethyl)phenyl)-2,3,4,5,6,7-hexahydro-1H-cyclopenta[d]pyrimidin-4-yl)-3-(methylsulfinyl)benzonitrile (example 17, 35 mg) are separated by reversed phase HPLC (Waters Xbridge™-C$_{18}$, gradient of acetonitrile in water, 0.1% TFA).

Example 17A

Yield: 11 mg; ESI mass spectrum [M+H]$^+$=460; Retention time HPLC: 0.48 min (early eluting diastereomer) (X012_S01).

Example 17B

Yield: 7 mg; ESI mass spectrum [M+H]$^+$=460; Retention time HPLC: 0.50 min (late eluting diastereomer) (X012_S01).

EXAMPLE 18

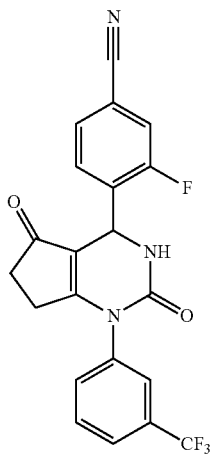

4-(2,5-Dioxo-1-(3-(trifluoromethyl)phenyl)-2,3,4,5,6,7-hexahydro-1H-cyclopenta[d]-pyrimidin-4-yl)-3-fluorobenzonitrile Step 1:
4-(Chloro(isocyanato)methyl)-3-fluorobenzonitrile Phosphorous pentachloride (9.63 g, 46.2 mmol) is added to a mixture of diethyl (4-cyano-2-fluorophenyl)methylenedicarbamate (intermediate 26, 6.50 g, 21.0 mmol) in toluene (25.0 mL), and the mixture is heated at reflux for 3 h. The toluene is evaporated, and the mixture is then purified by distillation under reduced pressure. The first fraction (ca. 35° C., ca. 0.2 mbar) is discarded. The second fraction (ca. 112° C., ca. 0.1 mbar) is collected. Yield: 1.90 g.

Step 2: 4-(2,5-Dioxo-1-(3-(trifluoromethyl)phenyl)-2,3,4,5,6,7-hexahydro-1H-cyclopenta[d]-pyrimidin-4-yl)-3-fluorobenzonitrile A solution of 4-(chloro(isocyanato)methyl)-3-fluorobenzonitrile (Step 1, 3.05 g, 14.5 mmol) in dichloromethane (10 mL) is added to a solution of 3-(3-(trifluoromethyl)-phenylamino)cyclopent-2-enone (3.50 g, 14.5 mmol) in dichloromethane (10 mL), and the mixture is heated at reflux over night. All volatiles are removed under reduced pressure, and the residue is purified by reversed phase HPLC (Agilent ZORBAX™ SB-C$_{18}$, gradient of acetonitrile in water, 0.1% formic acid). Yield: 474 mg; ESI mass spectrum [M+H]$^+$=416; Retention time HPLC: 0.94 min (Z017_504). LB5FAI00917

EXAMPLE 19

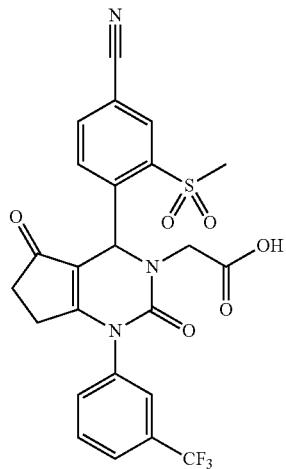

2-(4-(4-Cyano-2-(methylsulfonyl)phenyl)-2,5-dioxo-1-(3-(trifluoromethyl)phenyl)-6,7-dihydro-1H-cyclopenta[d]pyrimidin-3(2H,4H,5H)-yl)acetic acid Aqueous sodium hydroxide solution (1.0 M, 10.0 mL, 10.0 mmol) is added to a solution of ethyl 2-(4-(4-cyano-2-(methylsulfonyl)phenyl)-2,5-dioxo-1-(3-(trifluoromethyl)phenyl)-6,7-dihydro-1H-cyclopenta[d]pyrimidin-3(2H,4H,5H)-yl)acetate (intermediate 29, 1.80 g, 3.20 mmol) in tetrahydrofuran (40 mL), and the mixture is stirred at room temperature over night. Another portion of aqueous sodium hydroxide solution (4.0 M, 2.0 mL, 8.0 mmol) and methanol (5.0 mL) is added, and mixture is stirred over night. Aqueous hydrogen chloride (1.0 M, 10 mL) is added, and the mixture is extracted with ethyl acetate. The organic layer is concentrated under reduced pressure, and the residue is purified reversed phase HPLC (Waters SunFire™-C$_{18}$, gradient of acetonitrile in water, 0.1% TFA). Yield: 229 mg; ESI mass spectrum: [M+H]$^+$=534; Retention time HPLC: 0.96 min (Z018_S04).

EXAMPLE 20

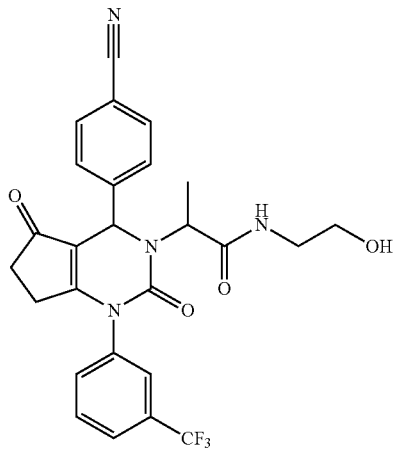

2-(4-(4-Cyanophenyl)-2,5-dioxo-1-(3-(trifluoromethyl)phenyl)-6,7-dihydro-1H-cyclopenta[d]pyrimidin-3(2H,4H,5H)-yl)-N-(2-hydroxyethyl)propanamide A solution of 2-(4-(4-cyanophenyl)-2,5-dioxo-1-(3-(trifluoromethyl)phenyl)-6,7-dihydro-1H-cyclopenta[d]pyrimidin-3(2H,4H,5H)-yl)propanoic acid (intermediate 28, 40 mg, 85 μmol) and triethylamine (45 μL, 0.32 mmol) in N,N-dimethylformamide (1.5 mL) is treated with N,N,N',N'-tetramethyl-O-(benzotriazol-1-yl)uronium tetrafluoroborate (27 mg, 85 μmol) and stirred at room temperature for 15 min. Ethanolamine (12 μL, 0.21 mmol) is added and the mixture is stirred at room temperature for 1 h. The mixture is diluted with N,N-dimethylformamide and purified by reversed phase HPLC (Waters SunFire™-$C_{18}$, gradient of acetonitrile in water, 0.1% TFA). Yield: 37 mg; ESI mass spectrum [M+H]$^+$=513; Retention time HPLC: 0.81 min (Z018_S04).

EXAMPLE 21

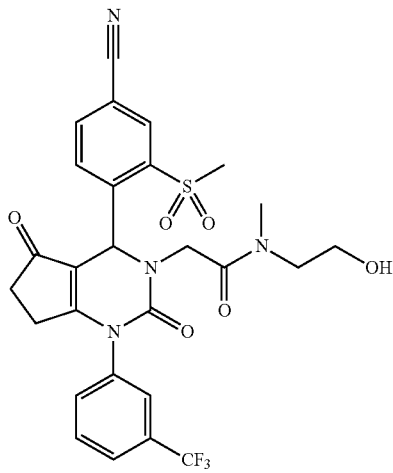

2-(4-(4-Cyano-2-(methylsulfonyl)phenyl)-2,5-dioxo-1-(3-(trifluoromethyl)phenyl)-6,7-dihydro-1H-cyclopenta[d]pyrimidin-3(2H,4H,5H)-yl)-N-(2-hydroxyethyl)-N-methyl-acetamide A solution of 2-(4-(4-cyano-2-(methylsulfonyl)phenyl)-2,5-dioxo-1-(3-(trifluoromethyl)-phenyl)-6,7-dihydro-1H-cyclopenta[d]pyrimidin-3(2H,4H,5H)-yl)acetic acid (example 19, 23 mg, 43 μmol) and triethylamine (18 μL, 0.13 mmol) in N,N-dimethylformamide (1.0 mL) is stirred at room temperature for 5 min and treated with N,N,N',N'-tetramethyl-0-(benzotriazol-1-yl)uronium tetrafluoroborate (13 mg, 43 μmol). After 5 min, 2-(methyl-amino)ethanol (10 μL, 0.13 mmol) is added. The mixture is stirred at room temperature for 3 h and purified by reversed phase HPLC (Waters Xbridge™-$C_{18}$, gradient of acetonitrile in water, 0.1% $NH_3$). Yield: 15 mg; ESI mass spectrum [M+H]$^+$=591; Retention time HPLC: 0.89 min (Z011_S03).

Examples 22.1-22.9

The following examples of Table 8 are prepared in analogy to 2-(4-(4-cyano-2-(methyl-sulfonyl)phenyl)-2,5-dioxo-1-(3-(trifluoromethyl)phenyl)-6,7-dihydro-1H-cyclopenta[d]-pyrimidin-3(2H,4H,5H)-yl)-N-(2-hydroxyethyl)-N-methylacetamid (example 21), using the appropriate amine as reagent.

TABLE 8

| Example | R$^3$ | MS [M + H]$^+$ | Retention time [min] | HPLC-Method |
|---------|-------|----------------|----------------------|-------------|
| 22.1    |       | 561            | 0.81                 | 005_CA01    |

TABLE 8-continued
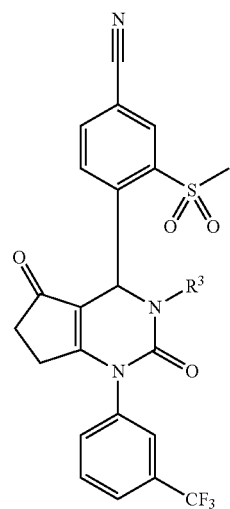
| Example | R³ | MS [M + H]⁺ | Retention time [min] | HPLC-Method |
|---|---|---|---|---|
| 22.2 | azetidine-CO-CH(···)- | 573 | 0.81 | 005_CA01 |
| 22.3 | pyrrolidine-CO-CH(···)- | 587 | 0.84 | 005_CA01 |
| 22.4 | 3-azabicyclo[3.1.0]hexane-CO-CH(···)- | 599 | 0.87 | 005_CA01 |
| 22.5 | morpholine-CO-CH(···)- | 603 | 0.80 | 005_CA01 |
| 22.6 | N(Me)(CH₂CH₂OMe)-CO-CH(···)- | 605 | 0.83 | 005_CA01 |
| 22.7 | 3-fluoropyrrolidine-CO-CH(···)- | 605 | 0.82 | 005_CA01 |

TABLE 8-continued

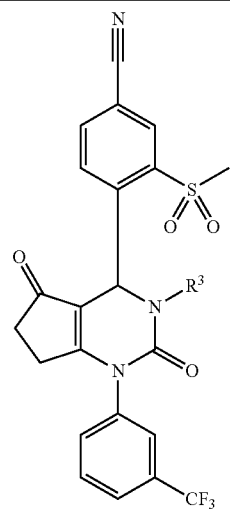

| Example | R³ | MS [M + H]⁺ | Retention time [min] | HPLC-Method |
|---|---|---|---|---|
| 22.8 | ...piperidine-OMe | 631 | 0.85 | 005_CA01 |
| 22.9 | ...N-methyl-N-((1-methyl-1H-pyrazol-4-yl)methyl)amide | 641 | 0.79 | 005_CA01 |

EXAMPLE 22

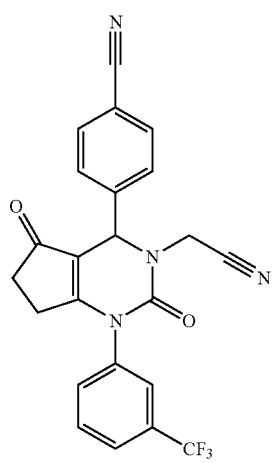

4-(3-(Cyanomethyl)-2,5-dioxo-1-(3-(trifluoromethyl)phenyl)-2,3,4,5,6,7-hexahydro-1H-cyclopenta[d]pyrimidin-4-yl)benzonitrile Sodium hydride (60% in mineral oil, 11 mg, 0.29 mmol) is added to a solution of 4-(2,5-dioxo-1-(3-(trifluoro-methyl)phenyl)-2,3,4,5,6,7-hexahydro-1H-cyclopenta[d]-pyrimidin-4-yl)benzonitrile (example 1, 40 mg, 96 μmol) in acetonitrile (3.0 mL). After 20 min, 2-iodoacetonitrile (7 μL, 0.1 mmol) is added. The mixture is stirred at room temperature over night and purified by reversed phase HPLC (Waters Xbridge™-C$_{18}$, gradient of acetonitrile in water, 0.1% TFA). Yield: 11 mg; ESI mass spectrum [M+H]⁺=437; Retention time HPLC: 0.63 min (X012_S01).

EXAMPLE 23

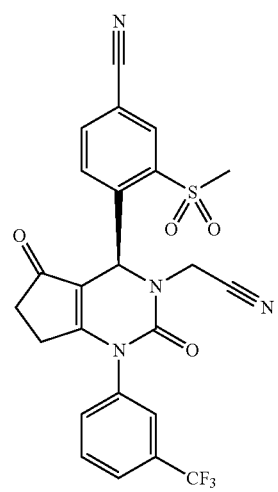

121

(S)-4-(3-(Cyanomethyl)-2,5-dioxo-1-(3-(trifluoromethyl)phenyl)-2,3,4,5,6,7-hexahydro-1H-cyclopenta[d]pyrimidin-4-yl)-3-(methylsulfonyl)benzonitrile Sodium hydride (60% in mineral oil, 12 mg, 0.30 mmol) is added to a solution of (S)-4-(2,5-dioxo-1-(3-(trifluoromethyl)phenyl)-2,3,4,5,6,7-hexahydro-1H-cyclopenta[d]-pyrimidin-4-yl)-3-(methylsulfonyl)benzonitrile (example 10A, 50 mg, 105 µmol) in tetrahydrofuran (3.0 mL). After 20 min, 2-iodoacetonitrile (8 µL, 0.11 mmol) is added. After 2 h, a second portion of 2-iodoacetonitrile (8 µL, 0.11 mmol) is added. After 2 h, a third portion of 2-iodoacetonitrile (8 µL, 0.11 mmol) is added. The mixture is stirred over night, treated with acetonitrile and purified by reversed phase HPLC (Waters SunFire™-$C_{18}$, gradient of acetonitrile in water, 0.1% TFA). Yield: 8 mg; ESI mass spectrum [M+H]$^+$=515; Retention time HPLC: 1.01 min (Z018_504).

122

4-(3-Ethyl-2,5-dioxo-1-(3-(trifluoromethyl)phenyl)-2,3,4,5,6,7-hexahydro-1H-cyclopenta[d]pyrimidin-4-yl)-3-(methylsulfonyl)benzonitrile Bromoethane (20 µL, 0.27 mmol) is added to a solution of 4-(2,5-dioxo-1-(3-(trifluoro-methyl)phenyl)-2,3,4,5,6,7-hexahydro-1H-cyclopenta[d]pyrimidin-4-yl)-3-(methyl-sulfonyl)benzonitrile (example 10, 60 mg, 0.11 mmol based on 90% purity) and cesium carbonate (74 mg, 0.23 mmol) in N,N-dimethylformamide (2.0 mL). The mixture is stirred at room temperature over night and purified by reversed phase HPLC (Waters SunFire™-$C_{18}$, gradient of acetonitrile in water, 0.1% TFA). Yield: 23 mg; ESI mass spectrum [M+H]$^+$=504; Retention time HPLC: 0.86 min (005_CA01).

Examples 24.1-24.6

The following examples of Table 9 are prepared in analogy to 4-(3-ethyl-2,5-dioxo-1-(3-(trifluoromethyl)phenyl)-2,3,4,5,6,7-hexahydro-1H-cyclopenta[d]pyrimidin-4-yl)-3-(methylsulfonyl)benzonitrile (example 24), substituting bromoethane with the appropriate alkylating reagent and using the purification method indicated in the table (Method A: Waters SunFire™-$C_{18}$, gradient of acetonitrile in water, 0.1% TFA; Method B: Waters Xbridge™-$C_{18}$, gradient of acetonitrile in water, 0.1% NH$_3$; Method C: Waters Xbridge™-Phenyl, gradient of methanol in water, 0.1% TFA).

EXAMPLE 24

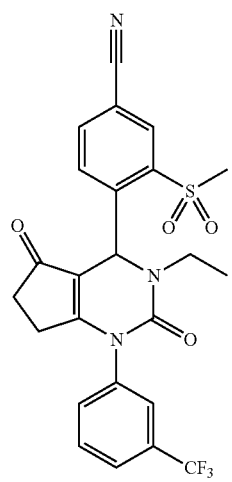

TABLE 9

| Example | R$^3$ | Purification Method | MS [M + H]$^+$ | Retention time [min] | HPLC-Method |
|---|---|---|---|---|---|
| 24.1 | ⸺∕∖∕OH | C | 534 | 0.97 | Z018_S04 |

TABLE 9-continued
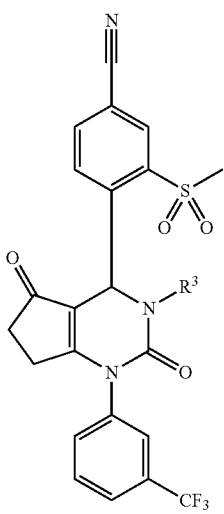
| Example | R³ | Purification Method | MS [M + H]⁺ | Retention time [min] | HPLC-Method |
|---|---|---|---|---|---|
| 24.2 | ⟋⟍O⟋ | A | 534 | 0.84 | 005_CA01 |
| 24.3 | ⟋⟍CHF₂ | A | 540 | 1.07 | Z018_S04 |
| 24.4 | ⟋⟍⟋O⟋ | A | 548 | 0.86 | 005_CA01 |
| 24.5 | ⟋-tetrahydropyran-4-yl | A | 574 | 1.05 | Z018_S04 |
| 24.6 | ⟋⟍-tetrahydropyran-4-yl | B | 588 | 0.87 | 003_CA04 |

EXAMPLE 25

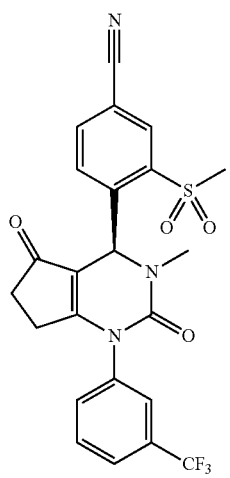

(S)-4-(3-Methyl-2,5-dioxo-1-(3-(trifluoromethyl)
phenyl)-2,3,4,5,6,7-hexahydro-1H-cyclopenta[d]
pyrimidin-4-yl)-3-(methylsulfonyl)benzonitrile A solution of (S)-4-(2,5-dioxo-1-(3-(trifluoromethyl)phenyl)-2,3,4,5,6,7-hexahydro-1H-cyclopenta[d]pyrimidin-4-yl)-3-(methylsulfonyl)benzonitrile (example 10A, 50 mg, 0.11 mmol) in N,N-dimethylformamide (1.0 mL) is treated with lithium diisopropylamide (1.8 M in tetrahydrofuran/heptane/ethylbenzene, 63 µL, 0.12 mmol) and methyl iodide (9 µL, 0.14 mmol). After 20 min the mixture is diluted with acetonitrile and purified by reversed phase HPLC (Agilent ZORBAX™ SB-$C_{18}$, gradient of acetonitrile in water, 0.1% formic acid). Yield: 15 mg; ESI mass spectrum [M+H]$^+$=490; Retention time HPLC: 1.00 min (Z017_S04).

EXAMPLE 26

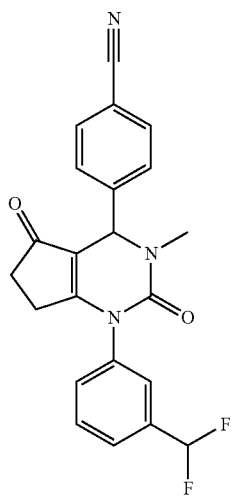

4-(1-(3-(Difluoromethyl)phenyl)-3-methyl-2,5-dioxo-2,3,4,5,6,7-hexahydro-1H-cyclopenta[d]pyrimidin-4-yl)benzonitrile Sodium hydride (60% in mineral oil, 13 mg, 0.32 mmol) is added to a solution of 4-(1-(3-(difluoromethyl)phenyl)-2,5-dioxo-2,3,4,5,6,7-hexahydro-1H-cyclopenta[d]-pyrimidin-4-yl)benzonitrile (example 11, 100 mg, 0.26 mmol) in tetrahydrofuran. After 20 min methyl iodide (22 µL, 0.35 mmol) is added and the mixture is stirred at room temperature over night. Water is added and the mixture is purified by reversed phase HPLC (Waters SunFire™-$C_{18}$, gradient of acetonitrile in water, 0.1% TFA). Yield: 55 mg; ESI mass spectrum [M+H]$^+$=394; Retention time HPLC: 0.74 min (005_CA01).

Examples 26A and 26B

Enantiomers of Example 26

The enantiomers of racemic 4-(1-(3-(difluoromethyl)phenyl)-3-methyl-2,5-dioxo-2,3,4,5,6,7-hexahydro-1H-cyclopenta[d]pyrimidin-4-yl)benzonitrile (example 26, 50 mg, 0.13 mmol) are separated by preparative supercritical fluid chromatography on a chiral phase (Daicel Chiralpak IA, 20×250 mm, 5 µm, 20% MeOH+20 mM $NH_3$ in supercritical $CO_2$, 40° C., 150 bar back pressure).

EXAMPLE 26A

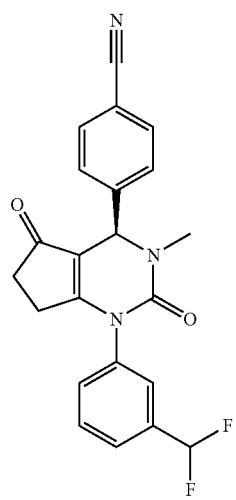

(R)-4-(1-(3-(Difluoromethyl)phenyl)-3-methyl-2,5-dioxo-2,3,4,5,6,7-hexahydro-1H-cyclopenta[d]pyrimidin-4-yl)benzonitrile Yield 23 mg; ESI mass spectrum [M+H]$^+$=394; Retention time: 2.03 min (early eluting enantiomer) (I_IA_20_MeOH_NH3).

EXAMPLE 26B

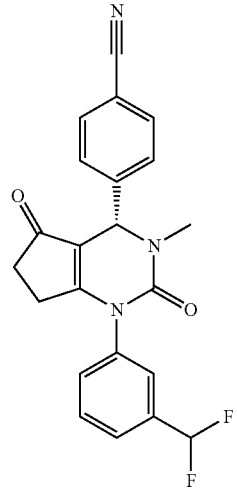

(S)-4-(1-(3-(Difluoromethyl)phenyl)-3-methyl-2,5-dioxo-2,3,4,5,6,7-hexahydro-1H-cyclopenta[d]pyrimidin-4-yl)benzonitrile Yield 23 mg; ESI mass spectrum [M+H]⁺=394; Retention time: 2.62 mM (late eluting enantiomer) (I_IA_20_MeOH_NH3).

Examples 26.1-26.4

The following examples of Table 10 are prepared in analog to 4-(1-(3-(difluoromethyl)-phenyl)-3-methyl-2,5-dioxo-2,3,4,5,6,7-hexahydro-1H-cyclopenta[d]pyrimidin-4-yl)-benzonitrile (example 26), using the appropriate starting material as indicated in the table and substituting tetrahydrofuran with acetonitrile as solvent.

TABLE 10

| Example | Starting Material | R¹ | MS [M + H]⁺ | Retention time [min] | HPLC-Method |
|---|---|---|---|---|---|
| 26.1 | example 15.3 | (5-cyanopyridin-2-yl) | 413 | 0.58 | X011_S03 |
| 26.2 | example 15.2 | (4-cyano-2-methylphenyl) | 426 | 0.61 | X012_S01 |
| 26.3 | example 15.1 | (4-cyano-2-methoxyphenyl) | 442 | 0.64 | X012_S01 |
| 26.4 | example 15 | (3-cyano-5-chlorophenyl) | 446 | 0.61 | X012_S01 |

EXAMPLE 27

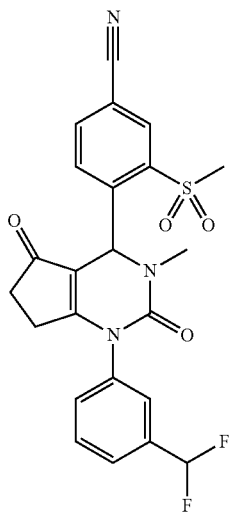

4-(1-(3-(Difluoromethyl)phenyl)-3-methyl-2,5-dioxo-2,3,4,5,6,7-hexahydro-1H-cyclopenta[d]pyrimidin-4-yl)-3-(methylsulfonyl)benzonitrile Methyl iodide (15 µL, 0.24 mmol) is added to a solution of 4-(1-(3-(difluoromethyl)-phenyl)-2,5-dioxo-2,3,4,5,6,7-hexahydro-1H-cyclopenta[d]pyrimidin-4-yl)-3-(methyl-sulfonyl)benzonitrile (example 15.4, 69 mg, 0.15 mmol) and cesium carbonate (98 mg, 0.30 mmol) in N,N-dimethylformamide (1.0 mL). The mixture is stirred at room temperature for 1 h and purified by reversed phase HPLC (Waters SunFire™-C₁₈, gradient of acetonitrile in water, 0.1% TFA). Yield: 19 mg; ESI mass spectrum [M+H]⁺=472; Retention time HPLC: 0.97 min (Z018_S04).

Examples 27.1-27.3

The following examples of Table 11 are prepared in analog to 4-(1-(3-(difluoromethyl)-phenyl)-3-methyl-2,5-dioxo-2,3,4,5,6,7-hexahydro-1H-cyclopenta[d]pyrimidin-4-yl)-3-(methylsulfonyl)benzonitrile (example 27), using the appropriate starting material as indicated in the table.

TABLE 11

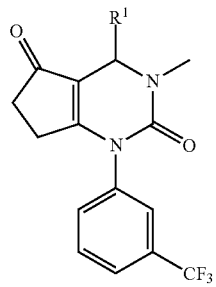

| Example | Starting Material | R¹ | MS [M+H]⁺ | Retention time [min] | HPLC-Method |
|---|---|---|---|---|---|
| 27.1 | example 16 | (CN-phenyl-SMe) | 458 | 1.04 | Z017_S04 |
| 27.2 | example 13 | (CN-phenyl-Br) | 490, 492 | 1.18 | V011_S01 |
| 27.3 | example 14 | (CN-phenyl-SO₂Et) | 504 | 0.62 | X012_S01 |

EXAMPLE 28

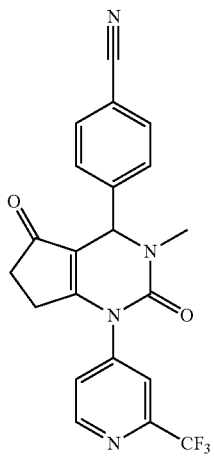

4-(3-Methyl-2,5-dioxo-1-(2-(trifluoromethyl)pyridin-4-yl)-2,3,4,5,6,7-hexahydro-1H-cyclopenta[d]pyrimidin-4-yl)benzonitrile Cesium carbonate (82 mg, 0.25 mmol) is added to a solution of 4-(2,5-Dioxo-1-(2-(tri-fluoromethyl)pyridin-4-yl)-2,3,4,5,6,7-hexahydro-1H-cyclopenta[d]pyrimidin-4-yl)benzonitrile (example 15.5, 50 mg, 0.13 mmol) in N,N-dimethylformamide (1.0 mL). Methyl iodide (28 mg, 0.20 mmol) is added, and the mixture is stirred at room temperature for 1 h and purified by reversed phase HPLC (Waters SunFire™-C₁₈, gradient of acetonitrile in water, 0.1% TFA). Yield: 43 mg; ESI mass spectrum [M+H]⁺=413; Retention time HPLC: 0.78 min (005_CA01).

EXAMPLE 29

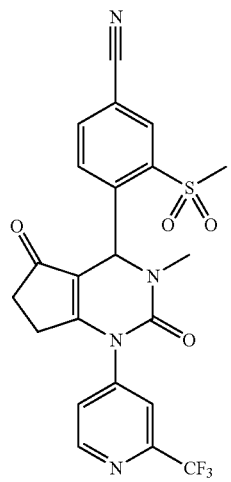

4-(3-Methyl-2,5-dioxo-1-(2-(trifluoromethyl)pyridin-4-yl)-2,3,4,5,6,7-hexahydro-1H-cyclopenta[d]pyrimidin-4-yl)-3-(methylsulfonyl)benzonitrile Methyl iodide (2 M in tert-butyl methyl ether, 63 µL, 0.13 mmol) is added to a solution of 4-(2,5-dioxo-1-(2-(trifluoromethyl)pyridin-4-yl)-2,3,4,5,6,7-hexahydro-1H-cyclopenta[d]-pyrimidin-4-yl)-3-(methylsulfonyl)benzonitrile (example 15.6, 50 mg, 0.11 mmol) and cesium carbonate (68 mg, 0.21 mmol) in N,N-dimethylformamide (2.0 mL), and the mixture is stirred at room temperature overnight. Water is added and the mixture is purified by reversed phase HPLC (Waters SunFire™-C₁₈, gradient of acetonitrile in water, 0.1% TFA). Yield: 39 mg; ESI mass spectrum [M+H]⁺=491; Retention time HPLC: 0.97 min (Z018_S04).

EXAMPLES 30A AND 30B: DIASTEREOMERS OF EXAMPLE 30

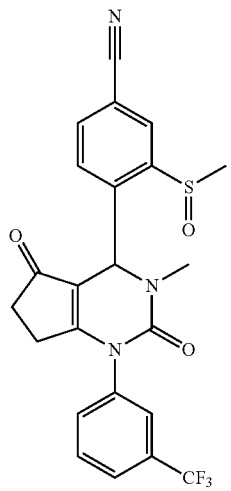

4-(3-Methyl-2,5-dioxo-1-(3-(trifluoromethyl)phenyl)-2,3,4,5,6,7-hexahydro-1H-cyclopenta[d]pyrimidin-4-yl)-3-(methylsulfinyl)benzonitrile A solution of 4-(3-methyl-2,5-dioxo-1-(3-(trifluoromethyl)phenyl)-2,3,4,5,6,7-hexahydro-1H-cyclopenta[d]pyrimidin-4-yl)-3-(methylthio)benzonitrile (example 27.1, 20 mg, 0.04 mmol) in dichloromethane (3.0 mL) is treated with meta-chloroperoxybenzoic acid (77%, 10 mg, 0.04 mmol), and the mixture is stirred at room temperature for 20 min. All volatiles are removed under reduced pressure, and the residue is purified by reversed phase HPLC (Waters SunFire™-C$_{18}$, gradient of acetonitrile in water, 0.1% TFA), whereupon the two diastereomers of 4-(3-methyl-2,5-dioxo-1-(3-(trifluoromethyl)phenyl)-2,3,4,5,6,7-hexahydro-1H-cyclopenta[d]pyrimidin-4-yl)-3-(methylsulfinyl)benzonitrile are separated.

Example 30A

Yield: 9 mg; ESI mass spectrum [M+H]$^+$=474; Retention time HPLC: 0.94 min (early eluting diastereomer) (Z018_S04).

Example 30B

Yield: 8 mg; ESI mass spectrum [M+H]$^+$=474; Retention time HPLC: 0.96 min (late eluting diastereomer) (Z018_S04).

EXAMPLE 31

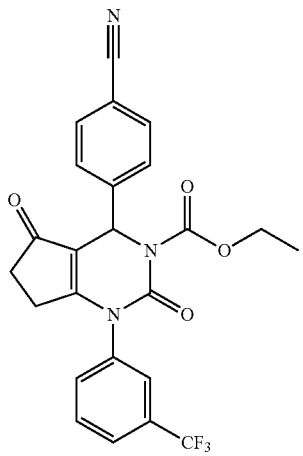

Ethyl 4-(4-Cyanophenyl)-2,5-dioxo-1-(3-(trifluoromethyl)phenyl)-4,5,6,7-tetrahydro-1H-cyclopenta[d]pyrimidine-3(2H)-carboxylate A solution of 4-(2,5-dioxo-1-(3-(trifluoromethyl)phenyl)-2,3,4,5,6,7-hexahydro-1H-cyclopenta[d]pyrimidin-4-yl)benzonitrile (example 1, 40 mg, 0.10 mmol) in dichloromethane (1.0 mL) is treated with N,N-diisopropylethylamine (70 µL, 0.4 mmol) and 4-dimethylaminopyridine (13 mg, 0.11 mmol). Ethyl chloroformate (11 µL, 0.11 mmol) is added and the mixture is stirred at room temperature for 2 h. All volatiles are evaporated pi and the residue is purified by reversed phase HPLC (Waters Xbridge™-C$_{18}$, gradient of acetonitrile in water, 0.1% NH$_3$). Yield: 46 mg; ESI mass spectrum [M+H]$^+$=470; Retention time HPLC: 0.90 min (Z011_S03).

Examples 31.1-31.3

The following compounds of Table 12 are prepared in analogy to ethyl 4-(4-cyanophenyl)-2,5-dioxo-1-(3-(trifluoromethyl)phenyl)-4,5,6,7-tetrahydro-1H-cyclopenta[d]pyrimidine-3(2H)-carboxylate (example 31), replacing ethyl chloroformate with the appropriate chloroformate.

TABLE 12

| Example | R$^3$ | MS [M + H]$^+$ | Retention time [min] | HPLC-Method |
|---|---|---|---|---|
| 31.1 | (propyl carbonate) | 484 | 0.94 | Z011_S03 |
| 31.2 | (2-methoxyethyl carbonate) | 500 | 0.88 | Z011_S03 |
| 31.3 | (2-(methylsulfonyl)ethyl carbonate) | 548 | 0.87 | Z018_S04 |

Examples 32.1-32.4

The following compounds of Table 13 are prepared in analog to methyl 4-(4-cyanophenyl)-2,5-dioxo-1-(3-(trifluoromethyl)phenyl)-4,5,6,7-tetrahydro-1H-cyclopenta[d]pyrimidine-3(2H)-carboxylate (example 8), replacing methyl chloroformate with the appropriate chloroformate as reagent.

TABLE 13

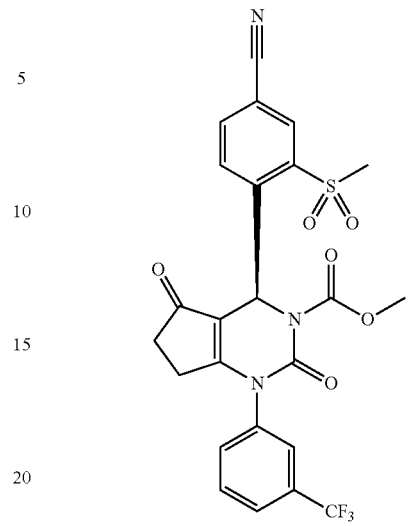

| Example | R³ | MS [M + H]⁺ | Retention time [min] | HPLC-Method |
|---|---|---|---|---|
| 32.1 | ![](methyl ester) | 534 | 0.59 | X011_S03 |
| 32.2 | ![](ethyl ester) | 548 | 0.62 | X011_S03 |
| 32.3 | ![](2-methoxyethyl ester) | 578 | 0.60 | X011_S03 |
| 32.4 | ![](benzyl ester) | 532 | 0.70 | X012_S01 |

EXAMPLE 33

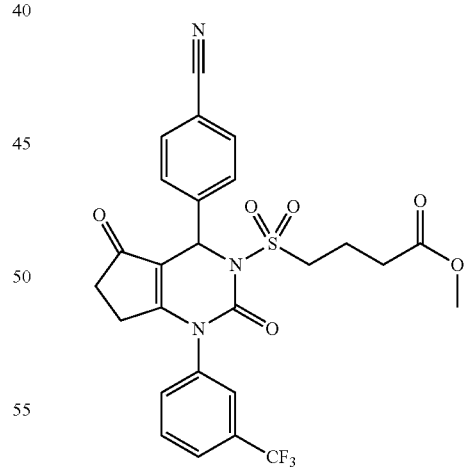

(S)-Methyl 4-(4-cyano-2-(methylsulfonyl)phenyl)-2,5-dioxo-1-(3-(trifluoromethyl)-phenyl)-4,5,6,7-tetrahydro-1H-cyclopenta[d]pyrimidine-3(2H)-carboxylate The title compound is prepared in analogy to ethyl 4-(4-cyanophenyl)-2,5-dioxo-1-(3-(tri-fluoromethyl)phenyl)-4,5,6,7-tetrahydro-1H-cyclopenta[d]pyrimidine-3(2H)-carboxylate (example 31, 110 mg, 0.23 mmol), using (S)-4-(2,5-dioxo-1-(3-(trifluoromethyl)phenyl)-2,3,4,5,6,7-hexahydro-1H-cyclopenta[d]pyrimidin-4-yl)-3-(methylsulfonyl)benzonitrile (example 10A) as starting material and substituting ethyl chloroformate with methyl chloroformate. Yield: 76 mg; ESI mass spectrum [M+H]⁺=534; Retention time HPLC: 1.01 min (Z018_S04).

EXAMPLE 34

Methyl 4-(4-(4-Cyanophenyl)-2,5-dioxo-1-(3-(trifluoromethyl)phenyl)-6,7-dihydro-1H-cyclopenta[d]pyrimidin-3(2H,4H,5H)-ylsulfonyl)butanoate A solution of 4-(2,5-dioxo-1-(3-(trifluoromethyl)phenyl)-2,3,4,5,6,7-hexahydro-1H-cyclopenta[d]pyrimidin-4-yl)benzonitrile (example 1, 70 mg, 0.18 mmol) in a mixture of tetrahydrofuran (1.5 mL) and N,N-dimethylformamide (150 μL) is treated with sodium hydride (60% in mineral oil, 28 mg, 0.7 mmol) and stirred at room temperature for 5 min Methyl 4-(chlorosulfonyl)butanoate (106 mg, 0.53 mmol) is added, and the mixture is stirred at 50° C. over night. The mixture is diluted with water and N,N-dimethylformamide and purified by reversed phase HPLC (Wate7rs SunFire™-C$_{18}$, gradient of acetonitrile in water, 0.1% TFA). Yield: 48 mg; ESI mass spectrum [M+H]$^+$=562; Retention time HPLC: 0.95 min (Z018_S04).

EXAMPLE 35

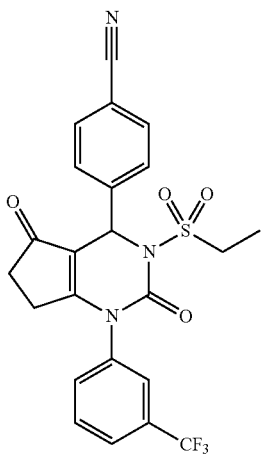

4-(3-(Ethylsulfonyl)-2,5-dioxo-1-(3-(trifluoromethyl)phenyl)-2,3,4,5,6,7-hexahydro-1H-cyclopenta[d]pyrimidin-4-yl)benzonitrile The title compound is prepared in analogy to methyl 4-(4-(4-cyanophenyl)-2,5-dioxo-1-(3-(trifluoromethyl)phenyl)-6,7-dihydro-1H-cyclopenta[d]pyrimidin-3(2H,4H,5H)-yl-sulfonyl)butanoate (example 34), substituting 4-(chlorosulfonyl)butanoate with ethane-sulfonyl chloride. Yield: 11 mg; ESI mass spectrum [M+H]$^+$=490; Retention time HPLC: 0.94 min (Z018_S04).

EXAMPLE 36

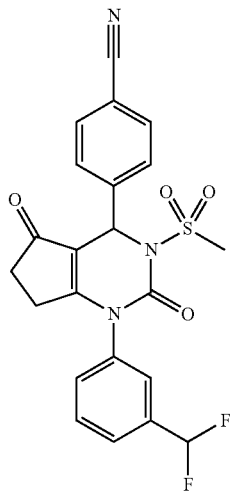

4-(1-(3-(Difluoromethyl)phenyl)-3-(methylsulfonyl)-2,5-dioxo-2,3,4,5,6,7-hexahydro-1H-cyclopenta[d]pyrimidin-4-yl)benzonitrile 4-(1-(3-(Difluoromethyl)phenyl)-2,5-dioxo-2,3,4,5,6,7-hexahydro-1H-cyclopenta[d]-pyrimidin-4-yl)benzonitrile (example 11, 100 mg, 0.26 mmol) is added to a suspension of sodium hydride (60% in mineral oil, 30 mg, 0.74 mmol) in tetrahydrofuran (3.0 mL). After 10 min methanesulfonyl chloride (42 µL, 0.55 mmol) is added and the mixture is heated at 50° C. over night. The mixture is cooled at room temperature, diluted with water (0.5 mL) and purified by reversed phase HPLC (Waters SunFire™-C$_{18}$, gradient of acetonitrile in water, 0.1% TFA). Yield: 74 mg; ESI mass spectrum [M+H]$^+$=458; Retention time HPLC: 0.76 min (005_CA01).

EXAMPLE 37

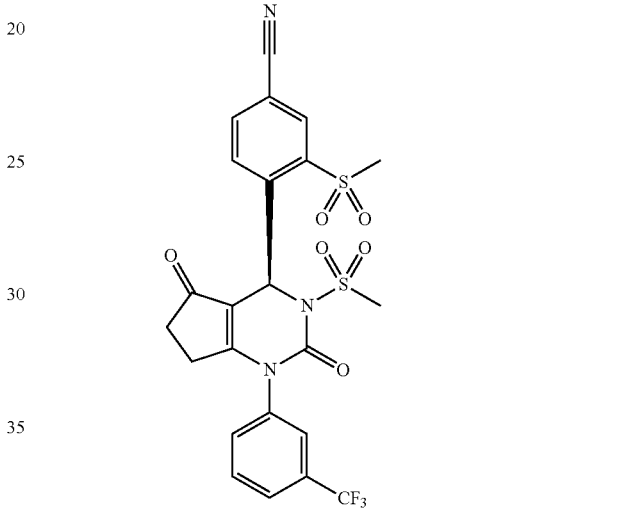

3-(Methylsulfonyl)-4-(3-(methylsulfonyl)-2,5-dioxo-1-(3-(trifluoromethyl)phenyl)-2,3,4,5,6,7-hexahydro-1H-cyclopenta[d]pyrimidin-4-yl)benzonitrile Sodium hydride (60% in mineral oil, 20 mg, 0.50 mmol) is added to a solution of (S)-4-(2,5-dioxo-1-(3-(trifluoromethyl)phenyl)-2,3,4,5,6,7-hexahydro-1H-cyclopenta[d]-pyrimidin-4-yl)-3-(methylsulfonyl)benzonitrile (example 10A, 100 mg, 0.18 mmol based on 85% purity) in tetrahydrofuran (4.0 mL), and the mixture is stirred at room temperature for 20 min Methanesulfonyl chloride (29 µL, 0.38 mmol) is added and the mixture is stirred at room temperature for 2 h. Water is added and the mixture is extracted with dichloromethane. The phases are separated and the organic layer is concentrated under a) reduced pressure. The residue is purified by reversed phase HPLC (Waters Xbridge™-C$_{18}$, gradient of acetonitrile in water, 0.1% TFA). Yield: 76 mg; ESI mass spectrum [M+H]$^+$=554; Retention time HPLC: 0.57 min (X012_S01).

Examples 37.1-37.4

The following examples of Table 14 are prepared in analogy to 3-(methylsulfonyl)-4-(3-(methylsulfonyl)-2,5-dioxo-1-(3-(trifluoromethyl)phenyl)-2,3,4,5,6,7-hexahydro-1H-cyclopenta[d]pyrimidin-4-yl)benzonitrile (example 37), using the appropriate starting material as indicated in the table.

TABLE 14

[Structure: cyclopenta[d]pyrimidine core with R¹, methylsulfonyl, and 3-(trifluoromethyl)phenyl substituents]

| Example | Starting Material | R¹ | MS [M + H]⁺ | Retention time [min] | HPLC-Method |
|---------|---|---|---|---|---|
| 37.1 | example 15.2 | 4-methyl-3-cyanophenyl | 490 | 0.67 | X012_S01 |
| 37.2 | example 15 | 4-chloro-3-cyanophenyl (CN, Cl) | 510 | 0.66 | X012_S01 |
| 37.3 | example 10 | 4-(methylsulfonyl)-3-cyanophenyl | 554 | 0.57 | X012_S01 |
| 37.4 | example 14 | 4-(ethylsulfonyl)-3-cyanophenyl | 568 | 0.59 | X012_S01 |

Examples 38.1-38.2

The following examples of Table 15 are prepared in analogy to 3-(methylsulfonyl)-4-(3-(methylsulfonyl)-2,5-dioxo-1-(3-(trifluoromethyl)phenyl)-2,3,4,5,6,7-hexahydro-1H-cyclopenta[d]pyrimidin-4-yl)benzonitrile (example 37), using the appropriate starting material as indicated in the table and replacing tetrahydrofuran with acetonitrile as solvent.

TABLE 15

[Structure: cyclopenta[d]pyrimidine core with R¹, methylsulfonyl, and 3-(trifluoromethyl)phenyl substituents]

| Example | Starting Material | R¹ | MS [M + H]⁺ | Retention time [min] | HPLC-Method |
|---------|---|---|---|---|---|
| 38.1 | example 15.3 | 5-cyanopyridin-2-yl | 477 | 0.61 | X011_S03 |
| 38.2 | example 15.1 | 4-methoxy-3-cyanophenyl | 506 | 0.65 | X012_S03 |

EXAMPLE 39

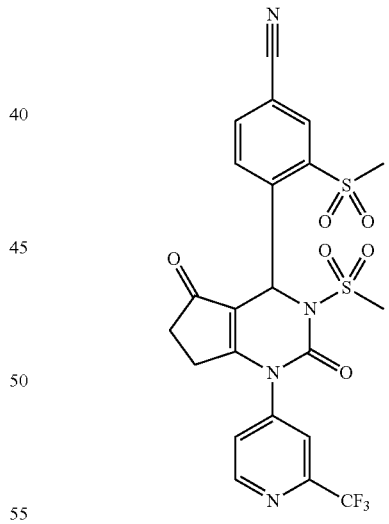

3-(Methylsulfonyl)-4-(3-(methylsulfonyl)-2,5-dioxo-1-(2-(trifluoromethyl)pyridin-4-yl)-2,3,4,5,6,7-hexahydro-1H-cyclopenta[d]pyrimidin-4-yl)benzonitrile 4-(2,5-dioxo-1-(2-(trifluoromethyl)pyridin-4-yl)-2,3,4,5,6,7-hexahydro-1H-cyclopenta[d]-pyrimidin-4-yl)-3-(methylsulfonyl)benzonitrile (example 15.6, 150 mg, 0.32 mmol) is added to a suspension of sodium hydride (60% in mineral oil, 35 mg, 0.88 mmol) in tetrahydrofuran (8.0 mL). After 10 min methanesulfonyl chloride (49 µL, 0.63 mmol) is added and the mixture is heated at 50° C. for 1.5 h. The mixture is cooled at room temperature and treated with water (1 mL). The mixture is stirred at room temperature for 30 min and purified by reversed phase HPLC (first purification: Waters SunFire™-$C_{18}$, gradient of acetonitrile in water, 0.1% TFA; second purification: Waters Xbridge™-$C_{18}$, gradient of acetonitrile in water, 0.1% $NH_3$). Yield: 20 mg; ESI mass spectrum $[M+H]^+$=555; Retention time HPLC: 0.90 min (Z011_S03).

EXAMPLE 40

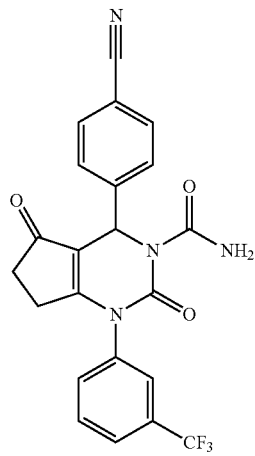

4-(4-Cyanophenyl)-2,5-dioxo-1-(3-(trifluoromethyl) phenyl)-4,5,6,7-tetrahydro-1H-cyclopenta[d]pyrimidine-3(2H)-carboxamide A solution of 4-nitrophenyl 4-(4-cyanophenyl)-2,5-dioxo-1-(3-(trifluoromethyl)phenyl)-4,5,6,7-tetrahydro-1H-cyclopenta[d]pyrimidine-3(2H)-carboxylate (intermediate 4, 25 mg, 45 µmol) in acetonitrile (1.0 mL) is treated with ammonium carbonate (9 mg, 90 µmol), and the mixture is stirred at room temperature for 30 min and purified by reversed phase HPLC (Waters SunFire™-$C_{18}$, gradient of acetonitrile in water, 0.1% TFA). Yield: 3 mg; ESI mass spectrum $[M+H]^+$=441; Retention time HPLC: 0.65 min (X018_S01).

EXAMPLE 41

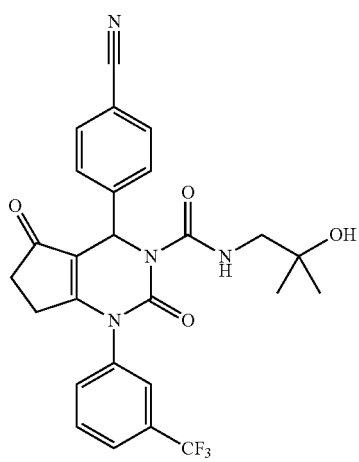

4-(4-Cyanophenyl)-N-(2-hydroxy-2-methylpropyl)-2,5-dioxo-1-(3-(trifluoromethyl)-phenyl)-4,5,6,7-tetrahydro-1H-cyclopenta[d]pyrimidine-3(2H)-carboxamide A solution of 4-nitrophenyl 4-(4-cyanophenyl)-2,5-dioxo-1-(3-(trifluoromethyl)phenyl)-4,5,6,7-tetrahydro-1H-cyclopenta[d]pyrimidine-3(2H)-carboxylate (intermediate 4, 250 mg, 0.44 mmol) in acetonitrile (5.0 mL) is treated with 1-amino-2-methylpropan-2-ol (80 mg, 0.90 mmol), and the mixture is stirred at room temperature for 1 h and purified by reversed phase HPLC (Waters Xbridge™-$C_{18}$, gradient of acetonitrile in water, 0.1% $NH_3$). Yield: 179 mg; ESI mass spectrum $[M+H]^+$=513; Retention time HPLC: 0.86 min (Z011_803).

Examples 41A and 41B

Enantiomers of Example 41

The enantiomers of racemic 4-(4-cyanophenyl)-N-(2-hydroxy-2-methylpropyl)-2,5-dioxo-1-(3-(trifluoromethyl) phenyl)-4,5,6,7-tetrahydro-1H-cyclopenta[d]pyrimidine-3 (2H)-carboxamide (example 41, 179 mg, 0.35 mmol) are separated by preparative supercritical fluid chromatography on a chiral phase (Daicel Chiralpak IA, 20×250 mm, 5 µm, 20% MeOH+0.2% diethylamine in supercritical $CO_2$, 40° C., 150 bar back pressure).

EXAMPLE 41A

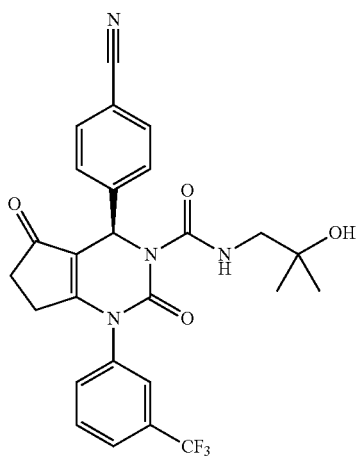

(R)-4-(4-Cyanophenyl)-N-(2-hydroxy-2-methylpropyl)-2,5-dioxo-1-(3-(trifluoro-methyl)phenyl)-4,5,6, 7-tetrahydro-1H-cyclopenta[d]pyrimidine-3(2H)-carboxamide Yield: 50 mg; ESI mass spectrum $[M+H]^+$=513; Retention time: 2.3 min (early eluting enantiomer) (I_IA_20_MeOH_DEA).

EXAMPLE 41B

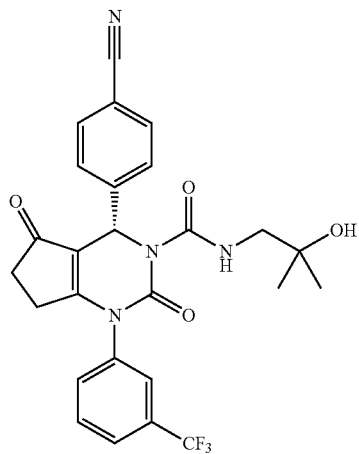

(S)-4-(4-Cyanophenyl)-N-(2-hydroxy-2-methylpropyl)-2,5-dioxo-1-(3-(trifluoro-methyl)phenyl)-4,5,6,7-tetrahydro-1H-cyclopenta[d]pyrimidine-3(2H)-carboxamide Yield: 47 mg; ESI mass spectrum [M+H]$^+$=513; Retention time: 4.1 min (late eluting enantiomer) (I_IA_20_MeOH_DEA).

Examples 41.1-41.31

The following examples of Table 16 are prepared in analog to 4-(4-cyanophenyl)-N-(2-hydroxy-2-methylpropyl)-2,5-dioxo-1-(3-(trifluoromethyl)phenyl)-4,5,6,7-tetrahydro-1H-cyclopenta[d]pyrimidine-3(2H)-carboxamide (example 41), using the appropriate amine as reagent.

TABLE 16

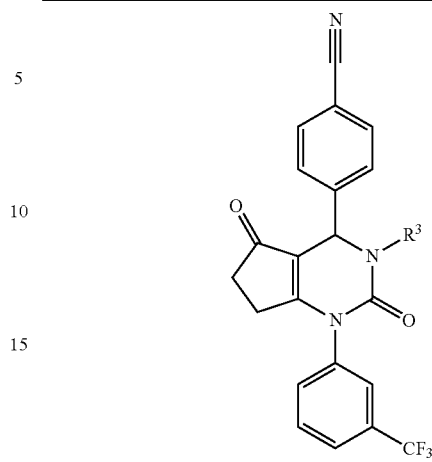

| Example | R$^3$ | MS [M + H]$^+$ | Retention time [min] | HPLC-Method |
|---|---|---|---|---|
| 41.1 | | 499 | 0.52 | 002_CA07 |
| 41.2 | | 499 | 0.52 | 002_CA07 |
| 41.3 | | 499 | 0.53 | 002_CA07 |
| 41.4 | | 499 | 0.53 | 002_CA07 |
| 41.5 | | 511 | 0.53 | 002_CA07 |
| 41.6 | | 511 | 0.56 | 002_CA07 |
| 41.7 | | 511 | 0.89 | Z11S_03 |
| 41.8 | | 511 | 0.86 | Z11S_03 |
| 41.9 | | 513 | 0.60 | 002_CA07 |

TABLE 16-continued

| Example | R³ | MS [M + H]⁺ | Retention time [min] | HPLC-Method |
|---|---|---|---|---|
| 41.10 | -C(O)NH-CH₂CH₂-CH(OH)-CH₃ | 513 | 0.54 | 002_CA07 |
| 41.11 | -C(O)NH-CH₂-(oxazol-2-yl) | 522 | 0.55 | 002_CA07 |
| 41.12 | -C(O)-(3,4-dimethylpyrrolidin-1-yl) | 523 | 0.59 | 002_CA07 |
| 41.13 | -C(O)NH-CH₂-(tetrahydrofuran-3-yl) | 525 | 0.90 | Z11S_03 |
| 41.14 | -C(O)NH-(tetrahydropyran-3-yl) (R) | 525 | 0.59 | 002_CA07 |
| 41.15 | -C(O)NH-(tetrahydropyran-3-yl) (S) | 525 | 0.59 | 002_CA07 |
| 41.16 | -C(O)NH-(tetrahydropyran-4-yl) | 525 | 0.57 | 002_CA07 |
| 41.17 | -C(O)NH-CH₂CH₂-C(CH₃)₂-OH | 527 | 0.88 | Z011_S03 |
| 41.18 | -C(O)NH-CH₂CH₂-O-CH(CH₃)₂ | 527 | 0.62 | 002_CA07 |
| 41.19 | -C(O)NH-CH₂CH₂-S(O)₂-CH₃ | 529 | 0.65 | 002_CA03 |
| 41.20 | -C(O)NH-CH₂-(1-methyl-imidazol-4-yl) | 535 | 0.52 | 002_CA07 |
| 41.21 | -C(O)NH-CH₂-(1-methyl-imidazol-5-yl) | 535 | 0.51 | 002_CA07 |
| 41.22 | -C(O)NH-CH₂-(1-methyl-pyrazol-5-yl) | 535 | 0.54 | 002_CA07 |
| 41.23 | -C(O)NH-CH₂-(tetrahydropyran-4-yl) | 539 | 0.58 | 002_CA07 |

TABLE 16-continued

[Structure: 4-(4-Cyanophenyl)-substituted cyclopenta[d]pyrimidine core with R³ substituent on N3 and 3-(trifluoromethyl)phenyl on N1]

| Example | R³ | MS [M + H]⁺ | Retention time [min] | HPLC-Method |
|---|---|---|---|---|
| 41.24 | trans-2-hydroxycyclohexyl acetamide | 539 | 0.89 | 005_CA01 |
| 41.25 | (1,3-dioxan-2-yl)methyl acetamide | 541 | 0.56 | 002_CA07 |
| 41.26 | (4-methoxytetrahydrofuran-3-yl) acetamide | 541 | 0.89 | Z011_S03 |
| 41.27 | (1,1-dioxo-tetrahydrothiophen-3-yl) acetamide | 559 | 0.89 | Z018_S04 |
| 41.28 | ethylsulfonylethyl acetamide | 561 | 0.54 | 002_CA07 |
| 41.29 | (1,1-dioxo-tetrahydrothiopyran-4-yl) acetamide | 573 | 0.85 | Z011_S03 |
| 41.30 | (3-methyl-1,1-dioxo-tetrahydrothiophen-3-yl) acetamide | 573 | 0.57 | 001_CA07 |
| 41.31 | isopropylsulfonylethyl acetamide | 575 | 0.56 | 002_CA07 |

EXAMPLE 42

4-(4-Cyanophenyl)-2,5-dioxo-N-(1,1-dioxo-1λ⁶-thietan-3-yl)-1-(3-(trifluoromethyl)-phenyl)-4,5,6,7-tetrahydro-1H-cyclopenta[d]pyrimidine-3(2H)-carboxamide N,N-Diisopropylethylamine (170 µL, 1.00 mmol), 4-dimethylaminopyridine (34 mg, 0.28 mmol) and 4-nitrophenyl chloroformate (56 mg, 0.28 mmol) is added to a solution of 4-(2,5-dioxo-1-(3-(trifluoromethyl)phenyl)-2,3,4,5,6,7-hexahydro-1H-cyclopenta[d]-pyrimidin-4-yl)benzonitrile (example 1, 100 mg, 0.25 mmol) in acetonitrile (2.0 mL), and the mixture is stirred at room temperature over night. 1,1-Dioxo-1λ⁶-thietan-3-amine hydrochloride (59 mg, 0.38 mmol) is added, and the mixture is stirred for 1 h and purified by reversed phase HPLC (Waters SunFire™-C₁₈, gradient of acetonitrile in water, 0.1% TFA). Yield: 73 mg; ESI mass spectrum [M+H]⁺=545; Retention time HPLC: 0.81 min (005_CA01).

Examples 42.1-42.8

The following examples of Table 17 are prepared in analogy to 4-(4-cyanophenyl)-2,5-dioxo-N-(1,1-dioxo-1λ⁶-thietan-3-yl)-1-(3-(trifluoromethyl)phenyl)-4,5,6,7-tetrahydro-1H-cyclopenta[d]pyrimidine-3(2H)-carboxamide (example 42), using the appropriate amine as reagent.

TABLE 17

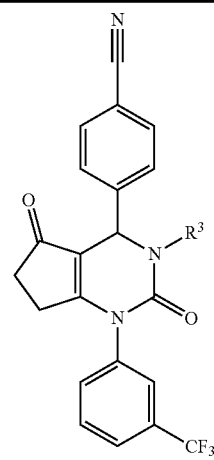

| Example | R³ | MS [M + H]⁺ | Retention time [min] | HPLC-Method |
|---|---|---|---|---|
| 42.1 | | 525 | 0.85 | 005_CA01 |
| 42.2 | | 525 | 0.86 | 005_CA01 |
| 42.3 | | 525 | 0.86 | 005_CA01 |
| 42.4 | | 525 | 0.85 | 005_CA01 |
| 42.5 | | 527 | 0.53 | Z006_U01 |
| 42.6 | | 527 | 0.98 | Z018_S04 |

TABLE 17-continued

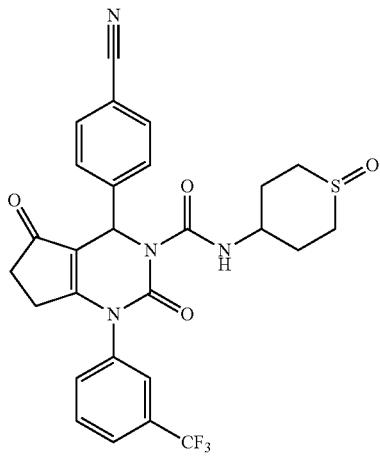

| Example | R³ | MS [M + H]⁺ | Retention time [min] | HPLC-Method |
|---|---|---|---|---|
| 42.7 | | 541 | 1.14 | Z018_S04 |
| 42.8 | | 573 | 1.02 | Z018_S04 |

EXAMPLE 43

4-(4-Cyanophenyl)-2,5-dioxo-N-(1-oxo-hexahydro-1λ⁴-thiopyran-4-yl)-1-(3-(trifluoro-methyl)phenyl)-4,5,6,7-tetrahydro-1H-cyclopenta[d]pyrimidine-3(2H)-carboxamide A solution of 4-(4-cyanophenyl)-2,5-dioxo-N-(tetrahydro-2H-thiopyran-4-yl)-1-(3-(tri-fluoromethyl)phenyl)-4,5,6,7-tetrahydro-1H-cyclopenta[d]pyrimidine-3(2H)-carboxamide (example 42.7, 94 mg, 0.18 mmol) in ethanol (1.0 mL) is cooled at −78° C. with an acetone/dry ice bath. Aqueous hydrogen peroxide (36%, 87 μL, 1.0 mmol) is added, and the mixture is stirred at −78° C. for 30 min Methyltrioxorhenium (VII) (1 mg, 4 μmol) is a) added, and the mixture is stirred at −78° C. for 30 min Another portion of methyltrioxo-rhenium (VII) (1 mg, 4 μmol) is added, and the mixture is stirred at −78° C. for 1 h. Aqueous potassium hydrogen sulfate solution (10%, 0.5 mL) and water is (10 mL) is added, and the mixture is filtered. The precipitate is dissolved in N,N-dimethylformamide, and the mixture is purified by reversed phase HPLC (Waters SunFire™-$C_{18}$, gradient of acetonitrile in water, 0.1% TFA). Yield: 40 mg; ESI mass spectrum $[M+H]^+$=557; Retention time HPLC: 0.96 min (Z018_S04).

EXAMPLE 44

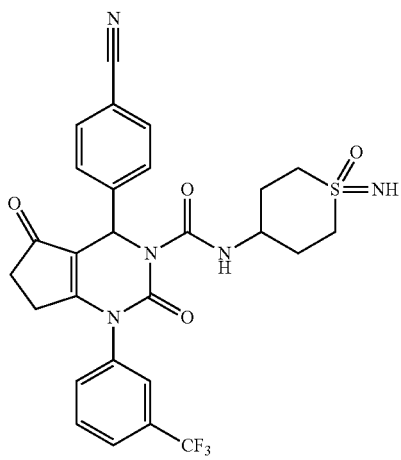

4-(4-Cyanophenyl)-2,5-dioxo-N-(1-imino-1-oxo-hexahydro-1λ⁶-thiopyran-4-yl)-1-(3-(trifluoromethyl)phenyl)-4,5,6,7-tetrahydro-1H-cyclopenta[d]pyrimidine-3(2H)-carboxamide 4-(4-Cyanophenyl)-2,5-dioxo-N-(1-oxo-hexahydro-1λ⁴-thiopyran-4-yl)-1-(3-(trifluoro-methyl)phenyl)-4,5,6,7-tetrahydro-1H-cyclopenta[d]pyrimidine-3(2H)-carboxamide (example 43, 40 mg, 72 μmol) is added to a solution of O-mesitylenesulfonylhydroxyl-amine (66 mg, 0.31 mmol) in dichloromethane (1.0 mL), and the mixture is stirred at room temperature over night. All volatiles are removed under reduced pressure, and the residue is purified by reversed phase HPLC (Waters SunFire™-$C_{18}$, gradient of acetonitrile in water, 0.1% TFA). Yield: 9 mg; ESI mass spectrum $[M+H]^+$=572; Retention time HPLC: 0.90 min (Z018_S04).

Examples 45.1-45.6

The following examples of Table 18 are prepared in analogy to 4-(4-cyanophenyl)-N-(2-hydroxy-2-methylpropyl)-2,5-dioxo-1-(3-(trifluoromethyl)phenyl)-4,5,6,7-tetrahydro-1H-cyclopenta[d]pyrimidine-3(2H)-carboxamide (example 41), using (R)-4-nitrophenyl 4-(4-cyanophenyl)-2,5-dioxo-1-(3-(trifluoromethyl)phenyl)-4,5,6,7-tetrahydro-1H-cyclopenta[d]pyrimidine-3(2H)-carboxylate (intermediate 30.1) as starting material and the appropriate amine as reagent.

TABLE 18

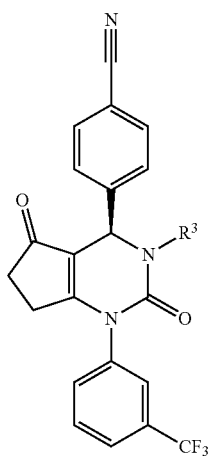

| Example | R³ | MS [M + H]⁺ | Retention time [min] | HPLC-Method |
|---|---|---|---|---|
| 45.1 | acetamide-CH₂-CN | 480 | 0.82 | 005_CA01 |
| 45.2 | N-cyclopropyl amide | 481 | 0.90 | 005_CA01 |
| 45.3 | N-CH₂CHF₂ amide | 505 | 0.88 | 005_CA01 |
| 45.4 | N-(2-hydroxycyclopentyl) amide | 525 | 1.06 | Z018_S04 |
| 45.5 | N-(hydroxytetrahydrofuranyl) amide | 527 | 0.99 | Z018_S04 |
| 45.6 | N-(1,1-dioxo-thietan-3-yl) amide | 545 | 1.01 | Z018_S04 |

EXAMPLE 46

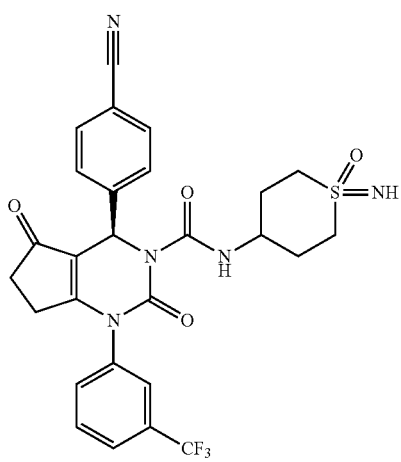

(R)-4-(4-Cyanophenyl)-2,5-dioxo-N-(1,1-dioxo-hexahydro-1λ⁶-thiopyran-4-yl)-1-(3-(trifluoromethyl)phenyl)-4,5,6,7-tetrahydro-1H-cyclopenta[d]pyrimidine-3(2H)-carboxamide N,N-Diisopropylethylamine (137 µL, 0.81 mmol), 4-dimethylaminopyridine (27 mg, 0.22 mmol) and 4-nitrophenyl chloroformate (45 mg, 0.22 mmol) is added to a solution of (R)-4-(2,5-dioxo-1-(3-(trifluoromethyl)phenyl)-2,3,4,5,6,7-hexahydro-1H-cyclopenta[d]-pyrimidin-4-yl)benzonitrile (example 1A, 80 mg, 0.20 mmol) in acetonitrile (2.0 mL), and the mixture is stirred at room temperature over night. 1,1-Dioxotetrahydro-2H-thiopyran-4-amine (74 mg, 0.40 mmol) is added, and the mixture is stirred for 1 h and purified by reversed phase HPLC (Waters SunFire™-C₁₈, gradient of acetonitrile in water, 0.1% TFA). Yield: 72 mg; ESI mass spectrum [M+H]⁺=573; Retention time HPLC: 1.01 min (Z018_S04).

Examples 47.1-47.21

The following examples of Table 19 are prepared in analog to 4-(4-cyanophenyl)-N-(2-hydroxy-2-methylpropyl)-2,5-dioxo-1-(3-(trifluoromethyl)phenyl)-4,5,6,7-tetrahydro-1H-cyclopenta[d]pyrimidine-3(2H)-carboxamide (example 41.0), using (S)-4-nitrophenyl 4-(4-cyano-2-(methylsulfonyl)phenyl)-2,5-dioxo-1-(3-(trifluoromethyl)phenyl)-4,5,6,7-tetrahydro-1H-cyclopenta[d]pyrimidine-3(2H)-carboxylate (intermediate 20.2) as starting material and the appropriate amine as reagent.

TABLE 19

| Example | R³ | MS [M+H]⁺ | Retention time [min] | HPLC-Method |
|---|---|---|---|---|
| 47.1 | (C(=O)NHCH₃) | 533 | 0.72 | 002_CA03 |
| 47.2 | (C(=O)NHEt) | 547 | 0.76 | 002_CA03 |
| 47.3 | (C(=O)NHCH₂CN) | 558 | 1.00 | Z018_S04 |
| 47.4 | (C(=O)NH-cyclopropyl) | 559 | 1.06 | Z018_S04 |
| 47.5 | (C(=O)NHiPr) | 561 | 0.67 | X012_S01 |
| 47.6 | (C(=O)NHCH(CH₃)CN) | 572 | 1.05 | Z018_S04 |
| 47.7 | (C(=O)NHCH₂-cyclopropyl) | 573 | 1.10 | Z018_S04 |
| 47.8 | (C(=O)NH-oxetanyl) | 575 | 0.99 | Z018_S04 |
| 47.9 | (C(=O)NHCH₂CH₂OCH₃) | 577 | 1.03 | Z018_S04 |

TABLE 19-continued

| Example | R³ | MS [M+H]⁺ | Retention time [min] | HPLC-Method |
|---|---|---|---|---|
| 47.10 | -C(O)NH-CH₂-CHF₂ | 583 | 1.05 | Z018_S04 |
| 47.11 | -C(O)NH-CH₂-(1-hydroxycyclopropyl) | 589 | 1.00 | Z018_S04 |
| 47.12 | -C(O)NH-(tetrahydrofuran-3-yl) | 589 | 1.02 | Z018_S04 |
| 47.13 | -C(O)NH-CH₂-C(CH₃)₂-OH | 591 | 1.00 | Z018_S04 |
| 47.14 | -C(O)NH-C(CH₃)₂-CH₂OH | 591 | 1.02 | Z018_S04 |
| 47.15 | -C(O)NH-(tetrahydropyran-4-yl) | 603 | 1.03 | Z018_S04 |
| 47.16 | -C(O)NH-CH₂-(3-hydroxycyclobutyl) | 603 | 0.98 | Z018_S04 |
| 47.17 | -C(O)NH-CH₂-(1-hydroxycyclobutyl) | 603 | 1.02 | Z018_S04 |
| 47.18 | -C(O)NH-(2-hydroxycyclopentyl) | 603 | 1.03 | Z018_S04 |
| 47.19 | -C(O)NH-(2-hydroxycyclopentyl) | 603 | 1.02 | Z018_S04 |
| 47.20 | -C(O)NH-CH₂CH₂-C(CH₃)₂-OH | 605 | 1.01 | Z018_S04 |
| 47.21 | -C(O)NH-(2-hydroxycyclohexyl) | 617 | 1.05 | Z018_S04 |

Examples 48.1-48.4

The following examples of Table 20 are prepared in analog to 4-(4-cyanophenyl)-2,5-dioxo-N-(1,1-dioxo-1λ⁶-thietan-3-yl)-1-(3-(trifluoromethyl)phenyl)-4,5,6,7-tetrahydro-1H-cyclopenta[d]pyrimidine-3(2H)-carboxamide (example 42), using (S)-4-nitrophenyl 4-(4-cyano-2-(methylsulfonyl)phenyl)-2,5-dioxo-1-(3-(trifluoromethyl)phenyl)-4,5,6,7-tetrahydro-1H-cyclopenta[d]pyrimidine-3(2H)-carboxylate (intermediate 30.2) as starting material and the appropriate amine as reagent.

TABLE 20

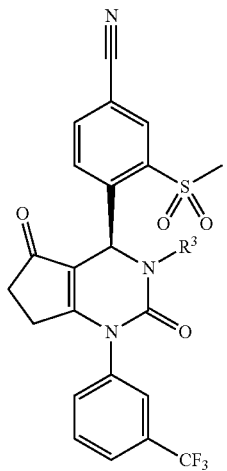

| Example | R³ | MS [M+H]⁺ | Retention time [min] | HPLC-Method |
|---|---|---|---|---|
| 48.1 | (acyl-NH-C(CN)(cyclopropyl)) | 584 | 1.09 | Z018_S04 |
| 48.2 | (acyl-NH-cyclobutyl) | 585 | 1.15 | Z018_S04 |
| 48.3 | (acyl-NH-cyclobutyl-OH) | 589 | 0.97 | Z018_S04 |
| 48.4 | (acyl-NH-cyclopentyl-OH) | 603 | 0.99 | Z018_S04 |

4-(4-Cyano-2-fluorophenyl)-N-methyl-2,5-dioxo-1-(3-(trifluoromethyl)phenyl)-4,5,6,7-tetrahydro-1H-cyclopenta[d]pyrimidine-3(2H)-carboxamide 4-Nitrophenyl chloroformate (23 mg, 0.11 mmol) is added to a solution of 4-(2,5-dioxo-1-(3-(trifluoromethyl)phenyl)-2,3,4,5,6,7-hexahydro-1H-cyclopenta[d]pyrimidin-4-yl)-3-fluorobenzonitrile (example 18, 43 mg, 0.10 mmol), N,N-diisopropylethylamine (70 μL, 0.41 mmol) and 4-dimethylaminopyridine (14 mg, 0.11 mmol) in acetonitrile (3.0 mL), and the mixture is stirred at room temperature over night. Another portion of 4-Nitrophenyl chloroformate (50 mg, 0.24 mmol) and 4-dimethylaminopyridine (30 mg, 0.24 mmol) is added, and the mixture is stirred over night. Methylamine (2.0 M in tetrahydrofuran, 155 μL, 0.31 mmol) is added, and the mixture is stirred for 20 min at room temperature and purified by reversed phase HPLC (Waters SunFire™-C₁₈, gradient of acetonitrile in water, 0.1% TFA). Yield: 27 mg; ESI mass spectrum [M+H]⁺=473; Retention time HPLC: 0.59 min (001_CA07).

Examples 49A and 49B

Enantiomers of Example 49

The enantiomers of racemic 4-(4-cyano-2-fluorophenyl)-N-methyl-2,5-dioxo-1-(3-(trifluoromethyl)phenyl)-4,5,6,7-tetrahydro-1H-cyclopenta[d]pyrimidine-3(2H)-carboxamide (example 49, 24 mg, 0.05 mmol) are separated by preparative supercritical fluid chromatography on a chiral phase (Daicel Chiralpak IA, 2×20×250 mm, 5 μm, 15% MeOH+0.2% diethylamine in supercritical CO₂, 40° C., 120 bar back pressure).

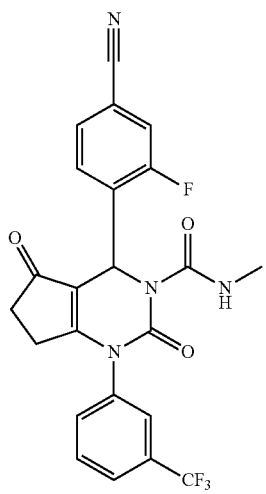

EXAMPLE 49

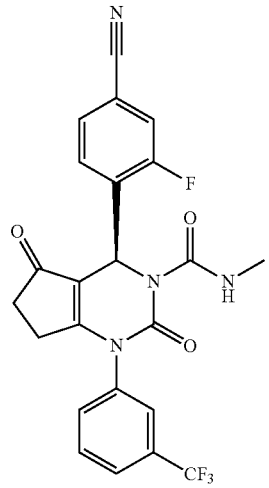

EXAMPLE 49A (S)-4-(4-Cyano-2-fluorophenyl)-N-methyl-2,5-di-oxo-1-(3-(trifluoromethyl)phenyl)-4,5,6,7-tetrahydro-1H-cyclopenta[d]pyrimidine-3(2H)-carboxamide Yield: 10 mg; ESI mass spectrum [M+H]$^+$=473; Retention time: 2.85 min (early eluting enantiomer) (I_IA_15_MeOH_DEA).

EXAMPLE 49B

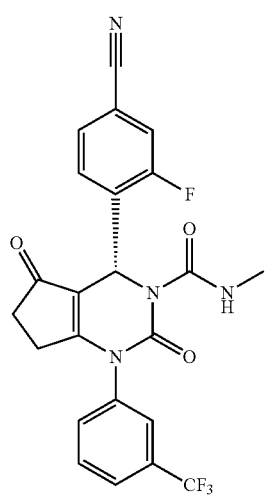

(R)-4-(4-Cyano-2-fluorophenyl)-N-methyl-2,5-di-oxo-1-(3-(trifluoromethyl)phenyl)-4,5,6,7-tetrahydro-1H-cyclopenta[d]pyrimidine-3(2H)-carboxamide Yield: 10 mg; ESI mass spectrum [M+H]$^+$=473; Retention time: 3.72 min (late eluting enantiomer) (I_IA_15_MeOH_DEA).

Examples 49.1-49.3

The following examples of Table 21 are prepared in analogy 4-(4-cyano-2-fluorophenyl)-N-methyl-2,5-dioxo-1-(3-(trifluoromethyl)phenyl)-4,5,6,7-tetrahydro-1H-cyclopenta[d]-pyrimidine-3(2H)-carboxamide (example 49), substituting methylamine with the appropriate amine as reagent.

TABLE 21

| Example | R$^3$ | MS [M + H]$^+$ | Retention time [min] | HPLC-Method |
|---|---|---|---|---|
| 49.1 | -C(O)NHEt | 487 | 0.80 | 002_CA03 |
| 49.2 | -C(O)NHCH$_2$CH$_2$OCH$_3$ | 517 | 1.06 | Z018_S04 |
| 49.3 | -C(O)NHCH$_2$CH$_2$S(O)$_2$CH$_3$ | 565 | 0.71 | 002_CA03 |

Examples 50.1-50.7

The following examples of Table 22 are prepared in analogy to 4-(4-cyano-2-fluoro-phenyl)-N-methyl-2,5-dioxo-1-(3-(trifluoromethyl)phenyl)-4,5,6,7-tetrahydro-1H-cyclopenta[d]pyrimidine-3(2H)-carboxamide (example 49), using the appropriate starting material as indicated in the table.

TABLE 22

[Structure: 4-R¹-substituted cyclopenta[d]pyrimidine-2,5-dione core with N-methyl carboxamide and 3-(trifluoromethyl)phenyl group]

| Example | Starting Material | R¹ | MS [M+H]⁺ | Retention time [min] | HPLC-Method |
|---|---|---|---|---|---|
| 50.1 | example 15.3 | 5-cyano-pyridin-2-yl | 456 | 0.61 | X011_S03 |
| 50.2 | example 15.2 | 4-cyano-2-methyl-phenyl | 469 | 0.87 | 005_CA01 |
| 50.3 | example 15.1 | 4-cyano-2-methoxy-phenyl | 485 | 0.71 | X012_S01 |
| 50.4 | example 15 | 4-cyano-2-chloro-phenyl | 489 | 0.76 | X012_S01 |
| 50.5 | example 17 | 4-cyano-2-(methylsulfinyl)-phenyl | 517 | 0.97 | Z017_S04 |
| 50.6 | example 13 | 4-cyano-2-bromo-phenyl | 533, 535 | 0.64 | X012_S01 |

TABLE 22-continued

| Example | Starting Material | R¹ | MS [M+H]⁺ | Retention time [min] | HPLC-Method |
|---|---|---|---|---|---|
| 50.7 | example 14 | 4-cyano-2-(ethylsulfonyl)-phenyl | 547 | 0.69 | X012_S01 |

Examples 51.1-51.4

The following Examples of Table 23 are prepared in analogy to 4-(4-cyano-2-fluoro-phenyl)-N-methyl-2,5-dioxo-1-(3-(trifluoromethyl)phenyl)-4,5,6,7-tetrahydro-1H-cyclopenta[d]pyrimidine-3(2H)-carboxamide (example 49), using the appropriate starting material as indicated in the table and the appropriate amine as reagent.

TABLE 23

[Structure: 4-R¹-substituted cyclopenta[d]pyrimidine-2,5-dione core with N-ethyl carboxamide and 3-(trifluoromethyl)phenyl group]

| Example | Starting Material | R¹ | MS [M+H]⁺ | Retention time | HPLC-Method |
|---|---|---|---|---|---|
| 51.1 | example 15.1 | 4-cyano-2-methoxy-phenyl | 485 | 0.71 | X012_S01 |

TABLE 23-continued

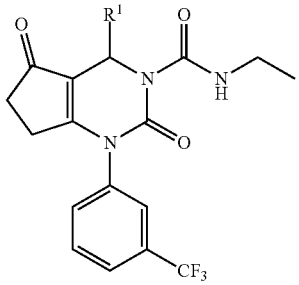

| Example | Starting Material | R¹ | MS [M + H]⁺ | Retention time | HPLC-Method |
|---|---|---|---|---|---|
| 51.2 | example 15 | 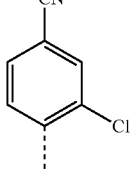 | 503 | 0.68 | X012_S01 |
| 51.3 | example 14 | 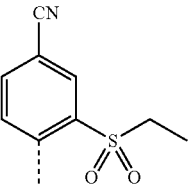 | 561 | 0.65 | X012_S01 |
| 51.4 | example 17 | 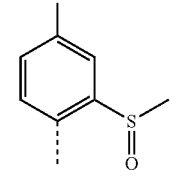 | 531 | 1.04 | Z018_S04 |

4-(4-Cyanophenyl)-1-(3-(difluoromethyl)phenyl)-N-(3-hydroxypropyl)-2,5-dioxo-4,5,6,7-tetrahydro-1H-cyclopenta[d]pyrimidine-3(2H)-carboxamide The title compound is prepared in analogy to 4-(4-cyano-2-fluorophenyl)-N-methyl-2,5-dioxo-1-(3-(trifluoromethyl)phenyl)-4,5,6,7-tetrahydro-1H-cyclopenta[d]pyrimidine-3(2H)-carboxamide (example 49), using 4-(1-(3-(difluoromethyl)phenyl)-2,5-dioxo-2,3,4,5,6,7-hexahydro-1H-cyclopenta[d]pyrimidin-4-yl)benzonitrile (example 11, 100 mg, 0.26 mmol) as starting material and replacing methylamine with 3-aminopropanol. Yield: 70 mg; ESI mass spectrum [M+H]⁺=481; Retention time HPLC: 0.71 min (005_CA01).

Examples 52A and 52B

Enantiomers of Example 52

The enantiomers of racemic 4-(4-cyanophenyl)-1-(3-(difluoromethyl)phenyl)-N-(3-hydroxypropyl)-2,5-dioxo-4,5,6,7-tetrahydro-1H-cyclopenta[d]pyrimidine-3(2H)-carboxamide (example 52, 67 mg, 0.14 mmol) are separated by preparative supercritical fluid chromatography on a chiral phase (Daicel Chiralpak IB, 20×250 mm, 5 µm, 50% MeOH+0.2% diethylamine in supercritical $CO_2$, 40° C., 120 bar back pressure).

EXAMPLE 52A

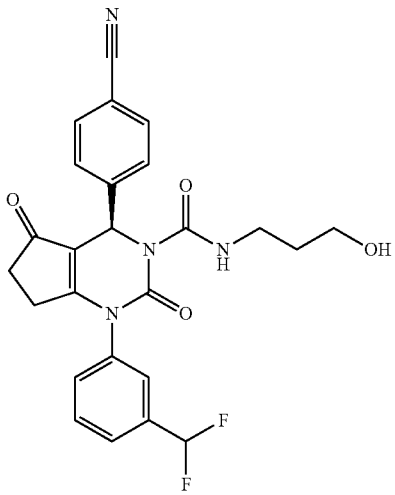

EXAMPLE 52

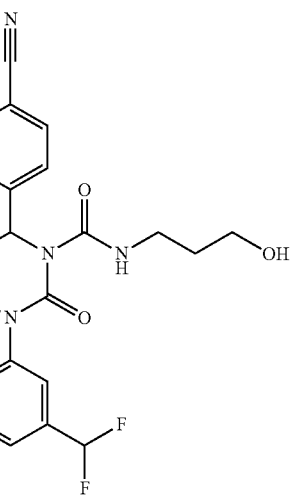

(R)-4-(4-Cyanophenyl)-1-(3-(difluoromethyl)phenyl)-N-(3-hydroxypropyl)-2,5-dioxo-4,5,6,7-tetrahydro-1H-cyclopenta[d]pyrimidine-3(2H)-carboxamide Yield: 29 mg; ESI mass spectrum [M+H]⁺=481; Retention time: 1.28 min (early eluting enantiomer) (I_IB_40_MeOH_DEA).

EXAMPLE 52B

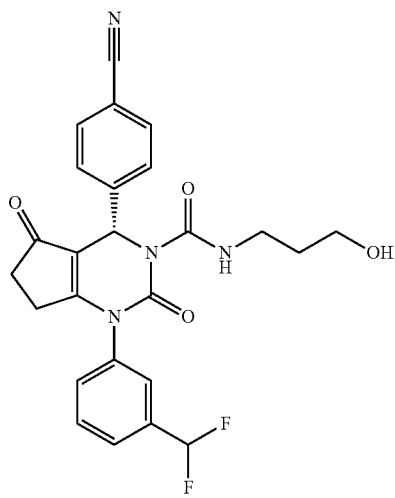

(S)-4-(4-Cyanophenyl)-1-(3-(difluoromethyl)phenyl)-N-(3-hydroxypropyl)-2,5-dioxo-4,5,6,7-tetrahydro-1H-cyclopenta[d]pyrimidine-3(2H)-carboxamide Yield: 28 mg; ESI mass spectrum [M+H]$^+$=481; Retention time: 4.31 min (late eluting enantiomer) (I_IB_40_MeOH_DEA).

Examples 52.1-52.5

The following examples of Table 24 are prepared in analogy to 4-(4-cyanophenyl)-1-(3-(difluoromethyl)phenyl)-N-(3-hydroxypropyl)-2,5-dioxo-4,5,6,7-tetrahydro-1H-cyclopenta[d]pyrimidine-3(2H)-carboxamide (example 52), replacing 3-aminopropanol with the appropriate amine as reagent.

TABLE 24

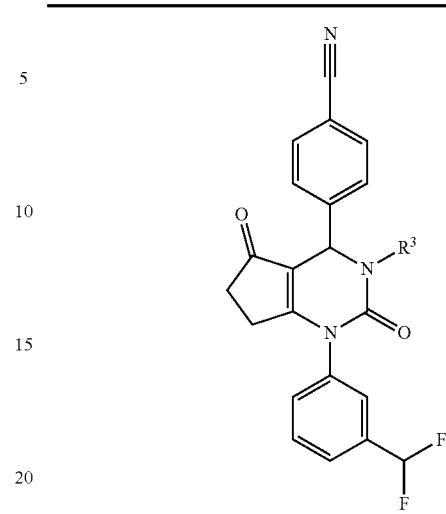

| Example | R³ | MS [M + H]⁺ | Retention time [min] | HPLC-Method |
|---------|-----|-------------|----------------------|-------------|
| 52.1 | | 437 | 0.97 | Z017_S04 |

TABLE 24-continued

| Example | R³ | MS [M + H]⁺ | Retention time [min] | HPLC-Method |
|---------|-----|-------------|----------------------|-------------|
| 52.2 | | 451 | 0.73 | 002_CA03 |
| 52.3 | | 467 | 0.63 | 002_CA03 |
| 52.4 | | 481 | 0.71 | 002_CA03 |
| 52.5 | 2OH) | 495 | 0.79 | 005_CA01 |

Examples 53.1-53.5

The following examples of Table 25 are prepared in analogy to 4-(4-cyano-2-fluoro-phenyl)-N-methyl-2,5-dioxo-1-(3-(trifluoromethyl)phenyl)-4,5,6,7-tetrahydro-1H-cyclopenta[d]pyrimidine-3(2H)-carboxamide (example 49), using 4-(1-(3-(difluoromethyl)-phenyl)-2,5-dioxo-2,3,4,5,6,7-hexahydro-1H-cyclopenta[d]pyrimidin-4-yl)-3-(methyl-sulfonyl)benzonitrile (example 15.4) as starting material and employing the appropriate amine as reagent.

TABLE 25

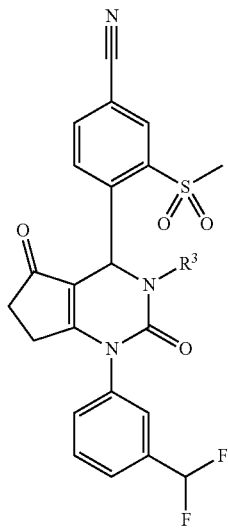

| Example | R³ | MS [M + H]⁺ | Retention time [min] | HPLC-Method |
|---|---|---|---|---|
| 53.1 | -C(O)NHCH₃ | 515 | 0.97 | Z018_S04 |
| 53.2 | -C(O)NHEt | 529 | 0.69 | 002_CA03 |
| 53.3 | -C(O)NH-cyclopropyl | 541 | 1.01 | Z018_S04 |
| 53.4 | -C(O)NH-iPr | 543 | 0.73 | 002_CA03 |
| 53.5 | -C(O)NHCH₂C(CH₃)₂OH | 573 | 0.95 | Z018_S04 |

TABLE 26

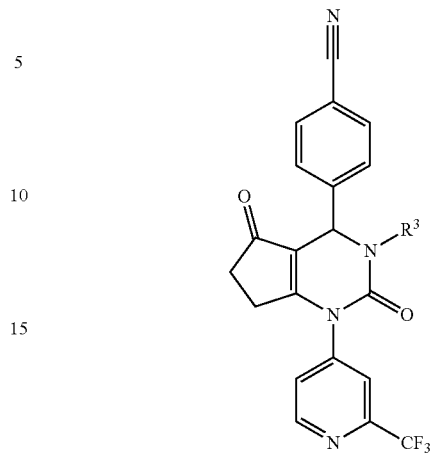

| Example | R³ | MS [M + H]⁺ | Retention time [min] | HPLC-Method |
|---|---|---|---|---|
| 54.1 | -C(O)NHCH₃ | 456 | 1.00 | Z018_S04 |
| 54.2 | -C(O)NHEt | 470 | 1.04 | Z018_S04 |
| 54.3 | -C(O)NH-cyclopropyl | 482 | 1.05 | Z018_S04 |
| 54.4 | -C(O)NH-iPr | 484 | 1.09 | Z018_S04 |

Examples 54.1-54.4

The following examples of Table 26 are prepared in analogy to 4-(4-cyanophenyl)-N-(2-hydroxy-2-methylpropyl)-2,5-dioxo-1-(3-(trifluoromethyl)phenyl)-4,5,6,7-tetrahydro-1H-cyclopenta[d]pyrimidine-3(2H)-carboxamide (example 41), using 4-nitrophenyl 4-(4-cyanophenyl)-2,5-dioxo-1-(2-(trifluoromethyl)pyridin-4-yl)-4,5,6,7-tetrahydro-1H-cyclopenta[d]pyrimidine-3(2H)-carboxylate (intermediate 30.3) as starting material and employing the appropriate amine as reagent.

EXAMPLE 55

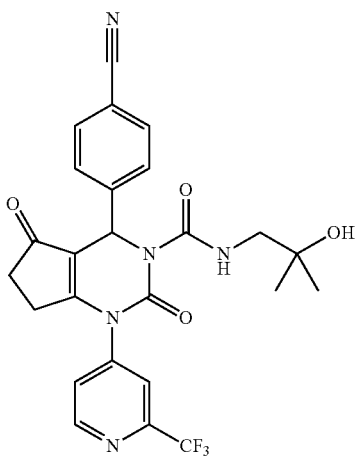

4-(4-Cyanophenyl)-N-(2-hydroxy-2-methylpropyl)-2,5-dioxo-1-(2-(trifluoromethyl)-pyridin-4-yl)-4,5,6,7-tetrahydro-1H-cyclopenta[d]pyrimidine-3(2H)-carboxamide The title compound is prepared in analogy to 4-(4-cyano-2-fluorophenyl)-N-methyl-2,5-dioxo-1-(3-(trifluoromethyl)phenyl)-4,5,6,7-tetrahydro-1H-cyclopenta[d]pyrimidine-3(2H)-carboxamide (example 49), using 4-nitrophenyl 4-(4-cyanophenyl)-2,5-dioxo-1-(2-(tri-fluoromethyl)pyridin-4-yl)-4,5,6,7-tetrahydro-1H-cyclopenta[d]pyrimidine-3(2H)-carboxylate (intermediate 30.3, 100 mg, 0.25 mmol) as starting material and employing 1-amino-2-methylpropan-2-ol as reagent. Yield: 60 mg; ESI mass spectrum [M+H]$^+$=514; Retention time HPLC: 0.97 min (Z018_S04).

Examples 56.1-56.2

The following examples of Table 27 are prepared in analogy to 4-(4-cyano-2-fluoro-phenyl)-N-methyl-2,5-dioxo-1-(3-(trifluoromethyl)phenyl)-4,5,6,7-tetrahydro-1H-cyclopenta[d]pyrimidine-3(2H)-carboxamide (example 49), using 4-(2,5-dioxo-1-(2-(trifluoro-methyl)pyridin-4-yl)-2,3,4,5,6,7-hexahydro-1H-cyclopenta[d]pyrimidin-4-yl)-3-(methylsulfonyl)benzonitrile (example 15.6) as starting material and employing the appropriate amine as reagent.

TABLE 27

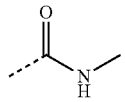

| Example | R$^3$ | MS [M + H]$^+$ | Retention time [min] | HPLC-Method |
|---------|-------|----------------|---------------------|-------------|
| 56.1 | 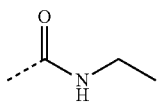 | 534 | 0.96 | Z018_S04 |
| 56.2 | 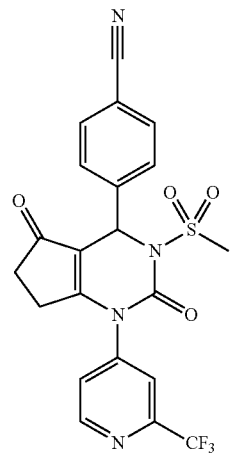 | 548 | 1.00 | Z018_S04 |

EXAMPLE 57

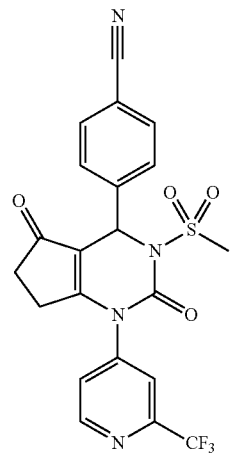

4-(3-(Methylsulfonyl)-2,5-dioxo-1-(2-(trifluoromethyl)pyridin-4-yl)-2,3,4,5,6,7-hexahydro-1H-cyclopenta[d]pyrimidin-4-yl)benzonitrile The title compound is prepared in analogy to 3-(methylsulfonyl)-4-(3-(methylsulfonyl)-2,5-dioxo-1-(2-(trifluoromethyl)pyridin-4-yl)-2,3,4,5,6,7-hexahydro-1H-cyclopenta[d]-pyrimidin-4-yl)benzonitrile (example 39), using 4-(2,5-dioxo-1-(2-(trifluoromethyl)pyridin-4-yl)-2,3,4,5,6,7-hexahydro-1H-cyclopenta[d]pyrimidin-4-yl)benzonitrile (example 15.5, 60 mg, 0.15 mmol) as starting material. Yield: 30 mg; ESI mass spectrum [M+H]$^+$=477; Retention time HPLC: 0.99 min (Z018_S04).

EXAMPLES

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: I-1270). All other materials were of the highest grade commercially available. The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 µL of these compound dilutions were mixed with 10 µl Neutrophil elastase (9 ng/ml in assay buffer) in a black 384 well OptiPlate (Perkin Elmer, Cat No.: 6007270) and incubated for 15 min at room temperature. Subsequently 10 µL substrate solution in assay buffer were added (250 µM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). IC$_{50}$ values were estimated using a sigmoidal concentration response curve with variable slope. Means of low values were taken as 0%, means of high values as 100%. The $IC_{50}$ values of selected compound in the Neutrophil Elastase assay are listed in Table 28.

TABLE 28

| Example | $IC_{50}$ [nM] |
| --- | --- |
| 1 | 33.3 |
| 1A | 11.5 |
| 1B | 8040 |
| 2 | 6.4 |
| 2A | 2.4 |
| 3 | 17.0 |
| 4 | 10.9 |
| 5 | 11.2 |
| 6 | 3.0 |
| 6.1 | 15.7 |
| 6.2 | 5.8 |
| 6.3 | 3.7 |
| 6.4 | 10.9 |
| 6.5 | 1.1 |
| 6.6 | 2.2 |
| 6.7 | 13.8 |
| 6.8 | 15.8 |
| 6.9 | 3.5 |
| 6.10 | 3.8 |
| 6.11 | 3.9 |
| 6.12 | 3.8 |
| 6.13 | 3.6 |
| 6.14 | 6.0 |
| 6.15 | 3.3 |
| 6.16 | 11.6 |
| 6.17 | 6.3 |
| 6.18 | 18.7 |
| 6.19 | 2.7 |
| 6.20 | 9.1 |
| 6.21 | 3.4 |
| 6.22 | 11.8 |
| 6.23 | 15.7 |
| 6.24 | 9.5 |
| 6.25 | 6.0 |
| 6.26 | 10.0 |
| 6.27 | 18.6 |
| 6.28 | 23.1 |
| 6.29 | 22.6 |
| 6.30 | 3.4 |
| 6.31 | 21.2 |
| 6.32 | 9.7 |
| 6.33 | 6.5 |
| 6.34 | 17.3 |
| 6.35 | 17.0 |
| 6.36 | 13.3 |
| 6.37 | 3.9 |
| 6.38 | 1.7 |
| 6.39 | 20.7 |
| 6.40 | 6.8 |
| 6.41 | 8.3 |
| 6.42 | 8.7 |
| 6.43 | 2.9 |
| 6.44 | 9.7 |
| 6.45 | 14.3 |
| 6.46 | 2.9 |
| 7 | 123.7 |
| 7.1 | <1 |
| 7.1A | <1 |
| 7.1B | 621.5 |
| 7.2 | <1 |
| 7.2A | <1 |
| 7.2B | 550.0 |
| 7.3 | <1 |
| 7.4 | <1 |
| 7.5 | 1.4 |
| 7.6 | <1 |
| 7.7 | 1.2 |
| 7.8 | <1 |
| 7.9 | <1 |
| 7.10 | <1 |
| 7.11 | <1 |
| 8 | 4.0 |
| 9 | 5.1 |
| 9A | 3.0 |
| 9B | 3180 |
| 10 | 5.8 |
| 10A | 2.6 |
| 10B | 98.4 |
| 11 | 37.4 |
| 12 | 201.0 |
| 13 | 17.9 |
| 14 | 4.7 |
| 14A | 1.2 |
| 14B | 33 |
| 15 | 30.1 |
| 15.1 | 42.1 |
| 15.2 | 28.6 |
| 15.3 | 106.3 |
| 15.3A | 31.5 |
| 15.3B | 1720 |
| 15.4 | 9.7 |
| 15.4A | 2.9 |
| 15.4B | 57.7 |
| 15.5 | 109.5 |
| 15.6 | 43.6 |
| 15.7 | 66.0 |
| 16 | 14.9 |
| 17A | 8.1 |
| 17B | 9.4 |
| 18 | 44.2 |
| 19 | 1.3 |
| 20 | 9.1 |
| 21 | <1 |
| 22 | 25.6 |
| 22.1 | 1.1 |
| 22.2 | <1 |
| 22.3 | <1 |
| 22.4 | <1 |
| 22.5 | 1.0 |
| 22.6 | 1.2 |
| 22.7 | <1 |
| 22.8 | <1 |
| 22.9 | 2.0 |
| 23 | 3.4 |
| 24 | 1.6 |
| 24.1 | <1 |
| 24.2 | 1.1 |
| 24.3 | 2.7 |
| 24.4 | 1.0 |
| 24.5 | 1.7 |
| 24.6 | <1 |
| 25 | <1 |
| 26 | 9.4 |
| 26A | 2.4 |
| 26B | 3410 |
| 26.1 | 26.8 |
| 26.2 | 6.4 |
| 26.3 | 9.5 |
| 26.4 | 26.2 |
| 27 | 1.9 |
| 27.1 | 4.6 |
| 27.2 | 7.1 |
| 27.3 | 1.2 |
| 28 | 36.7 |
| 29 | 4.2 |
| 30A | 1.3 |
| 30B | 2.0 |
| 31 | 4.2 |
| 31.1 | 2.6 |
| 31.2 | 6.7 |
| 31.3 | 2.6 |
| 32.1 | <1 |
| 32.2 | <1 |
| 32.3 | <1 |
| 32.4 | 14.7 |
| 33 | <1 |
| 34 | 3.2 |
| 35 | 2.7 |
| 36 | 7.2 |
| 37 | <1 |
| 37.1 | 3.7 |

TABLE 28-continued

| Example | IC$_{50}$ [nM] |
|---|---|
| 37.2 | 9.3 |
| 37.3 | 1.9 |
| 37.4 | 1.7 |
| 38.1 | 37.7 |
| 38.2 | 34.1 |
| 39 | 7.0 |
| 40 | 2.2 |
| 41 | 1.4 |
| 41A | <1 |
| 41B | 40.4 |
| 41.1 | <1 |
| 41.2 | 1.0 |
| 41.3 | <1 |
| 41.4 | <1 |
| 41.5 | <1 |
| 41.6 | <1 |
| 41.7 | <1 |
| 41.8 | 1.4 |
| 41.9 | <1 |
| 41.10 | <1 |
| 41.11 | 1.1 |
| 41.12 | 89.5 |
| 41.13 | <1 |
| 41.14 | <1 |
| 41.15 | <1 |
| 41.16 | <1 |
| 41.17 | <1 |
| 41.18 | 1.1 |
| 41.19 | <1 |
| 41.20 | 1.7 |
| 41.21 | 1.5 |
| 41.22 | <1 |
| 41.23 | <1 |
| 41.24 | <1 |
| 41.25 | 1.5 |
| 41.26 | <1 |
| 41.27 | <1 |
| 41.28 | <1 |
| 41.29 | <1 |
| 41.30 | <1 |
| 41.31 | <1 |
| 42 | <1 |
| 42.1 | <1 |
| 42.2 | 2.9 |
| 42.3 | <1 |
| 42.4 | <1 |
| 42.5 | <1 |
| 42.6 | <1 |
| 42.7 | <1 |
| 42.8 | <1 |
| 43 | <1 |
| 44 | <1 |
| 45.1 | <1 |
| 45.2 | <1 |
| 45.3 | <1 |
| 45.4 | <1 |
| 45.5 | <1 |
| 45.6 | <1 |
| 46 | <1 |
| 47.1 | <1 |
| 47.2 | <1 |
| 47.3 | <1 |
| 47.4 | <1 |
| 47.5 | <1 |
| 47.6 | <1 |
| 47.7 | <1 |
| 47.8 | <1 |
| 47.9 | <1 |
| 47.10 | <1 |
| 47.11 | <1 |
| 47.12 | <1 |
| 47.13 | <1 |
| 47.14 | <1 |
| 47.15 | <1 |
| 43.16 | <1 |
| 47.17 | <1 |
| 47.18 | <1 |
| 47.19 | <1 |
| 47.20 | <1 |
| 47.21 | <1 |
| 48.1 | <1 |
| 48.2 | <1 |
| 48.3 | <1 |
| 48.4 | <1 |
| 49 | 1.8 |
| 49A | <1 |
| 49B | 173.3 |
| 49.1 | 1.2 |
| 49.2 | 1.3 |
| 49.3 | 1.0 |
| 50.1 | 4.0 |
| 50.2 | <1 |
| 50.3 | 1.7 |
| 50.4 | 1.2 |
| 50.5 | <1 |
| 50.6 | 1.2 |
| 50.7 | <1 |
| 51.1 | 1.0 |
| 51.2 | <1 |
| 51.3 | <1 |
| 51.4 | <1 |
| 52 | <1 |
| 52A | <1 |
| 52B | 618.6 |
| 52.1 | 1.1 |
| 52.2 | <1 |
| 52.3 | <1 |
| 52.4 | <1 |
| 52.5 | <1 |
| 53.1 | <1 |
| 53.2 | <1 |
| 53.3 | <1 |
| 53.4 | <1 |
| 53.5 | <1 |
| 54.1 | 4.9 |
| 54.2 | 3.3 |
| 54.3 | 1.5 |
| 54.4 | 2.4 |
| 55 | 6.1 |
| 56.1 | <1 |
| 56.2 | <1 |
| 57 | 34.9 |

Assay for the Determination of Neutrophil Elastase Inhibitory Activity in Human Plasma Citrated blood from human healthy donors is mixed with zymosan suspension and incubated at room temperature. This leads to the stimulation of neutrophils and the release of neutrophil elastase into the plasma. The stimulated blood is centrifuged to generate the neutrophil elastase enriched plasma.

Preparation of Zymosan Working Solution:

Zymosan (100 mg) is mixed with saline (0.9%, 10 mL) and stored at 4° C. for up to one week (note: zymosan does not dissolve in the saline and is used as a suspension).

Whole Blood Stimulation:
- A single 45 ml blood sample is taken into a 50 ml tube containing citrate (3.13%, 5 mL) and the tube is gently inverted 4 times.
- Immediately after blood sampling, zymosan working solution (5 mL) is added.
- After the addition of zymosan working solution, the tubes are capped, mixed gently and incubated at 22° C. for 15 min on a shaker at 20 rpm.
- Make 10 ml aliquots after the incubation time.
- Centrifuge the 15 ml tubes at 800 g for 15 min at 4° C. in a Jouan centrifuge.
- Harvest the plasma and make 1-5 ml aliquots.
- Store the plasma at −80° C.

Various concentrations of the neutrophil elastase inhibitor are incubated with plasma. Subsequently, the enzyme activity is measured using the fluorogenic substrate MeOSuc-Ala-Ala-Pro-Val-AMC (Bachem Cat. No. 1-1270, substrate concentration: 250 µM, pH 7.5, 25 mM TRIS buffer, 250 mM NaCl) in analogous fashion as described for the human neutrophil assay. A dose response curve is generated to calculate the $EC_{50}$ of the inhibitor. The analysis of the data is performed by the calculation of the percentage of fluorescence in the presence of the test compound compared to the fluorescence of the vehicle control after subtracting the background fluorescence: An inhibitor of the neutrophil elastase enzyme will give values between 100% control (no inhibition) and 0% control (complete inhibition). The human plasma shift of selected compounds can be calculated using the following equation:

Human plasma shift=($EC_{50}$ in human plasma assay)/($IC_{50}$ in human neutrophil elastase assay)

The $EC_{50}$ values of selected compounds in the human plasma assay described above are listed in Table 29.

TABLE 29

| Example | $EC_{50}$ [µM] |
|---|---|
| 1A | 0.022 |
| 6.2 | 0.004 |
| 6.3 | 0.004 |
| 7.3 | 0.002 |
| 7.5 | 0.001 |
| 7.6 | 0.001 |
| 7.9 | 0.001 |
| 35 | 0.007 |
| 9A | 0.002 |
| 7.2A | 0.001 |
| 31 | 0.014 |
| 52.1 | <0.001 |
| 52.3 | <0.001 |
| 41.17 | 0.006 |
| 41.1 | 0.001 |
| 41.5 | 0.002 |
| 41.1 | 0.003 |
| 41.16 | 0.002 |
| 52.2 | 0.001 |
| 41.4 | 0.002 |
| 10A | 0.001 |
| 25 | 0.001 |
| 47.2 | <0.001 |
| 7.1A | 0.002 |
| 47.1 | <0.001 |
| 49.3 | 0.007 |
| 41A | <0.001 |
| 46 | 0.001 |
| 52A | <0.001 |
| 42.3 | 0.005 |
| 42.4 | 0.012 |
| 42.6 | 0.001 |
| 37.2 | 0.017 |
| 47.5 | 0.001 |
| 47.4 | <0.001 |
| 50.3 | 0.013 |
| 22 | 0.023 |
| 45.4 | 0.002 |
| 26.1 | 0.013 |
| 50.1 | 0.016 |
| 23 | <0.001 |
| 53.3 | <0.001 |
| 53.4 | <0.001 |
| 45.5 | <0.001 |
| 33 | <0.001 |
| 54.2 | <0.001 |
| 52.5 | 0.001 |
| 29 | 0.001 |
| 49A | 0.004 |
| 24.1 | 0.002 |
| 14A | 0.001 |

TABLE 29-continued

| Example | $EC_{50}$ [µM] |
|---|---|
| 24 | 0.002 |
| 30B | 0.002 |
| 30A | 0.001 |
| 15.4A | 0.002 |
| 26A | 0.002 |
| 19 | 0.002 |
| 21 | 0.001 |
| 55 | 0.003 |
| 2A | 0.003 |
| 22.4 | <0.001 |
| example 8A disclosed in WO 2005/0828683 | 0.079 |

Compared to the acyclic methyl ketone derivative (example 8A disclosed in WO 2005/0828683), the cyclic ketone example 1A exhibits a significantly lower $EC_{50}$ value, i.e. significantly improved potency, in the human plasma assay described above. Furthermore, example 1A exhibits a human plasma shift of less than 2 which is significantly lower than the human plasma shift for example 8A in WO 2005/0828683 and is likely attributable to reduced binding to human plasma proteins. This observation is surprising, since example 1A differs from example 8A in WO 2005/0828683 by only a single carbon-carbon bond.

Assay for the Determination of Metabolic Stability with Human Liver Microsomes

The metabolic degradation of the test compound is assayed at 37° C. with pooled human liver microsomes. The final incubation volume of 100 µl per time point contains TRIS buffer pH 7.6 (0.1 M), magnesium chloride (5 mM), microsomal protein (1 mg/ml) and the test compound at a final concentration of 1 µM. Following a short preincubation period at 37° C., the reactions are initiated by addition of beta-nicotinamide adenine dinucleotide phosphate, reduced form (NADPH, 1 mM) and terminated by transferring an aliquot into acetonitrile after different time points. Additionally, the NADPH-independent degradation u) is monitored in incubations without NADPH, terminated at the last time point. The [%] remaining test compound after NADPH independent incubation is reflected by the parameter c(control) (metabolic stability). The quenched incubations are pelleted by centrifugation (10,000 g, 5 min). An aliquot of the supernatant is assayed by LC-MS/MS for the amount of parent compound.

The half-life ($t_{1/2}$ INVITRO) is determined by the slope of the semilogarithmic plot of the concentration-time profile. The intrinsic clearance (CL_INTRINSIC) is calculated by considering the amount of protein in the incubation:

CL_INTRINSIC[µl/min/mg protein]=(ln 2/(half-life [min]*protein content [mg/ml]))*1,000.

The half-life ($t_{1/2}$ INVITRO) values of selected compounds in the metabolic stability assay described above are listed in Table 30.

TABLE 30

| Example | $t_{1/2}$ INVITRO [min] |
|---|---|
| 1A | >130 |
| 6.3 | >130 |
| 7.3 | >130 |
| 7.6 | >130 |
| 35 | >130 |
| 9A | >130 |
| 7.2A | >130 |
| 31 | >130 |

TABLE 30-continued

| Example | $t_{1/2}$ INVITRO [min] |
|---|---|
| 52.1 | >130 |
| 52.3 | >130 |
| 41.17 | >130 |
| 41.1 | >130 |
| 41.1 | >130 |
| 41.16 | >130 |
| 52.2 | >130 |
| 41.4 | >130 |
| 10A | >130 |
| 25 | >130 |
| 47.2 | >130 |
| 7.1A | >130 |
| 47.1 | >130 |
| 49.3 | >130 |
| 41A | >130 |
| 46 | >130 |
| 52A | >130 |
| 22.4 | >130 |
| 42.3 | >130 |
| 42.4 | >130 |
| 14 | >130 |
| 47.5 | >130 |
| 37.4 | >130 |
| 47.4 | >130 |
| 50.3 | >130 |
| 22 | >130 |
| 45.4 | >130 |
| 26.1 | >130 |
| 23 | >130 |
| 15.4 | >130 |
| 53.3 | >130 |
| 53.4 | >130 |
| 45.5 | >130 |
| 33 | >130 |
| 15.6 | >130 |
| 54.2 | >130 |
| 52.5 | >130 |
| 29 | >130 |
| 49A | >130 |
| 24.1 | 100 |
| 14A | >130 |
| 24 | >130 |
| 30B | >130 |
| 30A | >130 |
| 15.4A | >130 |
| 26A | >130 |
| 19 | >130 |
| 21 | >130 |
| 55 | >130 |
| example 8A disclosed in WO 2005/0828683 | 74 |

Compared to the acyclic methyl ketone derivative (example 8A disclosed in WO 2005/0828683), the cyclic ketone example 1A exhibits improved half life, i.e. improved stability, in the metabolic stability assay described above. This observation is surprising, since example 1A differs from example 8A in WO 2005/0828683 by only a single carbon-carbon bond.

Assay for the Determination of Metabolic Stability with Human Hepatocytes

The metabolic degradation of the test compound is assayed in a human hepatocyte suspension. Human hepatocytes (typically cryopreserved) are incubated in an appropriate buffer system (e.g. Dulbecco's modified eagle medium plus 3.5 µg glucagon/500 mL, 2.5 mg insulin/500 mL and 3.75 mg/500 mL hydrocortison) containing 5% species serum. Following a (typically) 30 mM preincubation in an incubator (37° C., 10% $CO_2$), 5 µl of test compound solution (80 µM; from 2 mM stock solution in DMSO diluted 1:25 with medium) are added into 395 µl hepatocyte suspension (cell density in the range 0.25-5*$10^6$ cells/mL, typically 1*$10^6$ cells/mL; final concentration of test compound 1 µM, final DMSO concentration 0.05%). The cells are incubated for six hours (incubator, orbital shaker) and samples (25 µl) are taken at 0, 0.5, 1, 2, 4 and 6 hours. Samples are transferred into acetonitrile and pelleted by centrifugation (5 min) The supernatant is transferred to a new 96-deepwell plate, evaporated under nitrogen and resuspended. The decline of parent compound is analyzed by LC-MS/MS.

The intrinsic clearance CL_INTRINSIC is calculated as follows:

$$\text{CL\_INTRINSIC} = \text{Dose/AUC} = (C_0/\text{CD})/(\text{AUD} + c_{last}/k)*1{,}000/60$$

($C_0$: initial concentration in the incubation [µM], CD: cell density of vital cells [$10^6$ cells/mL], AUD: area under the data [µM*h], $c_{last}$: concentration of last data point [µM], k: slope of the regression line for parent decline [$h^{-1}$])

The calculated in vitro hepatic intrinsic clearance can be scaled up to the intrinsic in vivo hepatic clearance and used to predict hepatic in vivo blood clearance (CL) by the use of a liver model (well stirred model):

$$\text{CL\_INTRINSIC\_INVIVO [ml/min/kg]} = (\text{CL\_INTRINSIC [µL/min/10}^6\text{ cells]} * \text{hepatocellularity [10}^6\text{ cells/g liver]} * \text{liver factor [g/kg bodyweight]})/1{,}000$$

$$\text{CL [ml/min/kg]} = \text{CL\_INTRINSIC\_INVIVO [ml/min/kg]} * \text{hepatic blood flow [ml/min/kg]}/(\text{CL\_INTRINSIC\_INVIVO [ml/min/kg]} + \text{hepatic blood flow [ml/min/kg]})$$

$$Q_h[\%] = \text{CL [ml/min/kg]/hepatic blood flow [ml/min/kg]}$$

(Hepatocellularity, human: 120*$10^6$ cells/g liver; lver factor, human: 25.7 g/kg bodyweight; blood flow, human: 21 ml/(min*kg))

The predicted human hepatic in vivo blood clearance (CL) of selected compounds in the metabolic stability assay described above is listed in Table 31.

TABLE 31

| Example | CL [ml/min/kg] |
|---|---|
| 1A | 6 |
| 6.2 | 6 |
| 6.3 | 4 |
| 7.3 | 7 |
| 9A | 0 |
| 7.2A | 0 |
| 41.17 | 3 |
| 41.1 | 2 |
| 52.2 | 3 |
| 41.4 | 5 |
| 10A | 0 |
| 25 | 2 |
| 47.2 | 1 |
| 7.1A | 3 |
| 47.1 | 0 |
| 49.3 | 0 |
| 41A | 0 |
| 52A | 8 |
| 42.4 | 0 |
| 42.6 | 5 |
| 14 | 4 |
| 50.1 | 1 |
| 23 | 0 |
| 15.4 | 0 |

TABLE 31-continued

| Example | CL [ml/min/kg] |
|---|---|
| 53.3 | 0 |
| 53.4 | 0 |
| 45.5 | 0 |
| example 8A disclosed in WO 2005/0828683 | 10 |

Compared to the acyclic methyl ketone derivative (example 8A disclosed in WO 2005/0828683), the cyclic ketone example 1A exhibits reduced clearance, i.e. improved stability, in the metabolic stability assay described above. This observation is surprising, since example 1A differs from example 8A in WO 2005/0828683 by only a single carbon-carbon bond.

Assay for Determination of Drug Transport Across Human Caco-2 Cells

The assay provides information on the potential of a compound to pass the cell membrane, on the extent of oral absorption as well as on whether the compound is actively transported by uptake and/or efflux transporters. For the measurement of permeability across polarized, confluent human cancer colon carcinoma cells 2 (Caco-2) cell monolayers grown on permeable filter supports are used as the in vitro absorption model.

Apparent permeability coefficients (PE) of the compounds across the Caco-2 monolayers are measured (pH 7.2, 37° C.) in apical-to-basal (AB) (absorptive) and basal-to-apical (BA) (secretory) transport direction. AB permeability (PEAB) represents drug absorption from the intestine into the blood and BA permeability (PEBA) drug secretion from the blood back into the intestine via both passive permeability as well as active transport mechanisms mediated by efflux and uptake transporters that are expressed on the Caco-2 cells. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB suggests the involvement of an apical efflux transporter (like P-gp) and/or basolateral uptake transporter; higher PEAB than PEBA permeability suggests involvement of an apical uptake transporter (like PepT1) and/or basolateral efflux transporter (like MRP3). Active transport is concentration-dependently saturable.

Caco-2 cells ($1-2*10^5$ cells/cm$^2$ area) are seeded on filter inserts (Costar transwell polycarbonate or PET filters, 0.4 nm pore size) and cultured (DMEM) for 10 to 25 days. Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$×7H$_2$O, 0.41 mM NaH$_2$PO$_4$×H$_2$O, 15 mM HEPES, 20 mM glucose, pH 7.2) to prepare the transport solutions (typically 10 μM compound, final DMSO <=0.5%). The transport solution (TL) is applied ici to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by LC-MS/MS or scintillation counting. Sampled receiver volumes are replaced with fresh receiver solution.

The apparent permeability coefficients (PEAB and PEBA) and efflux ratios (PEBA/PEAB) of selected compounds in the Caco-2 drug transport assay described above are listed in Table 32.

TABLE 32

| Example | PEAB [cm/s] | PEBA [cm/s] | Efflux ratio |
|---|---|---|---|
| 1A | 0.000051 | 0.0000764 | 1.5 |
| 7.3 | 0.00000949 | 0.0000671 | 7.1 |
| 35 | 0.0000569 | 0.0000738 | 1.3 |
| 9A | 0.0000439 | 0.000073 | 1.7 |
| 7.2A | 0.00000403 | 0.0000633 | 15.7 |
| 31 | 0.0000809 | 0.0000695 | 0.9 |
| 52.1 | 0.0000571 | 0.0000583 | 1.0 |
| 41.17 | 0.0000234 | 0.0000807 | 3.5 |
| 41.1 | 0.00000816 | 0.0000729 | 8.9 |
| 41.5 | 0.00000885 | 0.000077 | 8.7 |
| 41.1 | 0.0000188 | 0.0000903 | 4.8 |
| 41.16 | 0.0000589 | 0.0000577 | 1.0 |
| 52.2 | 0.0000708 | 0.0000803 | 1.1 |
| 41.4 | 0.00000941 | 0.0000815 | 8.7 |
| 10A | 0.000004925 | 0.0000574 | 14.5 |
| 25 | 0.0000567 | 0.000074 | 1.3 |
| 47.2 | 0.0000128 | 0.0000845 | 6.6 |
| 7.1A | 0.0000727 | 0.0000681 | 0.9 |
| 47.1 | 0.00000813 | 0.0000651 | 8.0 |
| 41A | 0.0000111 | 0.0000751 | 6.8 |
| 42.3 | 0.0000362 | 0.000086 | 2.4 |
| 42.4 | 0.0000397 | 0.000078 | 2.0 |
| 37.2 | 0.0000849 | 0.0000998 | 1.2 |
| 47.5 | 0.0000192 | 0.0000867 | 4.5 |
| 47.4 | 0.00000774 | 0.0000855 | 11.1 |
| 50.3 | 0.0000724 | 0.0000681 | 0.9 |
| 22 | 0.0000365 | 0.0000545 | 1.5 |
| 45.4 | 0.0000381 | 0.0000772 | 2.0 |
| 26.1 | 0.0000677 | 0.0000642 | 0.9 |
| 50.1 | 0.0000667 | 0.0000661 | 1.0 |
| 23 | 0.0000103 | 0.0000935 | 9.1 |
| 53.4 | 0.00000985 | 0.0000944 | 9.6 |
| 33 | 0.00000908 | 0.0000712 | 7.8 |
| 52.5 | 0.00000445 | 0.0000627 | 14.1 |
| 29 | 0.0000118 | 0.0000662 | 5.6 |
| 49A | 0.0000831 | 0.0000648 | 0.8 |
| 14A | 0.0000103 | 0.0000948 | 9.2 |
| 24 | 0.0000625 | 0.0000856 | 1.4 |
| 30B | 0.000012 | 0.0000714 | 5.9 |
| 30A | 0.00000352 | 0.000039 | 11.1 |
| 15.4A | 0.000003 | 0.000046 | 15.0 |
| 26A | 0.000072 | 0.000076 | 1.1 |
| 2A | 0.000087 | 0.000069 | 0.8 |
| example 4 disclosed in WO 2007/129060 | 0.0000060 | 0.000035 | 5.8 |
| example 44 disclosed in US 2011/0034433 | 0.0000009 | 0.000014 | 15.5 |
| example 38 disclosed in US 2011/0034433 | 0.0000002 | 0.0000028 | 17.1 |

Compared to the cyclic amide derivative (example 4 disclosed in WO 2007/129060), the cyclic ketone example 1A exhibits improved AB permeability and a reduced efflux ratio. The AB permeability and efflux ratio of example 1A are in the favorable range for an orally administered drug.

Compared to the cyclic amide derivative (example 44 disclosed in US 2011/0034433), the cyclic ketone example 10A exhibits improved AB permeability.

Compared to the cyclic amide derivative example 38 disclosed in US 2011/0034433 bearing a carbamoyl (R—NH—C(=O)—) substituent at the dihydropyrimidinone nitrogen, a) numerous examples of the invention bearing a carbamoyl (R—NH—C(=O)—) substituent at the dihydropyrimidinone nitrogen exhibit improved AB permeability and/or a reduced efflux ratio.

Assay for Determination of Aqueous Solubility

The aqueous solubility of a compound is determined by comparing the amount dissolved in aqueous buffer (containing 2.5% DMSO) to the amount dissolved in an acetonitrile/water (1/1) solution. Starting from a 10 mM DMSO stock solution, aliquots are diluted with acetonitrile/water (1/1) and McIlvaine buffer pH 6.8, respectively. After 24 h of shaking, the solutions or suspensions are filtered and analyzed by LC-UV. The amount dissolved in buffer is compared to the amount dissolved in the acetonitrile/water (1/1) solution. Solubility is measured from 0.001 to 0.125 mg/ml at a DMSO concentration of 2.5%. If more than 90% of the compound is dissolved in buffer, the value is marked with ">".

The aqueous solubility of selected compounds in the solubility assay described above is listed in Table 33.

TABLE 33

| Example | Aqueous solubility [mg/mL] |
| --- | --- |
| 1A | 0.074 |
| 6.2 | 0.077 |
| 6.3 | 0.121 |
| 7.3 | 0.072 |
| 7.5 | 0.104 |
| 7.6 | 0.094 |
| 7.9 | 0.106 |
| 7.2A | 0.072 |
| 52.1 | 0.041 |
| 52.3 | 0.091 |
| 41.17 | 0.054 |
| 41.1 | 0.097 |
| 41.5 | 0.082 |
| 41.1 | 0.073 |
| 52.2 | 0.016 |
| 41.4 | 0.092 |
| 10A | 0.0845 |
| 25 | 0.062 |
| 47.2 | 0.045 |
| 7.1A | 0.023 |
| 47.1 | 0.083 |
| 49.3 | 0.032 |
| 41A | 0.079 |
| 46 | 0.01 |
| 52A | 0.088 |
| 42.3 | 0.02 |
| 42.4 | 0.021 |
| 42.6 | 0.067 |
| 14 | 0.045 |
| 47.5 | 0.016 |
| 37.4 | 0.021 |
| 47.4 | 0.019 |
| 22 | 0.013 |
| 45.4 | 0.028 |
| 26.1 | 0.041 |
| 50.1 | 0.041 |
| 23 | 0.015 |
| 15.4 | 0.069 |
| 53.3 | 0.034 |
| 53.4 | 0.014 |
| 45.5 | 0.056 |
| 33 | 0.043 |
| 15.6 | 0.076 |
| 54.2 | 0.044 |
| 52.5 | 0.07 |
| 29 | 0.079 |
| 24.1 | 0.064 |
| 14A | 0.062 |
| 30B | 0.065 |
| 30A | 0.051 |
| 15.4A | 0.069 |

TABLE 33-continued

| Example | Aqueous solubility [mg/mL] |
| --- | --- |
| 26A | 0.041 |
| 19 | 0.089 |
| 21 | 0.087 |
| 2A | 0.07 |

Assay for Determination of Cytochrome P450 2C9 Inhibition

The inhibition of cytochrome P450 2C9-isoenzyme catalysed hydroxylation of Diclofenac by the test compound is assayed at 37° C. with human liver microsomes. All assays are carried out on a robotic system in 96 well plates. The final incubation volume contains TRIS buffer (0.1 M), $MgCl_2$ (5 mM), human liver microsomes (0.1 mg/ml), Diclofenac (10 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (sulfaphenazole) is determined. Experimental $IC_{50}$ values are calculated by least square regression according to the following equation:

$$\% \text{ control activity} = (100\% \text{ control activity}/(1 \pm (I/IC_{50})*S))-B$$

(I=inhibitor concentration, S=slope factor, B=background activity)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned ">highest concentration tested" (usually >50 µM).

The $IC_{50}$ values of selected compounds in the CYP2C9 inhibition assay described above are listed in Table 34.

TABLE 34

| Example | CYP2C9 $IC_{50}$ [µM] |
| --- | --- |
| 1A | >50 |
| 10A | >50 |
| 9A | >50 |
| 7.2A | >50 |
| 41A | >50 |
| 47.1 | >50 |
| 47.2 | >50 |
| example 8A disclosed in WO 2005/0828683 | 12 |

Compared to the acyclic methyl ketone derivative (example 8A disclosed in WO 2005/0828683), the cyclic ketone example 1A exhibits reduced CYP2C9 inhibition in the assay described above. This observation is surprising, since example 1A differs from Example 8A in WO 2005/0828683 by only a single carbon-carbon bond.

Assay for Determination of Cytochrome P450 2C19 Inhibition

The inhibition of cytochrome P450 2C19-isoenzyme catalysed hydroxylation of Mephenytoin by the test compound is assayed at 37° C. with human liver microsomes. All assays are carried out on a robotic system in 96 well plates. The final incubation volume contains TRIS buffer (0.1 M), MgCl$_2$ (5 mM), human liver microsomes (0.5 mg/ml), (S)-Mephenytoin (70 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC$_{50}$ of a positive control inhibitor (tranylcypromine) is determined Experimental IC$_{50}$ values are calculated by least square regression according to the following equation:

% control activity=(100% control activity/
  (1±(I/IC$_{50}$)*S))–B (I=inhibitor concentration, S=slope factor, B=background activity)

If the inhibition of the reaction is already >50% at the lowest concentration of the test compound, the IC$_{50}$ is assigned "<lowest concentration tested" (usually <0.4 µM). If the inhibition of the reaction is still <50% at the highest concentration of the test compound, the IC$_{50}$ is assigned ">highest concentration tested" (usually >50 µM).

The IC$_{50}$ values of selected compounds in the CYP2C19 inhibition assay described above are listed in Table 35.

TABLE 35

| Example | CYP2C19 IC$_{50}$ [µM] |
|---|---|
| 1A | >50 |
| 10A | 39 |
| 9A | >50 |
| 7.2A | >50 |
| 41A | >50 |
| 47.1 | >50 |
| 47.2 | >50 |
| example 8A disclosed in WO 2005/0828683 | 7.3 |

Compared to the acyclic methyl ketone derivative (example 8A in WO 2005/0828683), the cyclic ketone example 1A exhibits reduced CYP2C19 inhibition in the assay described above. This observation is surprising, since example 1A differs from example 8A in WO 2005/0828683 by only a single carbon-carbon bond.

Assay for Determination of Cytochrome P450 2C8 Inhibition

The inhibition of cytochrome P450 2C8-isoenzyme catalysed deethylation of Amodiaquine by the test compound is assayed at 37° C. with human liver microsomes. All assays are carried out on a robotic system in 96 well plates. The final incubation volume contains TRIS buffer (0.1 M), MgCl$_2$ (5 mM), human liver microsomes (0.05 mg/ml), Amodiaquine (1 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution— usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC$_{50}$ of a positive control inhibitor (Montelukast) is determined Experimental IC$_{50}$ values are calculated by least square regression according to the following equation:

% control activity=(100% control activity/
  (1±(I/IC$_{50}$)*S))–B (I=inhibitor concentration, S=slope factor, B=background activity)

If the inhibition of the reaction is already >50% at the lowest concentration of the test compound, the IC$_{50}$ is assigned "<lowest concentration tested" (usually <0.4 µM). If the inhibition of the reaction is still <50% at the highest concentration of the test compound, the IC$_{50}$ is assigned ">highest concentration tested" (usually >50 µM).

The IC$_{50}$ values of selected compounds in the CYP2C8 inhibition assay described above are listed in Table 36.

TABLE 36

| Example | CYP2C8 IC$_{50}$ [µM] |
|---|---|
| 1A | >50 |
| 10A | >50 |
| 9A | >50 |
| 7.2A | >50 |
| 41A | >50 |
| 47.1 | >50 |
| 47.2 | >50 |
| example 8A disclosed in WO 2005/0828683 | 10.9 |

Compared to the acyclic methyl ketone derivative (example 8A disclosed in WO 2005/0828683), the cyclic ketone example 1A exhibits reduced CYP2C8 inhibition in the assay described above. This observation is surprising, since example 1A differs from example 8A in WO 2005/0828683 by only a single carbon-carbon bond.

Combinations

The compounds of general formula 1 may be used on their own or combined with other active substances of formula 1 according to the invention. The compounds of general formula 1 may optionally also be combined with other pharmacologically active substances. These include, β2-adrenoceptor-agonists (short and long-acting), anticholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors, non-steroidale anti-inflammatory agents (NSAIDs), Cathepsin C (or DPPI/Dipeptidylaminopeptidase I) inhibitors, CRTH2 antagonists, DP1-receptor modulators, Thromboxane receptor antagonists, CCR3 antagonists, CCR4 antagonists, CCR1 antagonists, CCR5antagonists, CCR6 antagonists, CCR7 antagonists, CCR8 antagonists, CCR9 antagonists, CCR30 antagonists, CXCR3 antagonists, CXCR4 antagonists, CXCR2 antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergicreceptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immuno-therapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, i.e.:

Betamimetics with corticosteroids, PDE4-inhibitors, CRTH2-inhibitors or LTD4-antagonists,
Anticholinergics with betamimetics, corticosteroids, PDE4-inhibitors, CRTH2-inhibitors or LTD4-antagonists,
Corticosteroids with PDE4-inhibitors, CRTH2-inhibitors or LTD4-antagonists
PDE4-inhibitors with CRTH2-inhibitors or LTD4-antagonists
CRTH2-inhibitors with LTD4-antagonists.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury; acute respiratory distress syndrome;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome andSazary syndrome;

7. oncology: treatment of common cancers including prostate, breast, lung, ovarian, pancre-atic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, Candida, aspergillus, cryptococcal meningitis, *Pneumocystis* carnii, cryptosporidiosis, histoplasmosis, toxoplasmosis, trypanosome infection and leishmaniasis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:
1. A compound of formula 1

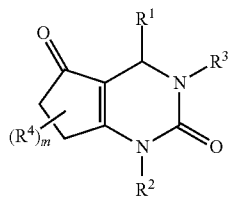

wherein
$R^1$ is phenyl or a five- or six-membered heteroaryl, wherein one, two or three ring carbon atoms are replaced by a heteroatom independently selected from the group consisting of N, O or S; each ring optionally substituted with one, two or three substituents independently selected from the group consisting of halogen, $O_2N$—, NC—, $H_2N$—, HO—, $R^{1.1}$, $R^{1.1}O$— and $R^{1.2}$;
  $R^{1.1}$ independently selected from the group consisting of $C_{1-6}$-alkyl-, $C_{3-6}$-cycloalkyl-, $C_{1-6}$-haloalkyl- and $C_{3-6}$-halocycloalkyl;
  $R^{1.2}$ is HO—$C_{1-6}$-alkyl- or $R^{1.1}$—O—$C_{1-6}$-alkyl-;
$R^2$ is phenyl or a five- or six-membered heteroaryl, wherein one or two ring carbon atoms are replaced by a heteroatom independently selected from the group consisting of N, O or S; each ring optionally substituted with a substituent independently selected from the group consisting of halogen, $C_{1-4}$-alkyl-, $C_{1-4}$-haloalkyl- and $C_{1-4}$-alkyl-O—;
$R^3$ is a residue independently selected from the group consisting of
  $R^{3.1}$—;
  $R^{3.2}$(O)C—;
  $R^{3.2}$O(O)C—;
  $R^{3.2}$O(O)C-A-;
  $R^{3.2}$S—; $R^{3.2}$(O)S—; $R^{3.2}$(O)$_2$S—;
  $(R^{3.2})_2$N(O)C and
  $(R^{3.2})_2$N(O)C-A-;
  $R^{3.1}$ is independently selected from the group consisting of H, $R^{3.3}$, $R^{3.4}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from $R^{3.1.1}$—;
  $R^{3.1.1}$ is selected from the group consisting of HO—, halogen, NC—, $R^{3.3}$O—, $R^{3.5}$, $R^{3.6}$ and $R^{3.7}$ or $R^{3.1.1}$ denotes a ring independently selected from phenyl and a four-membered heterocyclic ring containing one heteroatom independently selected from among N, O, S, S(O) and S(O)$_2$;
$R^{3.1.1}$ denotes a five- or six-membered heterocyclic or heteroaryl ring containing one, two or three heteroatoms independently selected from among N, O, S, S(O) and S(O)$_2$;
  each of the rings optionally substituted with one or two substituents independently selected from among HO—, O=, halogen, NC—, $R^{3.3}$, $R^{3.3}$O—, $R^{3.3}$—(O)C—, $R^{3.4}$, $R^{3.5}$, $R^{3.6}$, and $R^{3.7}$ or two substituents are together $R^{3.8}$;
$R^{3.2}$ is independently selected from among $R^{3.1}$, phenyl and a five- or six-membered heterocyclic or heteroaryl ring containing one, two or three heteroatoms independently selected from among N, O, S, S(O) and S(O)$_2$; each ring optionally substituted with one or two substituents independently selected from among HO—, O=, NC—, halogen, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$;
  or two $R^{3.2}$ are together a three-, four-, five- or six-membered monocyclic or a six-, seven-, eight-, nine- or ten-membered bicyclic heterocyclic or heteroaryl ring optionally containing additional to the nitrogen one or two heteroatoms independently selected from among N, O, S, S(O) and S(O)$_2$; optionally substituted with one or two substituents, independently selected from among HO—, F, O=, NC—, $R^{3.3}$, $R^{3.3}$O—, $R^{3.3}$—(O)C—, $R^{3.4}$, $R^{3.5}$, $R^{3.6}$, $R^{3.7}$, phenyl and a five- or six-membered heterocyclic or heteroaryl ring containing one, two or three heteroatoms independently selected from among N, O, S, S(O) and S(O)$_2$; or two substituents are together $R^{3.8}$;
$R^{3.3}$ is independently selected from the group consisting of $C_{1-6}$-alkyl-, $C_{3-6}$-cycloalkyl-, $C_{1-6}$-haloalkyl- and $C_{3-6}$-halocycloalkyl;
$R^{3.4}$ is HO—$C_{1-6}$-alkyl- or $R^{3.3}$—O—$C_{1-6}$-alkyl-;
$R^{3.5}$ is independently selected from the group consisting of $H_2N$—, $R^{3.3}$—HN—, $(R^{3.3})_2N$—, $R^{3.3}$—(O)C—HN— and $R^{3.3}$—(O)C—$(R^{3.3})$N—;
$R^{3.6}$ is independently selected from the group consisting of $R^{3.3}$—(O)S—, $R^{3.3}$—(O)$_2$S—, $R^{3.3}$(HN)S—, $R^{3.3}$(HN)(O)S—, $R^{3.3}(R^{3.3}N)S$—, $R^{3.3}(R^{3.3}N)(O)S$—, $R^{3.3}(R^{3.4}N)S$—, $R^{3.3}(R^{3.4}N)(O)S$—; $R^{3.3}$(NC—N)S and $R^{3.3}$(NC—N)(O)S—;
$R^{3.7}$ is independently selected from the group consisting of HO(O)C—, $H_2N(O)C$—, $R^{3.3}$—O—(O)C—, $R^{3.3}$—NH—(O)C— and $(R^{3.3})_2N$—(O)C—;
$R^{3.8}$ is independently selected from the group consisting of $C_{1-6}$-alkylene and $C_{1-6}$-haloalkylene, wherein optionally one or two CH$_2$-groups are replaced by —HN—, —$(R^{3.3})N$—, —$(R^{3.4})N$—, —$R^{3.3}(O)C$—)N—, —$(R^{3.4}(O)C$—)N—, —O—, —S—, —S(O)— or —S(O)$_2$—;
A is —CH$_2$—, —CH$_2$—CH$_2$— or —CH$_2$—CH$_2$—CH$_2$—; optionally substituted with one or two substituents independently selected from the group consisting of halogen, $R^{3.3}$, $R^{3.3}$O— and $R^{3.4}$ or two substituents together are $R^{3.8}$;
$R^4$ is independently selected from the group consisting of halogen, $C_{1-6}$-alkyl-, $C_{3-6}$-cycloalkyl-, $C_{1-6}$-haloalkyl- and $C_{3-6}$-halocycloalkyl; or two $R^4$ are together $C_{1-6}$-alkylene or $C_{1-6}$-haloalkylene;
m is 0, 1 or 2;
or a salt thereof.

2. A compound of formula 1, according to claim 1, wherein $R^1$ is $R^{1.c}$ and $R^{1.c}$ is phenyl or pyridinyl; each ring optionally substituted by one, two or three residues independently selected from the group consisting of F, Cl, Br—, NC—, and $R^{1.1}$;

$R^{1.1}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{1.2}$ is HO—$C_{1-6}$-alkyl- or $R^{1.1}$—O—$C_{1-6}$-alkyl-;

or a salt thereof.

3. A compound of formula 1, according to claim 1, wherein $R^1$ is $R^{1.e}$ and $R^{1.e}$ is phenyl or pyridinyl; each ring optionally substituted by one or two NC— residues; or a salt thereof.

4. A compound of formula 1, according to claim 1, wherein $R^2$ is $R^{2.b}$ and $R^{2.b}$ is phenyl or a six-membered heteroaryl; wherein one or two ring carbon atoms are replaced by N; each ring optionally substituted with a substituent independently selected from the group consisting of halogen, $C_{1-4}$-alkyl- and $C_{1-4}$-haloalkyl-; or a salt thereof.

5. A compound of formula 1, according to claim 1, wherein $R^2$ is $R^{2.f}$ and $R^{2.f}$ is pyridinyl, optionally substituted with a substituent independently selected from the group consisting of $F_3C$— and $F_2HC$—, or a salt thereof.

6. A compound of formula 1, according to claim 1, wherein A is $A^b$ and $A^b$ is —$CH_2$—, optionally substituted with one or two substituents independently selected from the group consisting of F, Me, Et, i-Pr, MeO, EtO, $HOCH_2O$— and $MeOCH_2$—; or a salt thereof.

7. A compound of formula 1, according to claim 1, wherein $R^4$ is $R^{4.a}$ and $R^{4.a}$ is selected from the group consisting of halogen, $C_{1-6}$-alkyl-, $C_{3-6}$-cycloalkyl-, $C_{1-6}$-haloalkyl- and $C_{3-6}$-halocycloalkyl; or a salt thereof.

8. A compound of formula 1, according to claim 1, wherein $R^3$ is a residue independently selected from the group consisting of $R^{3.1}$—;

$R^{3.2}O(O)C$— or $R^{3.2}O(O)C$—$CH_2$—;

$R^{3.2}(O)_2S$— and $(R^{3.2})_2N(O)C$— or $(R^{3.2})_2N(O)C$—$CH_2$—;

$R^{3.1}$ is independently selected from the group consisting of H, $R^{3.3}$, $R^{3.4}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from $R^{3.1.1}$—;

$R^{3.1.1}$ is selected from the group consisting of HO—, halogen, NC—, $R^{3.3}O$—, $R^{3.5}$, $R^{3.6}$ and $R^{3.7}$ or $R^{3.1.1}$ is selected from the group consisting of a ring independently selected from phenyl and a four-membered heterocyclic ring containing one heteroatom independently selected from among N, O, S, S(O) and $S(O)_2$; or $R^{3.1.1}$ denotes a five- or six-membered heterocyclic or heteroaryl ring containing one, two or three heteroatoms independently selected from among N, O, S, S(O) and $S(O)_2$; each of the rings optionally substituted with one or two substituents independently selected from among HO—, O=, halogen, $R^{3.3}$, $R^{3.3}O$—, $R^{3.3}$—(O)C—, $R^{3.4}$, $R^{3.5}$, $R^{3.6}$ and $R^{3.7}$ or two substituents are together $R^{3.8}$;

$R^{3.2}$ is independently selected from $R^{3.1}$, phenyl or a five- or six-membered heterocyclic or heteroaryl ring containing one, two or three heteroatoms independently selected from among N, O, S, S(O) and $S(O)_2$; each ring optionally substituted with one or two substituents independently selected from HO—, O=, NC—, halogen, $R^{3.3}$, $R^{3.3}O$—, $R^{3.3}$—(O)C—, $R^{3.4}$, $R^{3.5}$, $R^{3.6}$ and $R^{3.7}$ or two substituents are together $R^{3.8}$;

or two $R^{3.2}$ are together a five- or six-membered monocyclic or a eight-, nine- or ten-membered bicyclic heterocyclic or heteroaryl ring optionally containing additional to the nitrogen one or two heteroatoms independently selected from among N, O, S, S(O) and $S(O)_2$; optionally substituted with one or two substituents, independently selected from HO—, F, O=, $R^{3.3}$, $R^{3.3}O$—, $R^{3.3}$—(O)C—, $R^{3.4}$, $R^{3.5}$, $R^{3.7}$ and $R^{3.6}$ or two substituents are together $R^{3.8}$;

$R^{3.3}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{3.4}$ is HO—$C_{1-6}$-alkyl- or $R^{3.3}$—O—$C_{1-6}$-alkyl-;

$R^{3.5}$ is independently selected from the group consisting of $H_2N$—, $R^{3.3}$—HN—, $(R^{3.3})_2N$— and $R^{3.3}$—(O)C—HN—;

$R^{3.6}$ is independently selected from the group consisting of $R^{3.3}$—(O)S—, $R^{3.3}$—(O)$_2$S—, $R^{3.3}$(HN)S—, $R^{3.3}$(HN)(O)S—$R^{3.3}(R^{3.3}N)S$—, $R^{3.3}(R^{3.3}N)(O)S$—, $R^{3.3}(R^{3.4}N)S$— and $R^{3.3}(R^{3.4}N)(O)S$—;

$R^{3.7}$ is independently selected from the group consisting of HO(O)C—, $H_2N(O)C$—, $R^{3.3}$—O—(O)C—, $R^{3.3}$—NH—(O)C— and $(R^{3.3})_2N$—(O)C—;

$R^{3.8}$ is independently selected from the group consisting of $C_{1-6}$-alkylene or $C_{1-6}$-haloalkylene, wherein optionally one or two $CH_2$-groups are replaced by —HN—, —$(R^{3.3})N$—, —$(R^{3.4})N$—, —$(R^{3.3}(O)C$—)N—, —$(R^{3.4}(O)C$—)N—, —O—, —S—, —S(O)— and —$S(O)_2$—;

or a salt thereof.

9. A compound of formula 1, according to claim 1, wherein $R^3$ is independently selected from the group consisting of HO(O)C—$H_2C$—, MeO(O)C—$H_2C$—, $H_2N(O)C$—$H_2C$—, MeHN(O)C—$H_2C$—, $Me_2N(O)C$—$H_2C$—, morpholinyl-(O)C—$H_2C$—, azetidinyl-(O)C—$H_2C$—, pyrrolidinyl-(O)C—$H_2C$—, MeHN(O)C—, EtHN(O)C—, HO$(CH_2)_2$HN(O)C—, HO$(CMe_2)(CH_2)HN(O)C$—, HO$(CH_2)_3$HN(O)C—, Me(O)S$(CH_2)_2$HN(O)C—, Me$(O)_2S(CH_2)_2$HN(O)C—, Et$(O)_2S$— and Me$(O)_2S$—; or a salt thereof.

10. A compound of formula 1, according to claim 1, which is selected from one of the following compounds:

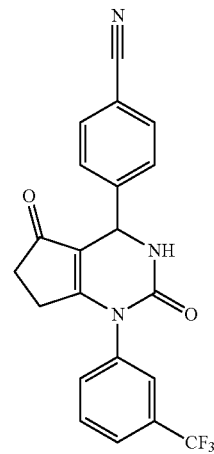 [SMILES: N#Cc1ccc(C2NC(=O)N(c3cccc(C(F)(F)F)c3)C3=C2C(=O)CC3)cc1]

I.a

| 189 -continued | 190 -continued |
|---|---|
| 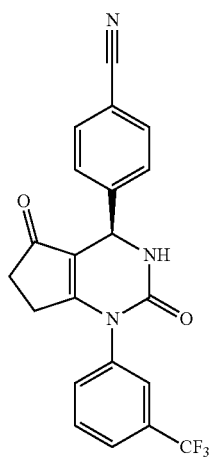 [SMILES: N#Cc1ccc([C@H]2NC(=O)N(c3cccc(C(F)(F)F)c3)C3=C2C(=O)CC3)cc1] I.b | 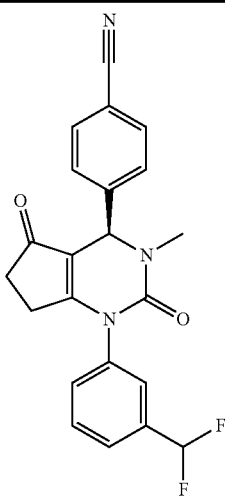 I.j |
| 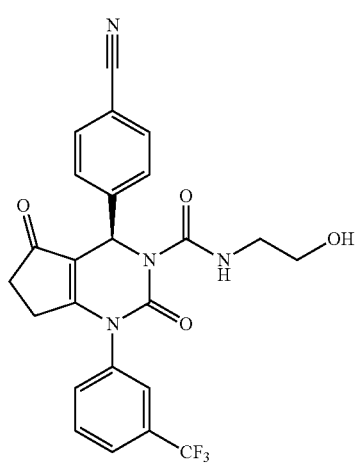 [SMILES: N#Cc1ccc([C@@H]2C3=C(CCC3=O)N(c3cccc(C(F)(F)F)c3)C(=O)N2C(=O)NCCO)cc1] I.c | 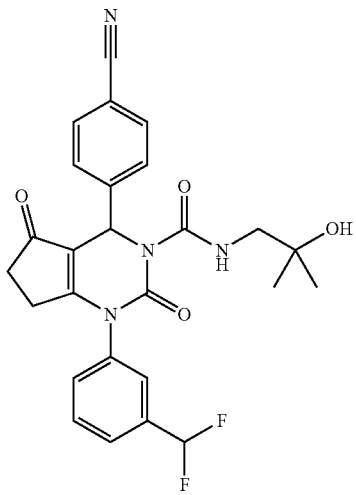 I.n |
| 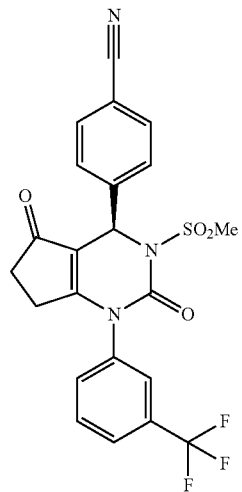 [SMILES: CS(=O)(=O)N1C(=O)N(c2cccc(C(F)(F)F)c2)C2=C(C(=O)CC2)[C@H]1c1ccc(C#N)cc1] I.d | |
or a salt thereof.

11. A compound according to claim 1, wherein the configuration of formula 1 is formula 1'

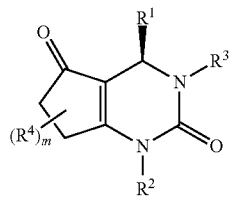

or a salt thereof.

12. A pharmaceutical composition comprising a compound of formula 1 according to claim 1 or a pharmaceutically acceptable salt thereof and a pharmaceutically acceptable carrier.

13. A method for treating chronic obstructive pulmonary disease comprising administering to a host suffering from chronic obstructive pulmonary disease a therapeutically effective amount of a compound of formula 1 according claim 1 or a pharmaceutically acceptable salt thereof.

14. A compound according to claim 1, of the formula

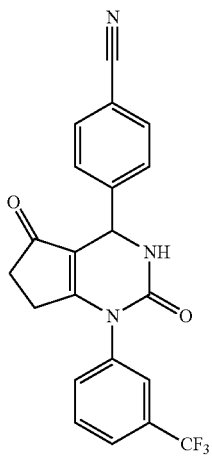

(Ex 1)

or a pharmaceutically acceptable salt thereof.

15. A pharmaceutical composition comprising a compound according to claim 14, or a pharmaceutically acceptable salt thereof, and a pharmaceutically acceptable carrier.

16. A method for treating chronic obstructive pulmonary disease comprising administering to a host suffering from chronic obstructive pulmonary disease a therapeutically effective amount of a compound according to claim 14 or a pharmaceutically acceptable salt thereof.

17. A compound according to claim 1, of the formula

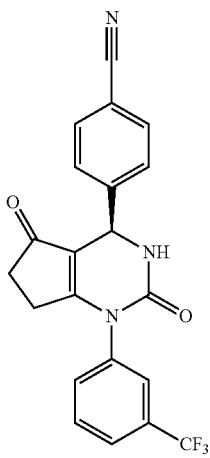

(Ex 1A)

or a pharmaceutically acceptable salt thereof.

18. A pharmaceutical composition comprising a compound according to claim 17, or a pharmaceutically acceptable salt thereof, and a pharmaceutically acceptable carrier.

19. A method for treating chronic obstructive pulmonary disease comprising administering to a host suffering from chronic obstructive pulmonary disease a therapeutically effective amount of a compound according claim 17 or a pharmaceutically acceptable salt thereof.

20. The compound according to claim 1, of the formula

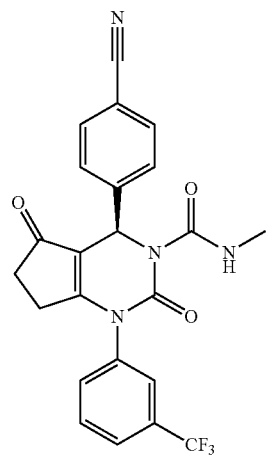

(Ex 7.1A)

or a pharmaceutically acceptable salt thereof.

21. A pharmaceutical composition comprising a compound according to claim 20, or a pharmaceutically acceptable salt thereof, and a pharmaceutically acceptable carrier.

22. A method for treating chronic obstructive pulmonary disease comprising administering to a host suffering from chronic obstructive pulmonary disease a therapeutically effective amount of a compound according claim 20 or a pharmaceutically acceptable salt thereof.

23. The compound according to claim 1, of the formula:

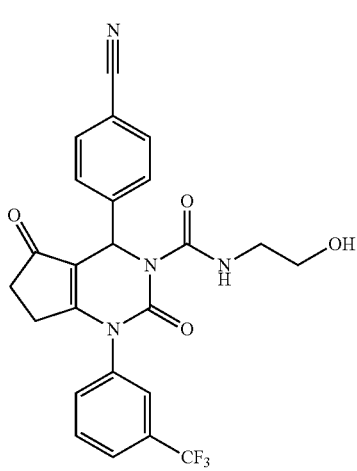

(Ex 7.2)

or a pharmaceutically acceptable salt thereof.

24. A pharmaceutical composition comprising a compound according to claim 23, or a pharmaceutically acceptable salt thereof, and a pharmaceutically acceptable carrier.

25. A method for treating chronic obstructive pulmonary disease comprising administering to a host suffering from chronic obstructive pulmonary disease a therapeutically effective amount of a compound according claim 23 or a pharmaceutically acceptable salt thereof.

26. The compound according to claim 1, of the formula

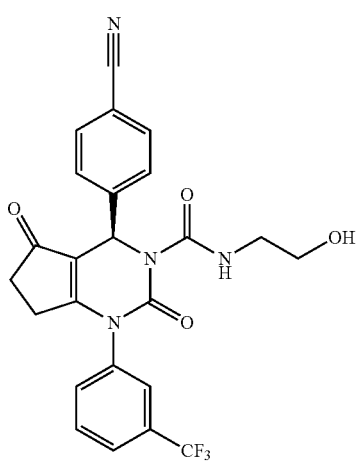

(Ex 7.2A)

or a pharmaceutically acceptable salt thereof.

27. A pharmaceutical composition comprising a compound according to claim 26, or a pharmaceutically acceptable salt thereof, and a pharmaceutically acceptable carrier.

28. A method for treating chronic obstructive pulmonary disease comprising administering to a host suffering from chronic obstructive pulmonary disease a therapeutically effective amount of a compound according claim 26 or a pharmaceutically acceptable salt thereof.

29. The compound according to claim 1, of the formula (Ex 7.2B)

or a pharmaceutically acceptable salt thereof.

30. A pharmaceutical composition comprising a compound according to claim 29, or a pharmaceutically acceptable salt thereof, and a pharmaceutically acceptable carrier.

31. A method for treating chronic obstructive pulmonary disease comprising administering to a host suffering from chronic obstructive pulmonary disease a therapeutically effective amount of a compound according claim 29 or a pharmaceutically acceptable salt thereof.

32. The compound according to claim 1, of the formula

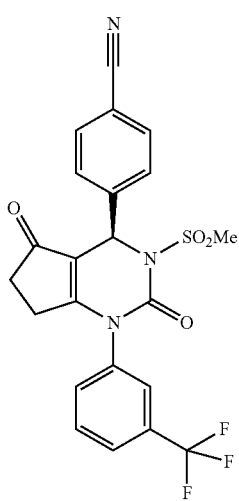

(Ex. 9A)

or a pharmaceutically acceptable salt thereof.

33. A pharmaceutical composition comprising a compound according to claim 32, or a pharmaceutically acceptable salt thereof, and a pharmaceutically acceptable carrier.

34. A method for treating chronic obstructive pulmonary disease comprising administering to a host suffering from chronic obstructive pulmonary disease a therapeutically effective amount of a compound according claim 32 or a pharmaceutically acceptable salt thereof.

35. The compound according to claim 1, of the formula

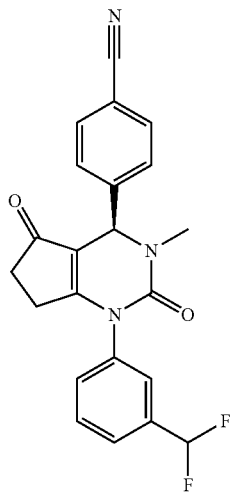 [SMILES: CN1C(=O)N(c2cccc(C(F)F)c2)C2=C(C(=O)CC2)[C@H]1c1ccc(C#N)cc1]

(Ex. 26A)

or a pharmaceutically acceptable salt thereof.

36. A pharmaceutical composition comprising a compound according to claim 35, or a pharmaceutically acceptable salt thereof, and a pharmaceutically acceptable carrier.

37. A method for treating chronic obstructive pulmonary disease comprising administering to a host suffering from chronic obstructive pulmonary disease a therapeutically effective amount of a compound according claim 35 or a pharmaceutically acceptable salt thereof.

38. The compound according to claim 1, of the formula

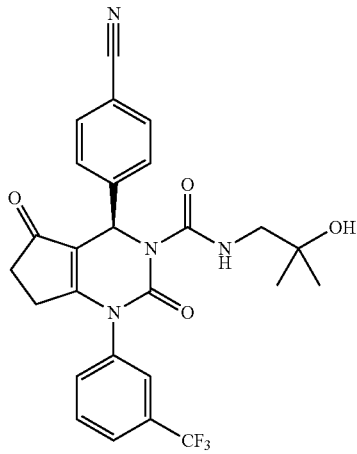

(Ex 41A)

or a pharmaceutically acceptable salt thereof.

39. A pharmaceutical composition comprising a compound according to claim 38, or a pharmaceutically acceptable salt thereof, and a pharmaceutically acceptable carrier.

40. A method for treating chronic obstructive pulmonary disease comprising administering to a host suffering from chronic obstructive pulmonary disease a therapeutically effective amount of a compound according claim 38 or a pharmaceutically acceptable salt thereof.

41. The compound according to claim 1, of the formula

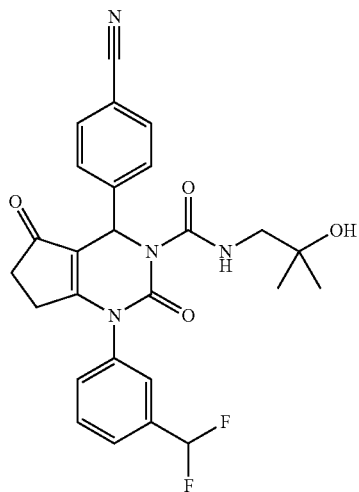

(Ex. 52.5)

or a pharmaceutically acceptable salt thereof.

42. A pharmaceutical composition comprising a compound according to claim 41, or a pharmaceutically acceptable salt thereof, and a pharmaceutically acceptable carrier.

43. A method for treating chronic obstructive pulmonary disease comprising administering to a host suffering from chronic obstructive pulmonary disease a therapeutically effective amount of a compound according claim 41 or a pharmaceutically acceptable salt thereof.

* * * * *

UNITED STATES PATENT AND TRADEMARK OFFICE
CERTIFICATE OF CORRECTION

PATENT NO.         : 9,290,459 B1                          Page 1 of 1
APPLICATION NO.    : 14/935915
DATED              : March 22, 2016
INVENTOR(S)        : Christian Gnamm et al.

It is certified that error appears in the above-identified patent and that said Letters Patent is hereby corrected as shown below:

IN THE SPECIFICATION

In column 174, appearing at line 14, please replace "WO 2005/0828683" with --WO 2005/082863--
In column 174, appearing at line 17, please replace "WO 2005/0828683" with --WO 2005/082863--
In column 174, appearing at line 22, please replace "WO 2005/0828683" with --WO 2005/082863--
In column 174, appearing at line 25, please replace "WO 2005/0828683" with --WO 2005/082863--
In column 175, appearing at line 45, please replace "WO 2005/0828683" with --WO 2005/082863--
In column 175, appearing at line 49, please replace "WO 2005/0828683" with --WO 2005/082863--
In column 175, appearing at line 53, please replace "WO 2005/0828683" with --WO 2005/082863--
In column 177, appearing at line 8, please replace "WO 2005/0828683" with --WO 2005/082863--
In column 177, appearing at line 12, please replace "WO 2005/0828683" with --WO 2005/082863--
In column 177, appearing at line 16, please replace "WO 2005/0828683" with --WO 2005/082863--
In column 180, appearing at line 55, please replace "WO 2005/0828683" with --WO 2005/082863--
In column 180, appearing at line 59, please replace "WO 2005/0828683" with --WO 2005/082863--
In column 180, appearing at line 62, please replace "WO 2005/0828683" with --WO 2005/082863--
In column 181, appearing at line 45, please replace "WO 2005/0828683" with --WO 2005/082863--
In column 181, appearing at line 49, please replace "WO 2005/0828683" with --WO 2005/082863--
In column 181, appearing at line 52, please replace "WO 2005/0828683" with --WO 2005/082863--
In column 182, appearing at line 34, please replace "WO 2005/0828683" with --WO 2005/082863--
In column 182, appearing at line 37, please replace "WO 2005/0828683" with --WO 2005/082863--
In column 182, appearing at line 40, please replace "WO 2005/0828683" with --WO 2005/082863--

Signed and Sealed this
Thirty-first Day of May, 2016

Michelle K. Lee
*Director of the United States Patent and Trademark Office*